US008306610B2

(12) United States Patent
Mirow

(10) Patent No.: US 8,306,610 B2
(45) Date of Patent: Nov. 6, 2012

(54) METHOD AND APPARATUS FOR ANALYSIS OF PSYCHIATRIC AND PHYSICAL CONDITIONS

(76) Inventor: Susan Mirow, Salt Lake City, UT (US)

( * ) Notice: Subject to any disclaimer, the term of this patent is extended or adjusted under 35 U.S.C. 154(b) by 1043 days.

(21) Appl. No.: 12/226,285

(22) PCT Filed: Apr. 18, 2007

(86) PCT No.: PCT/US2007/009420
§ 371 (c)(1),
(2), (4) Date: Oct. 14, 2008

(87) PCT Pub. No.: WO2007/123923
PCT Pub. Date: Nov. 1, 2007

(65) Prior Publication Data
US 2009/0292180 A1    Nov. 26, 2009

Related U.S. Application Data

(60) Provisional application No. 60/792,766, filed on Apr. 18, 2006.

(51) Int. Cl.
*A61B 5/0402* (2006.01)

(52) U.S. Cl. .................................................. 600/509
(58) Field of Classification Search .................. 600/301, 600/509, 513
See application file for complete search history.

(56) References Cited

U.S. PATENT DOCUMENTS 6,658,287 B1   12/2003   Litt et al.
2004/0230105 A1*  11/2004   Geva et al. .................. 600/301

* cited by examiner

*Primary Examiner* — Eric D. Bertram
(74) *Attorney, Agent, or Firm* — Angus C. Fox, III

(57) ABSTRACT

A method, apparatus and software for diagnosing the state or condition of a human, animal or other living thing, which always generates physiological modulating signals having temporal-spatial organization, the organization having dynamic patterns whose structure is fractal, involving the monitoring of at least one physiological modulating signal and obtaining a set of temporal-spatial values of each of said physiological modulating signals, and processing the respective temporal-spatial values using linear and nonlinear tools to determine the linear and nonlinear characteristics established for known criteria to determine the state or condition of the person, being or living things, and to use this data for diagnosis, tracking, and treatment and developmental issues.

8 Claims, 37 Drawing Sheets

METHOD AND APPARATUS FOR ANALYSIS OF PSYCHIATRIC AND PHYSICAL CONDITIONS

CROSS REFERENCE TO RELATED APPLICATION

This application is a national stage application of International Application No. PCT/US2007/009420, filed Apr. 18, 2007 which claims the benefit of U.S. provisional patent application Ser. No. 60/792,766 filed Apr. 18, 2006.

DESCRIPTION OF THE INVENTION

1. Field of the Invention

The present invention relates to methods and apparatus for diagnosing psychiatric and physical conditions and for monitoring the recovery there from and identifying psychiatric and physical conditions and for monitoring the recovery there from and identifying very early stages of disease processes and predicting outcomes from altered physiological measures, as well as for collecting and evaluating physiologic parameters of a person, and for studying development and ageing, as well as for health maintenance. The invention also relates to methods and apparatus for validating medical, psychiatric, psychological, pharmacological and social treatments, and for measuring and predicting relapses.

2. Background of the Invention

The neurobiological attributes of physical and mental states have been the focus of intensive study over recent years. These states have been depicted as linear processes of stochastic (random) systems, mapped as probability distributions. Alterations in linear measurements of neurotransmissions, secretion of hormones, and amount of metabolic product have been computed. Although this approach has resulted in a clear separation between healthy and pathological states, this linear approach has not led to progress in understanding how persistent alterations of physical and mental states evolve into physical and psychiatric illnesses, with dysregulation of previously coordinated function.

It is now known that biological systems are nonlinear in nature, where nonlinear means that the system output is not proportional to its input. Yet these systems are often treated as if they were linear and described using linear tools such as mean and standard deviation, and studied in smaller and smaller parts to understand the whole. A more accurate study of biological (nonlinear) systems is made through the use of nonlinear equations whose calculations require hundreds to thousands of data points. It wasn't until the advent of computers that the required computations for so many data points could be rapidly completed, so that the entire system could be tracked moving through time.

A biological system, (nonlinear), constantly oscillates and requires ongoing inputs of energy. As such, it exists in non-equilibrium conditions. Its oscillations are best seen during task performance when the system moves from one relatively stable state to another relatively stable state. The oscillations of the system may be tracked over time as a time series, comparing each system state with its previous system state. The result is a collection of measurements where each data point represents the state of the system at a moment in time. The data points represented by these measurements can alternatively be expressed as a series of sounds (sonification), or frequencies (spectra). The data points can also be plotted in "space," as a graph, where the spatial configuration produced is either a regular or irregular shape. This shape is called an "attractor." In general, a nonlinear system can exhibit one or more of the following types of behavior: a point attractor=forever resting (dead), periodic motion=limit cycle or quasi-periodic motion, strange attractor=chaotic motion. All of the living states are non-equilibrium states and need inputs of energy to maintain themselves.

Biological systems ensure that an organism remains in an adaptive state. When either internal (e.g., physiological or psychological) or external (e.g., environmental or social) circumstances disturb the system, the system adapts by transitioning between states, operating to return itself to a pre-perturbed state, or moving to a new, better adapted, more optimal state. This invention recognizes that tracking these transitions over time reveals patterns of adaptation that can be classified as either healthy or pathological.

Tools which allow one to observe the biological system (comprised of a human interacting with the environment) have shown that the system is nonlinear, adaptive, and self-organizing. This invention examines the total output of the brain/body system, over time, thus revealing previously hidden spatial-temporal patterns.

To date, there is little conceptual or practical integration between linear reductionist models of brain/body function and nonlinear ones; even though it is known that all biological systems are nonlinear. This patent addresses the usefulness of nonlinear measures in providing richer descriptions of biological systems than was previously available, along with their changes over time.

The nonlinear nature of consciousness has been clarified with the help of brain imaging techniques. Positron Emission Tomography (PET), Magnetic Resonance Imaging (MRI), and Magneto-encephalography (MEG), along with Quantitative Electroencephalography (qEEG) and other probes have produced visual models of the living brain in functional interaction with the environment. These new understandings are bringing into question the usefulness of the merely descriptive categories currently used to define each psychiatric and physical condition. These descriptions bear limited relationship to functional interactions of the brain and body, nor do they address the dysregulated processes that evolve into states of disease.

It is now recognized that conscious states may be represented as complex spatial-temporal patterns of neurons representing information processing within the entire brain. Spatial-temporal patterns are produced moment by moment in time, with the entire brain's excitatory and inhibitory neurons and groups of neurons, whether quiescent or active, all sharing equal importance in production of the next state (pattern).

Information processing within the entire brain is holistic in nature, where input for the next state, i.e., the next new pattern, is dependent upon the output from the previous state (pattern). This process is known as iteration. Iterated patterns read as states of health are both stable, yet flexible, appropriately modulated responses adapting to changes in the internal and external environment. In contrast, maladaptive psychiatric and physical conditions are characterized by states whose patterns are too rigid, i.e., too persistent and inflexible, or too rapidly shifting from pattern to pattern, in response to task demands. Both psychiatric and physical illnesses result in maladaptive patterns that are too short, too long, too fast, or too slow. Physical and psychiatric illnesses may be represented by their recognizable, unique, persistent, and maladaptive patterns (states). The patterns produced during these pathological states show alteration in the phasing and coordination of the body/brain's regions with their inherent biological processes, and multiple feedback loops with multiple interconnections (like the world-wide web). This invention tracks these states as quantitative measures, moving toward health or disease.

In a deterministic system, if the original state of the system is known, each subsequent state taken by the system is entirely predictable. In contrast, the original state of a biological system cannot be known for the system has too many variables to measure. Such a system is called dynamical. A dynamical system is said to show "sensitive dependence upon initial conditions," and therefore its long-term behavior is not predictable. Short-term predictions regarding system behavior can be made with the use of nonlinear mathematical tools. While it is not possible to track each variable within a dynamical system the behaviors of the entire system may be tracked as it moves through space-time. Dynamical systems are governed by a set of mathematical rules, i.e., functions that specify how their variables change over time. For example, two system states that appear to be close to each other at a given moment in time may diverge significantly from each other as time goes by. Nonlinear tools, such as the Lyapunov exponent, and the Lyapunov dimension. provide mathematical tracking of divergence between two measured points, over time. A biological system, (continually oscillatory in nature), shows transitions (dynamics) between (relatively) stable states. As a nonlinear system adapts, it displays stochastic (truly random), periodic or chaotic behaviors.

The durations of these transitions vary, depending upon how long a perturbation lasts and/or how long it takes the system to return to its former unperturbed state or to move to a new relatively stable state. This inventor has found that the dynamics of transitions between states (velocity and rate of change of velocity, etc.) provide valuable determinants of system health. FIG. 1 is a diagram entitled "Nonlinearity in Healthy Adaptation". This diagram shows how one relatively stable state transitions to the next relatively stable state. The dynamics of each transition are important here. A biological system exists in many states as it goes about its adaptive tasks. Three states of the same biological system are shown in FIG. 1. Interest lies in the transitions between states, for this is where the dynamics of the system are revealed.

Transitions of the system may be measured by velocity (rapidity) of adaptive response, as well as by rate of change of velocity (acceleration or deceleration) of the system's oscillatory behavior, along with frequency (number of oscillations) and amplitude (size) of the oscillations. Velocity of response reveals the system's sensitivity to change, while rate of change of velocity is indicated by the frequency of periods of transitions, a measure of system stability. For example, a greater number of transitions within a system suggest either more frequent perturbation or an overall increased sensitivity to perturbation, while the size of transitions measure magnitude of perturbation and stability of the system.

Sometimes the oscillations of a nonlinear biological system may be usefully described using linear mathematical functions. For example, the movement of limbs during ordinary locomotion (walking) can be represented mathematically as sinusoidal waves (a "limit cycle"). Other, more complex oscillations, along with their associated state changes, cannot be adequately described using linear functions. Instead, nonlinear mathematical functions are needed. An example of oscillatory movements best described using nonlinear math is the complicated movements of human dance.

It is this inventor's hypothesis that insights derived from the study of nonlinear systems will one day lead to a "new psychiatry" and a "new medicine", whose previously descriptive categories will give way to biological understanding of system state changes that reflect those processes mapped by structural and functional neuroanatomical and body-imaging, patterns of information processing, moving through time. Like footprints, these "brain and body prints" trace healthy paths through time, just as they track the unfolding of psychiatric and physical illnesses.

The complexities of mood, emotion and physical movement offer an evolutionary advantage, producing ever-changing patterns in response to novel environments. The evolutionary emergence of mood and emotion, in contrast to "hardwired" behavior, i.e., "fixed action patterns" (aggressive or mating displays) confers unpredictability in response. Moods and emotions, themselves the result of nonlinear brain activity, cannot be accurately forecast over long time periods, (due to their "sensitive dependence upon initial conditions"), yet short-term predictions of mood and emotional state can be made by tracking their spatial-temporal patterns over time. Fully nuanced mood and emotional expressions develop slowly in humans as they grow from infancy to adulthood. A baby exhibits abrupt discontinuous changes in mood and emotional state, whereas a healthy mature adult has modulated, appropriate moods and emotional responses to change.

In humans, moods and emotions appear as an evolutionary adaptation, allowing flexibility in response to an unpredictable world. Life saving states such as "flight/fight/freeze", while more rapidly processed by the brain (faster firing nerves with fewer connections), provide little flexibility in expression. By contrast, ever-changing moods and emotional states, allow flexibility in adaptive responses to an unpredictable, dynamical world. The human brain has several regions incorporating mood and emotional states, and they are connected to one another by multiple (web-like) feedback loops. Examples are the limbic, autonomic and the reticular activating systems.

The autonomic nervous system is responsible for orchestrating the "hard-wired" behavioral responses for basic life functions such as breathing, feeding, sexual, territorial and aggressive behaviors. These behavioral patterns are shared by all members of a given species.

The reticular activating system is sensitive to changing external stimuli, and is its multiply-connected cells are responsible for the production of a sleep-wake cycle and for focusing attention. When one of our senses produces an unvarying input, the reticular activating system directs the brain to attend to other senses.

The limbic system, a region of interconnected nerve cells, deep within the brain, imparts emotional meaning to thoughts and perceptions while incorporating information from other brain area. Individual nerve cells within the limbic system form complex connections with each other as well as with nerve cells of other brain regions. Their complex connectivity is due to spatial connectively among cells as well as to their coordinated temporal relationship with other brain areas. Limbic cell connectivity is more complicated than that of the autonomic or reticular activating systems. The limbic system incorporates information from regions below it (autonomic nervous and reticular activating systems) producing emotional charge, which in turn leads to complex behavioral patterns based upon personal experience. The limbic system retains a memory of these emotional responses along with their learned patterns of behavioral expression, each one, in turn, influencing the next set of responses. Iterated limbic patterns mirror responses that are characteristic of both the species and the individual. Limbic patterns are more individualized and therefore more flexible than the responses of the reticular activating and autonomic nervous systems.

Examples of limbic patterns are bonding behaviors between mating pairs, and the extended emotional interactions between a mother and newborn. These patterns are iterated (the result of one pattern, becomes the input for the next) over time, producing behaviors characteristic of attachment and attunement processes (infant/parent interaction). At this level of cerebral integration various biological rhythms are entrained (coupled) to each other as well as to the environment, rather than being 'internally bound' (bound within the brain/body) as in "fixed-action patterns." The limbic system integrates drive states (feeding, fighting, fleeing, sexual activity) with feeling states (mood and emotion) yielding precisely focused volitional responses whose patterns interact with a broad range of environments.

Environmental pressures illustrate the effect of stress in everyday life. Prolonged chronic, unpredictable stress can still fall within "normal" range of reactions but can cause decreased work performance and quality of life. When stress becomes overwhelming integrated function may be compromised. With chronic stress information processing suffers with the net result a reduction in the range of adaptive responses to environmental change. Persistent dysfunctional patterns of mood and emotional states are recognizable as alterations in function associated with evolution of psychiatric and/or physical illness. Pathological environments, whether emotional or physical, can change the brain in enduring ways, constricting both the range and intensity of emotional expression. Successful treatment of psychiatric and physical illness, by whatever method, returns emotional responsiveness to physiological norms and provides increased adaptive capacity. Healthy states of mood and emotion provide both flexibility and stability for task performance. As the brain ages, it's coordinated, complex patterns of physical and psychological response become more restricted and less coordinated, resulting in inflexible and/or unpopulated responses to change, thereby limiting both physical and psychological adaptation. As explained earlier, the system comprising brain and body is holistic in its output, a dynamical system, with many parts coordinating over different time scales. Various types of nerves have different speeds at which they conduct impulses. Nerve bundles that produce behaviors of "fight, flight and freeze," for example, conducted more rapidly than those that produce thoughts. Importantly, both the nerves that fire their impulses as well as the ones that don't, make up the behavior of the entire system.

The future pattern a system takes is dependent upon its previous patterns, and therefore is a measure of system stability, while the time it takes for a spatial-temporal pattern to change to another one defines adaptation of the system. Adaptation therefore depends upon how long a pattern is constrained into one shape. The shape (in space-time) and motions of these brain patterns maintain a "memory" of that constraint. The constraint (expressed as degrees of freedom) determines how the pattern shape "settles in," i.e., how deep the well is (how much energy/time the system needs to get out of the well). Some psychiatric conditions, such as depression, have constrained, i.e., rigid, patterns forming deep wells. Characteristics of one type of depression are persistent sleep disturbance along with a paucity of movement (psychomotor retardation). Other illnesses, such as the manic episodes of Bipolar Disorder (Bipolar Type I), have patterns that too easily undergo shape-shifting (i.e., shallow wells). Some physical conditions have patterns with wells whose "shape" is abnormal due to disease processes. Hypertension, for example is a pathological adaptation of the cardiovascular system, caused by a combination of 'trait', i.e., genetics, lipid metabolism, and 'state', i.e., diet, exercise, weight, cholesterol, stress, etc.

The evolution in complexity in brain organization is due to self-organization. This organization is responsible for the emergent system of mood and emotion. Nuanced mood and emotional states confer evolutionary advantage, allowing fine discrimination in response to novel (internal/external) environments. Still available to individuals in times of danger are the more rapid emotional/physical responses such as fight/flight or freeze.

The foregoing linear explanation reviewed brain functioning in terms of its component parts, while the explanation of its holistic outputs provides a nonlinear view. Examples of several psychiatric and physical disorders are discussed below.

The dynamical system of moods and emotions is underlain and may be understood as a part of the pulsed rhythmic mechanisms that evolved with life. We call these pulsed oscillations circadian (24-hour) rhythms, as they follow the rhythms of our day and night. The appearance of light, a photon, is the quantum pulse that sets the clock for its 24-hour rhythm. Timekeeper "CLOCK" genes, conserved over evolutionary time, exist in many organisms, including human beings, and they play a crucial role in coordinating biological processes.

These CLOCK genes respond to both elapsed and local time brought about by photons interacting with receptors. In simple organisms, light acts directly upon each cell, while in complex organisms, such as humans, specialized receptor cells in the retina receive light energy as photons. These retinal cells change the quantum energy of a photon into electrical energy, whose wave travels along the nerve's surface, finding their way along nerve axons to reach specialized receptor cells within the brain. These clock-setting receptor cells, located in the suprachiasmic nucleus of the hypothalamus, receive the electrical energy and convert it into back into quantum packets of photons which set the clock. The change of energy from one form to another, through cellular processes is known as "signal transduction." Nonlinearity is at work here, so that minute changes in the quantity of photons reaching the cells of the suprachiasmic nucleus can effectively re-set the central clock in the brain.

Furthermore, alterations in emotional state directly change the sensitivity of receptor cells, including the receptor cells sensitive to light (cells within the suprachiasmic nucleus of the hypothalamus). This, in turn, activates "early" genes (c-fos), important in the setting of the central clock. Thus, stress-induced changes in emotional state produce physical changes in the responsiveness of nerve cells, which in turn, over time, may evolve to organ or system dysfunction. An example of a physical condition caused, in part, by stress-related alterations in function, is that of gastric ulcers. Gastric ulcers are produced, in part, through a reversed day/night pattern of gastric acid secretion that has been found to be stress-related. Another condition in which altered timing of biological rhythms is important is that of Major Depression, where the normal diurnal variation of the 24-hour temperature rhythm is reversed, and is no longer entrained to the circadian cycle. After successful treatment of this condition, the temperature rhythm is once again appropriately synchronized to the circadian cycle.

The body's circadian rhythms are not fixed and may be altered by stress. Stressors acting upon circadian rhythms produce diagnosable conditions such as "Jet-lag" and "Circadian Rhythm Dysregulated Sleep Disorders." "Jet-lag"—a response to transmeridian flight—causes desynchronization of the environmental cues of sleep and wakefulness (light/dark cycle) to the body's temperature rhythm. Likewise, alterations in diurnal regulation of circadian rhythms are felt to be responsible for the sleep disturbance accompanying Major Depression, as well as for the sleep disturbance that accompanies Narcolepsy.

When circadian rhythms are viewed on a microscopic (micro) scale, they are seen to consist of rhythms of shorter duration, coupled (entrained) to each other as well as to the environment. Rhythms less than 24 hours in duration are called ultradian. Ultradian rhythms are intrinsic, endogenous (endogenous=developing or originating within an organism or part of an organism) oscillations found in all living things. Ultradian rhythms interplay with genes to produce the flux of signals that control heartbeat, temperature, hormone release, sleep/wake cycles and other essential biological functions.

Ultradian rhythms are physiological oscillations that serve as both process and product of their own self-organization. Ultradian rhythms self-organize during human development, orchestrating the timed processes of life with great precision. These rhythms are entrained to each other, integrated through their multiple web-like, interconnected feedback loops, as well as temporally related to each other for their functional connections. Self-organization and self-synchronization of these oscillations serve as a fundamental regulatory mechanism in all living beings. Ultradian rhythmic patterns can be studied by plotting a physiological rhythm as a time series. Alternatively, the spatial-temporal states taken by an ultradian rhythm may be mapped in state-space to produce a geometric pattern. Ultradian rhythms, at every level of self-organization are self-similar in nature, independent of scale, and their patterns are infinitely complex. The properties of self-organization, self-similarity, and infinite complexity, regardless of scale, describe a class of geometric objects called fractals. A fractal is an object in space or a process in time, whose pieces resemble the whole. Fractals are irregular in shape and cannot be defined by traditional geometry, but can be described using nonlinear analytic tools. Fractals possess infinite detail, self-similar and independent of scale, and their complexity is the result of interations of a mathematic formula. For example, trees and ferns are fractal in nature, their complicated shapes made from iterations of simpler patterns. Fractals can be modeled on a computer using a recursive (iterative) algorithm or can be represented as a geometric object which can be divided into parts, each of which is similar to the original object. The mathematical properties of fractals allow their scale-free comparisons and study at all levels of magnification, from microscopic-to mesoscopic to macroscopic. Ultradian rhythms are fractals. Ultradian fractals coordinate processes within, between and among cells, within and among organs and among systems of organs, as well as coordinating social rhythms. It is important to understand that self-organization of non-specific physiological rhythms, i.e., ultradian oscillations with their myriad interconnected feedbacks, produce, a precise "timepiece," a clock capable of orchestrating the timed processes of life.

Ultradian rhythms are ultimately and originally entrained by photonic impulses, and thus are carriers of biologically essential information from environment to organism. Fundamental activities of the organism, i.e., respiration, temperature, sleep/wake cycles, etc., are entrained to our planet's pattern of light and dark. Alterations in ultradian rhythms are found in both physical and psychiatric disease. For example, the ultradian rhythm of a physiological measure is altered in cancer with the result that prominent ultradian peaks of particular frequencies found. When treatment for the cancer is unable to re-establish the circadian rhythm, the prognosis is grave. Other physical diseases, such as Guillain-Barre Syndrome (Acute Demyelinating Polyneuropathy), Epilepsy and Migraines, as well as Diabetes and Hypertension show characteristic patterns of ultradian peaks in their biological rhythms. Panic Disorder and Depression, as well as Schizophrenia and Alzheimer's Type Dementia, are characterized by persistent alterations in the variability of heart rate or movement with their characteristic patterns. For the recognition of different physical and psychiatric conditions, two or more physiological rhythms, varying orthogonally, must be tracked through time, so that a unique ultradian pattern may be recognized. There are a few diseases, however, where a single physiological parameter, taken alone, produces a recognizable and unique pattern of a particular condition. A type of relapsing Malaria, for example, shows its unique and characteristic ultradian peaks of temperature within a 24-hour temperature rhythm.

As part of this invention, the inventor demonstrates that patterns of ultradian rhythms change in characteristic ways over the course of a person's lifetime. Thus, the precise measurement of ultradian oscillations over time, track human development, states of health and disease, as well as provide a measure to gauge healing and maintenance of healthy states.

Over evolutionary time, ultradian rhythms, viewed on a macroscopic scale, are transducers of "social information" between individuals and among the societies in which an organism exists. As shown in rabbits, interaction between mother and neonate entrains rhythms such as suckling behavior and feeding patterns. Even prenatally, mesoscopic interactions between mother and unborn rabbit appear to establish an anticipatory pattern of arousal that is dependent upon the mother's circadian rhythm. An example in humans of ultradian rhythms as transducers of social information is found in the synchronous timing of gastric acid secretion in members of a family who are briefly apart from each other, in different time zones, but who are accustomed to eating together at home at a particular time. These humans will secrete gastric acid together at the time they expect to eat together, regardless of local time.

The significance of circadian rhythms and their dysregulation in conditions such as Sleep Apnea, and Circadian Rhythm Sleep Disorders are well known. Dysregulated ultradian rhythms are also known to accompany disorders, such as Down's syndrome (trisomy 21), closed head injury and Restless Legs syndrome, Diabetes Mellitus, obesity, asthma and glaucoma.

When a system is stressed, ultradian rhythms may lose their entrainment to the circadian cycle, and their higher frequency oscillations may become prominent. During states of health, ultradian rhythms are entrained to the 24-hour circadian cycle, and as such, frequently go unnoticed due to the fact that the circadian cycle is a strong harmonic. The circadian cycle it is often thought of as linear in nature, due to its periodic oscillations, i.e., a "limit cycle." An environmental cue, a "zeitgeber" (light-giver, light-setter) sets the circadian cycle (clock) which, in turn, modulates higher frequency fluctuations, i.e., the ultradian oscillations synchronization of environmental cues of light and dark to the sleep/wake cycle and to the 24-hour temperature and circadian rhythm cause "Jet-Lag"—a response to trans-meridian flight. When Jet-Lag occurs, prominent ultradian peaks appear during sleep, corresponding to epochs of night-time awakening. Clinically this corresponds with difficulty in falling asleep and staying asleep upon returning home after crossing several time meridians traveling west. "Jet-Lag" is even worse when traveling East across meridians, because the ultradian temperature. FIG. 2 shows Jet-Lag and the mechanism by which it occurs, i.e., loss of coupling (entrainment) between the 24 hour temperature rhythm and the sleep-wake rhythm. Both temperature and sleep-wake rhythms are represented in each of the four quadrants of FIG. 2. The drawings represent paths made by the two rhythmic cycles, from a small mammal kept in constant darkness for a period of 100 days. Temperature is on the x-axis while sleep-wake is on the y-axis. On day 1, both cycles of temperature and sleep-wake are precisely coupled to each other over 24 hours, shown by the arrows as a single oval path in the top left quadrant. In the top left quadrant, the circadian cycle (strongest harmonic) entrains yet hides the 24 hour temperature rhythm. In the absence of light (needed to set the 24 hour circadian clock) this long, smoothly entrained harmonic cycle becomes shorter and eventually disappears entirely. By day 25 of constant darkness, sleep-wake (two stars as shown in the top left quadrant) and temperature rhythms both have periods shorter than 24 hours, yet they stay relatively synchronized to each other. From days 26-50 of constant darkness, as shown in the top right quadrant, the two rhythms trace even shorter, more desynchronized paths, with their shorter, ultradian cycles becoming even more visible. The stars on the upper right drawing mark the temperature rhythmic cycle. As the mammal continues to remain in constant darkness during days 51-75, as shown in the bottom left quadrant, further desynchronization of these two rhythms occur. Now each ultradian rhythm traces its own cycle, making it difficult to ascertain what path is made by the sleep-wake cycle and what path is taken by the rhythm of temperature. Maximal desynchronization of these two cycles occur between days 76-100, as shown in the bottom right quadrant, with the trajectories of each rhythm nearly impossible to see. Finally, the tracing looks like a tangled skein of wool. In humans, traveling across time-zones, the temperature rhythm takes longer to re-synchronize to the 24 clock that does the sleep-wake cycle, thereby—producing the desynchronization known as "Jet-lag." The ultradian oscillations of temperature become desynchronized to the environmental cues for sleep when transmeridian travel occurs. The temperature rhythm is slow to re-synchronize.

Neat, smooth cycles may show continuity with discrete oscillations, and on occasion, discontinuities. Discontinuous change is an event called a "catastrophe". Mathematically, a catastrophe is recognized as an abrupt change in the periodicity of a system, involving a bifurcation variable. The study of catastrophes is called Catastrophe Theory. Catastrophe Theory has been applied nonlinear measures on a macroscopic scale. For example, nonlinear analysis of mood within an organization reveals that a sudden overall change in mood accurately predicts a prison riot or, in other organizations, an increased number of work-related injuries. On a mesoscopic scale, nonlinear analysis of catastrophes has been found to be important in the genesis of epileptic seizures. A catastrophe may be understood as the point of in time at which a transition occurs. Catastrophe Theory has provided us topological models of pathological processes, including evolving pathophysiological states. It has been hypothesized that the clinical symptoms of both physical and psychiatric conditions may be related to less healthy adaptations with their global effects on system dynamics. A system in transition may move through from a catastrophe to a less organized state, called Chaos. Mathematically, chaos is "hidden order," organization within a system that appears to be exhibiting random behavior. Chaos Theory allows one to predict the behavior of a dynamical system under stress Recursion within a complex system provides stability yet still allow small perturbations to produce substantial effects on system state, permitting the system flexibility in response to environmental novelty, as well. It is known that biological systems 'balance' in this way, close to (mathematical) chaos, able to respond to small perturbations with either damping of the incoming signal or with a change of state.

Self-Organization & Entropy—Entropy has several definitions—ability of a system to do work; or a measure of the disorder in a system or alternatively, the tendency of a system to enter a more probable state, usually described as being able to create chaos from order, although the opposite holds true, as well. Order is the regularity of interaction between an object and subject.

For periods of time, a dynamical biological system may exist in what appears to be a steady state, a limit cycle, yet the system is in non-equilibrium conditions, needing a constant influx of energy. As the system performs a task, it moves (temporarily) to a more disordered state. This dynamical instability is called 'chaos'. Chaos, a scientific term, refers to a type of (hidden) organization that is not random, yet when viewed superficially it may appear to be random. The system may also show unsteady behavior at the boundary between phases. This is the catastrophe, characterized by periodic, quasiperiodic or chaotic evolution. Clinically, as a system adapts to physical, psychological or social stress, the system may oscillate even more. If the system is stressed even harder, forward-feed iterations ("positive" feedback) may cause the system to find another adaptation, going through a transition to re-organize itself. Transitions are high entropy events for the system, as the system becomes more disordered moving toward chaos. One of the ways in which a system can move toward chaos is via a catastrophe such as period-doubling, where the system bifurcates showing abrupt fluctuations between two or more states.

Ultradian rhythms entrained to one another are often hidden within the smooth, strong harmonic of the circadian cycle with its diurnal variation. This is similar to the way that the sound from an individual instrument is hidden within the harmonics of a well playing orchestra. Stress induces disorganization of ultradian rhythms and their entrainment to the circadian cycle. When stress disorganizes the circadian cycle, we see chaotic fluctuations accompanied by prominent ultradian peaks of particular rhythms.

Principles of nonlinear dynamics have been used to study mood. In depression, for example, the amplitude of the circadian rhythm is blunted and the normal 24-hour pattern of core body temperature is disturbed. Effective, successful treatment of depression, whether by electroconvulsive therapy (a physical treatment) or pharmacotherapy (a medication treatment) or cognitive-behavioral therapy (a psychological treatment) results in the entrainment of the ultradian temperature rhythm to a healthy, and normal, circadian pattern.

Stress induced alterations in the sleep cycle, appear to come about through mechanisms of signal transduction (transduction=a cascade of processes whereby a hormone or neurotransmitter interacts with a receptor at the surface of a cell, causing a change within the cell that affects the cells functioning). Stress results in phase delays in ultradian rhythms, resulting in a reduced transmission of the neurotransmitter, serotonin. Reduced levels of serotonin alter the sensitivity of the specialized (photoreceptor) cells that set the circadian clock in response to environmental light. A small change in the sensitivity of these specialized cells to a light signal, may lead to significant behavioral effects via phase-shifting of ultradian rhythms relative to the circadian cycle, resulting in the clinical outcome of sleep disturbance. Drugs that treat depression, such as paroxetine, do so by blocking the re-uptake of serotonin at the nerve terminal. This effect, increases ultradian rhythms at particular frequencies for particular cells within the brain, corresponding to the clinical disappearance of depression. Stress appears to produce a direct and immediate effect on the entrainment of rhythms. The effect for certain more severe stressors lasts well after the cessation of the stressor. This effect is called hysteresis. When the body cannot recover, either due to the severity of the stressor or inherent biology, the person is sensitized to stress. Synchronized biological processes can no longer return to age-appropriate and physiological norms causing maladaptive patterns to persist. For example, stress, coupled with genetics, may result in alterations of ultradian rhythms of blood pressure heralding evolving hypertension.

Posttraumatic Stress Disorder (PTSD) is understood as a pathophysiological response to severe, unpredictable environmental stress—either a single stressful event such as an earthquake, or chronic traumas such as those that occur in an abusive family. PTSD's defining symptoms are emotional numbing, alternating with hyperarousal, and/or flashbacks relating to the traumatic event(s). These symptoms are both cyclic and oscillatory. PTSD may be understood as persistent deregulation of a nonlinear system in response to perturbation, with resulting loss of finely discriminated emotional responses. Major or even minor environmental threat or fear of threat may produce catastrophic patterns of response.

PTSD evolves sometime after occurrence of trauma. An individual's "initial condition" (psycho-physiological state at the time of trauma) may result, in either normalizing responses to trauma or in catastrophic alterations in mood and emotional state that herald the onset of PTSD.

Autonomic nervous system dysregulation is apparent in conditions of ongoing stress, such as those precursors of PTSD. During states of hyperarousal, stress sensitization leads to exaggerated responsiveness, hyper-vigilance, increased startle response, and augmented physiologic arousal to reminders of the trauma. This autonomic nervous system activation is measured by elevations in stress hormones (catecholamine excretion) correlating with symptoms. These elevations have been associated with the development of hypertension and coronary artery disease, among others.

Dysregulated ultradian rhythms may be the earliest sign of development of the process of evolving PTSD. It has been found that low resting morning cortisol levels (cortisol secretion normally follows a diurnal pattern with highest cortisol secretion in the morning) were associated with PTSD symptoms of clinical significance, rather than due to trauma exposure, per se. Ongoing trauma results in adaptation to trauma, with low urinary cortisol levels persisting for decades in those with chronic PTSD.

Ultradian rhythms dysregulated by stress, phase-shifted and amplitude-modulated, effect processes such as pulsatile hormone release—e.g., plasma cortisol. Pulsatile release of hormones appears to promote maintenance of maximum sensitivity of hormone receptors, while phase-shifting attenuates pulsatile hormone release, producing shorter duration of peak hormone release and lower circulatory hormone levels. Sleep deprivation, for example, has been shown to phase-shift the nocturnal rise in plasma cortisol to one hour earlier in the sleep cycle. Dysregulation of pulsatile cortisol release enhances "negative" (negative feedback=feedback that reduces the output of the system), and over time, the resulting biological profile of stress sensitization—i.e., decreased circulating plasma cortisol with over-secretion under new stress (measured by hyper-suppression by the dexamethasone challenge test)—paralleling the picture for adults with chronic PTSD.

The invention relates to measuring and monitoring one or more physiologic parameters, over time, in order to diagnose illness and to track recovery from psychiatric and physical disorders. Heart rate is one such measure. The beating heart adapts to a great many internal and external stimulations or perturbations over a wide range of time scales, in response to (internal and external) environmental change. These adaptive heart rate responses can be followed as measurements of variability of heart rate over suitable time periods. This measure, known as heart rate variability is defined as the variance of a set of interbeat intervals. These interbeat intervals are usually tracked over minutes, i.e., hundreds of sequential heartbeats. Many studies have examined changes in interbeat intervals measured from a five to ten minute epoch (collection) of heartbeats. The prior art includes many studies of interbeat intervals, tracked over minutes, and reported using linear mathematics. The interbeat intervals calculated from these short time series are of the order of seconds to minutes in duration.

Changes in interbeat intervals can be extracted using Fourier, or other autocorrelation analyses of the collected heartbeat series. They are usually represented as five frequencies of the energy spectrum: very high frequency=VHF, high frequency=HF, low frequency=LF, very-low frequency=VLF and ultra-low frequency=ULF. The energy spectra are measured in hertz (Hz) where hertz is the number of cycles (waves) per second. The spectra of very high frequency (VHF) oscillations are between 0.4 and 1 Hz, high frequency (HF) oscillations are between 0.15 to 0.4 Hz, low frequency (LF) oscillations are between 0.04 to 0.15 Hz, very-low frequency (VLF) oscillations are between 0.003 to 0.04 Hz, and ultra-low frequency (ULF) oscillations are those less than 0.003 Hz in duration. The cycles (time periods) of these frequencies vary from a second (for the HF oscillations) to minutes in duration for the VLF and ULF.

FIG. 3 shows Frequency Spectrum For Heartbeats. The frequency spectrum of heart beats is plotted against power over 24 hours producing a diagram showing the relative proportion of each frequency to the variability of heart rate. The y-axis is Power in milliseconds squared, while the x-axis is Frequency in Hertz (cycles/sec). ULF=Ultra-Low Frequency oscillations, themselves due to mental processes (and other unknown factors) constitute the majority of the frequency power. VLF=Very-Low Frequency oscillations are though to be caused by the effects of hormones and of vasomotor (blood vessels opening and closing) flow. LF=Low-Frequency oscillations are thought to be due to the sympathetic nervous systems' influence as well as some parasympathetic input. HF=High-Frequency oscillations are thought to be due to parasympathetic influence on the heart beat, especially respiratory modulation of the vagus nerve, while the significance of VHF=Very-High Frequency oscillations is a yet, unknown but thought to be due to very fast breathing rhythms seen in both vigorous exercise and sleep apnea.

The invention uses long-term recording to find dynamic patterns that characterize transitions and to use these dynamical patterns to diagnose and treat disorders, and to track and maintain health.

These time scales are thought to represent system adaptations to changing (internal and external) environmental demands. VHF oscillations are understood to be due to oscillatory dynamics of rapid breathing. HF oscillations are understood to be due to the oscillatory dynamics of the parasympathetic nervous system, specifically, to the parasympathetic component of the vagus nerve. These oscillations reflect respiratory modulation of heart rate. Inhibition of the vagus nerve (parasympathetic system) in inspiration produces acceleration of heart rate; while expiration causes the heart rate to slow down. This high frequency, HF oscillation, is known as respiratory sinus arrhythmia. The LF part of the spectrum is thought to represent mostly sympathetic nervous system components with some parasympathetic components. Sympathetic nervous system fibers extend to blood vessel walls alongside the vagus nerve. LF frequency modulations are due to mechanical stretch receptors (i.e., baroreceptors) on the wall of the aortic arch and carotid arteries. Actually, these structures are innervated by both sympathetic and parasympathetic components of the autonomic nervous system arranged in multiple interconnected feedback loops (like a web). The VLF oscillations are thought to represent thermoregulatory changes as well as adaptive variations in hormone levels of renin and angiotensin. In contrast, the very short-term dynamics of intra-cardiac muscle bioelectric fields act on a beat-to-beat basis to influence heart rate. ULF frequencies are the least characterized and are thought to be due to mental and other higher order processes.

VHF, HF, LF and VLF, and ULF spectral frequencies occur over periods from fraction of seconds to minutes to hours. The longer spectral frequencies are also of particular interest with reference to the present invention because they reference states whose periods change corresponding to mood and emotion. An example of a physical cardiovascular adaptive process whose duration is over minutes is the decrease in heart rate variability that occurs during types of physical exercise. As the heart beats more rapidly during exercise, the inter-beat interval becomes shorter. This is paralleled by exercise-induced decreases in pulse and blood pressure variability, along with an increase in absolute values of pulse and blood pressure. TABLE 1 shows Frequency Spectrum of Heartbeats and their Cycles.

TABLE 1

| FREQUENCY | HZ CYCLES PER SECOND | APPROXIMATE LENGTH OF CYCLE | RELATED BIOLOGY |
| --- | --- | --- | --- |
| ULF Ultra Low | <0.01 | 1 to 23+ hours We use 1 to 5 hours. | Central (brain) mechanisms Moods, consciousness |
| VLF Very Low | 0.01-0.04 | 4 to 9 minutes | Temperature regulation Hormones-Renin & Angiotensin |
| LF Low | 0.04-0.15 | 35 seconds to 4 minutes | Sympathetic (Parasympathetic) Blood pressure |
| HF High | 0.15-0.4 | 4 seconds to 35 seconds | Parasympathetic Respiratory modulation of Vagus Nerve |
| VHF Very High | 0.4-0.8 | 1 second to 4 seconds | Rapid respiration Exercise Sleep apnea |

An example of an adaptive process over long time periods is the changes in HRV that occur during the course of a night's sleep. Changes in HRV patterns occurring during sleep are related to the various phases of sleep (dream sleep=REM, deep sleep=Phase 4). Of particular interest are frequency domains of HRV occurring over minutes to hours, i.e., VLF and ULF. VLF and ULF frequencies range from minutes to hours, corresponding to behavioral patterns lasting the same amount of time. The time frames of these longer frequencies correspond with emotional states as well as with moods. These longer frequencies also correspond to mental states, with the more than 85% of the entire frequency spectrum of HRV in the ULF frequency range. The inventor determined that these longer frequencies represent centrally-acting mechanisms reflecting either adaptive or maladaptive behavioral patterns. HRV, therefore, is a holistic measure of neurocardiac integration, affected by both mental and physical processes.

Another physiological measure that has been well-studied is motor activity. Like heart rate, it oscillates with periods whose cycles are measured in fractions of seconds, minutes and hours. Motor activity can be measured by movement accelerometers, called actigraphs. Recording of movement over 24-hours has revealed systematic differences in spatial-temporal structures of activity. A system using data from one actigraph is disclosed in U.S. Pat. No. 6,241,686 (Balkin et al.—2001).

An accelerometer is a device that produces an electrical output (i.e. charge, voltage, current or change in resistance that is proportional to the acceleration to which it is exposed.

Modern accelerometers are typically micro-machined silicon sensors that are based on the detection of the displacement experienced by a small mass linked to a frame by beams when the sensor is subjected to acceleration: the applied force, hence the acceleration, can be derived from the measure of the deflection. An estimate of the energy expenditure is produced from the derived parameters, through algorithms specific for every system. Numerous commercial and experimental systems use these sensors embedded in small sized portable microprocessor-based devices, to detect movement and to digitally record parameters derived by the acceleration signal produced by the changes in body position.

Piezo-resistive and variable capacitance accelerometers, very frequently used in human movement applications, respond to accelerations due to movement as well as to gravitational acceleration. The static response of these accelerometers reflects the orientation of the accelerometer with respect to gravity and can be used to compute the angle relative to the vertical of the sensor and, consequently, of the body segment on which it is located. Since acceleration is a vector quantity, the sensitive part of the transducer is constructed such as to maximize the sensitivity of the sensor along one particular direction, while minimizing crosstalk due to the other acceleration components; one, two or three axis sensors are available in very compact arrangements. The most common parameters digitally derived from the transducer signal are: Threshold Crossing, TC: this is measured by recording a count each time the transducer signal crosses a defined threshold voltage regardless of whether the voltage is increasing or decreasing. Counts are then accumulated for each epoch and stored in the device's memory. Time above Threshold, TAT: this is obtained by summing the time that the signal exceeds a previously defined acceleration threshold. At the end of each epoch, the value is stored in the device's memory. Integrated Activity, IA: this is computed by summing the deviations from zero volts (i.e. the absolute value of the voltage) during the epoch and storing the value at the end of the epoch.

Actigraphs have been used to study psychiatric as well as physical conditions. In psychiatry, actigraphs have been used to examine disorders of children and adults. Children with Attention Deficit Hyperactivity Disorder (ADHD) have been studied using objective measures of their activity levels over a 24-hour period. The geriatric population has also been studied with actigraphy, with variability in movement differentiating healthy people from those who are demented. Actigraphs of other conditions, such as PTSD and Depression are distinguished from one another through use of actigraphs.

Actigraph measurements over spatial-temporal periods throughout the night have been used in studying children with sleep apnea. Sleep apnea may be thought of as abnormal spatial-temporal structuring of the ultradian rhythm of sleep due to impaired breathing. Actigraph variability has been used to diagnose and treat movement disorders, asthma, and to track normal and abnormal motor development.

Variability of movement is another complex metric, and it too, shows fractal organization. These two peripheral measures, heart and movement variance, reveal information about the functional coordination and organization of the brain/body system as it moves through time. These measures are orthogonal to each other in terms of variability, with heart rate showing the greatest variability during sleep, while movement variability is greatest during wakefulness. Quantitative study of these measures with linear and nonlinear tools, results in measurements that reveal stability and flexibility of an organism as it changes state to accomplish a task. The complexity of system organization (corrected for age and sex), along with the study of fractal patterns, characterize the system in terms of its health and vigor. The inventor has found that the spatial-temporal patterns of heart rate and movement with their variances, are fractal and each trace a shape, an envelope. Each envelope is separated by an energy barrier that must be overcome. Over the course of 24 hours, the variance patterns of heart rate and movement are sometimes complementary and sometimes orthogonal to each other.

A new class of devices have been developed that can not only detect and record activities, but can also classify them into clinically relevant movement (walking, running, climbing and descending stairs, etc.) and posture (standing, sitting, lying) classes, as a consequence of a number of studies researching the information content of accelerometric data coming from sensors attached to the trunk and limbs of subjects. These movement recorders consist of a set of transducers, usually accelerometers, located on the legs and the trunk, a portable recording unit and dedicated algorithms for off-line signal processing, very similar in function and structure to the EKG Holter type recorders. The signals produced by movement and posture are transduced and acquired by the recording unit, pre-processed and stored in high capacity memory cards. The off-line processing, which is executed after data downloading into a personal computer, PDA, or "smart phone" automatically identifies posture and movement.

Ambulatory Monitoring produces accelerometers where the acceleration is transduced by a tri-axial sensor, and sampled at 16 Hz; it can collect the data in several forms, and it can store it in two second epochs, as needed.

Body Media produces an accelerometer as part of a sensor package that also collects other physiological signals.

Currently available wireless monitoring systems use interfaces standard for these systems, i.e. GPS (1.2276 and 1.57542 GHz); Bluetooth=802.15 (2.45 GHz); 802.11, 802.11b, 802.11g (2.4 to 2.483 GHz) and 802.11a (5.180 GHz to 5.805 GHz). These interfaces have resulted in systems that are not easily worn on the body or in systems whose sampling rate is inadequate for nonlinear analysis. At least 1000 data points are necessary to begin to perform nonlinear analysis and many more data points result in even more accurate portrayal of the system.

Current hardware systems use technology that allows for high data sampling rates while using up large amounts of battery life. The resulting system is short on battery life or has slow speed of transmitting data, or is not easily worn on the body. Bluetooth, a current popular wireless transmission system is better designed for monitors meant for intermittent data acquisition, i.e., event monitors. Hardware for this invention needs monitors that capture data a high sampling rates (less than a second) and can do so continuously over a period of at least.

Qualitative maps are phase space portraits. State space is a vector space where the dynamical system can be defined at any point. Quantitative maps and charts track the physiological changes of the system, as well as showing its state transitions. From this information a spatial-temporal envelope is constructed.

Any of a number of physiological measurements may be used as long as they show amplitude and frequency variability over time. Examples of physiological parameters that may be used are electroencephalogram (EEG), electromyogram (EMG), temperature (thermister), oxygen saturation (oximeter), voice (vocal dynamics), glucose concentration (glucometer), metabolites in blood or saliva, electrical measures of muscle tone in the neck, pupillary size, eye movement, blood flow, postural sway, etc. The variances of each of these measures change over time, in more or less complex ways.

The measures can be compared by cross-correlation function, among other methods. Cross-correlation is a method by which two sets of numbers can be quantified. It is based upon the fact that if a point by point multiplication of two data sets is completed, the sum of the products will be a quantification of their relationship.

Nonlinear tools, such as Poincare maps, Approximate Entropy, Visual Recurrence Analysis, Lyapunov Exponent, Fractal Dimension, Mutual Information, Correlation Dimension, Detrended Fluctuation Analysis, Wigner-Ville, Hilbert-Huang Transform and Signal Decomposition Analysis, etc., reveal the spatial-temporal structure of the system, along with its organization, complexity and adaptive capacity.

A Poincare map (also called first recurrence map) is the intersection of a periodic orbit in the state space of a continuous dynamical system with a lower dimensional subspace. This is called the Poincare section, transversal to the flow of the system. More precisely, one considers a periodic orbit with initial conditions on the Poincare section and observes the point at which this orbit first returns to the section, thus the name first recurrence map. The traversality of the Poincare section means that periodic orbits starting on the subspace flow through it and not parallel to it. The Poincare plot has been used as a quantitative measure, as well. FIG. 4 reveals quantitative Poincare for heart rate variability analysis over a period of time (1500 ms in this case). This is prior art. The long axis of the Poincare shows the long range correlation of the signal over the period for which the recording was made, while the short axis indicates short term correlations in the data set.

The Poincare diagram itself, as shown in FIG. 4, is the second moment of a distribution of points in a plane. For heart rate variability, this figure is a vertical cross section through the heart rate attractor, the attractor being a torus (bagel). This diagram is a quantitative Poincare used for heart rate variability analysis. The x-axis is the r-r-interval of the time series, while the y-axis is the r-r-interval plus one. Both axes have milliseconds (msec) of heart rate as their units. The centroid is the region with the largest collection of r-r-intervals of a particular frequency. Standard descriptors of heart rate variability are those of short-term variability, i.e., STD1, and long-term variability; STD2. The variances corresponding to short term heart rate variability are due to decelerations and accelerations of heart rate. The upper part of the diagram represent longer heart beats, and therefore decelerations of heart rate, while the lower parts corresponds to shorter heart beats and therefore, accelerations. The maximum thickness of Poincare slice represents the short term variability range of the segment being studied, while W represents the maximum thickness of the distribution of heart rate variability round the centroid. The double pointed arrow represents the long term variability of heart beats over the entire segment that is being studied.

Visual Recurrence Analysis is a graphical program, both qualitative and quantitative, that detects hidden patterns in dynamical data, and helps to find nonlinearities in data. It has been proven mathematically that one can recreate a topologically equivalent picture of the original multidimensional system behavior by using the time series of a single observable variable the basic idea is that the effect of all the other (unobserved) variables is already reflected in the series of the observed output. Furthermore, the rules that govern the behavior of the original system can be recovered from its output. In Visual Recurrence Analysis, a one-dimensional time series from a data file is expanded into a higher-dimensional space, in which the dynamic of the underlying generator takes place. This is done using a technique called "delayed coordinate embedding," which re-creates a phase space portrait of the dynamical system under study from a single (scalar) time series. Visual Recurrence Analysis provides qualitative and quantitative assessment, and nonparametric prediction of nonlinear and chaotic time series. Mutual Information, Correlation Dimension, False Nearest Neighbors, Recurrence Histogram and spatial-temporal entropy methods to determine the optimal values of embedding dimension and time delay for delayed coordinate embedding.

Visual Recurrence Analysis=VRA, is thus a method for quantification of the recurrence properties of systems with nonlinear dynamics using graphical representations as well as statistical analysis. The first example using VRA is the graphical representation of white noise=$1/f^{beta}$, where beta=0, is shown in FIG. 5A (left). White noise is considered to be random, having equal spectral power at any frequency, i.e., a flat frequency spectrum in linear space. Brown noise, or Brownian noise=$1/f^{beta}$, where beta=2 is shown in FIG. 5B (right). Brown noise is a random walk. These two types of noise have specific mathematical properties.

A healthy heart has correlated patterns of heartbeats that are mathematically between white noise and brown noise. FIG. 6 represents the Visual Recurrence Analysis=VRA, for heart rate variability (HRV) of a person with a healthy heart. It is clear from FIGS. 5A, 5B and FIG. 6 that heart rate variability presents a recurrence plot organized between that of white noise, and brown noise. VRA of HRV is thus $1/f^{beta}$. Where beta is greater than 0 and less than 2.

The Lyapunov Exponent is a measure of unpredictability (predictability) of a time series. It gives the rates of divergence and convergence in a chaotic attractor. A chaotic attractor has both convergence and divergence, and any two trajectories will not only diverge, but come back to within an infinitesimally small distance of each other and do so an infinite number of times. The averaged rate of divergence (or convergence) is measured for two neighboring trajectories. Actually there is a whole spectrum of Lyapunov exponents. Their number is equal to the dimension of the phase space. If one speaks about the Lyapunov exponent, the largest one is implied. It is important because it determines the prediction horizon. Even qualitative predictions are impossible for a time interval beyond this horizon. It is given by $$\lambda = \lim_{t \to \infty} \frac{1}{t} \ln \frac{|\delta Z(t)|}{|\delta Z_0|}$$

where is the error of the measurement of the initial state. Here, the error is given in units of the averaged amplitude of the non-periodic oscillation. The Lyapunov characteristic exponent gives the rate of exponential divergence from perturbed initial condition noise (random walk).

Detrended Fluctuation Analysis provides a method for quantifying the correlation property in non-stationary time series based on the computation of a scaling exponent "d" by means of a modified root mean square analysis of brownian motion (a random walk). To compute d from a time-series, like the interval tachogram, the time series is first integrated. Next, the integrated series is divided into boxes of equal length and the least-square line fitting the data in each box is calculated. The integrated time series is detrended by subtracting the local trend and the root-mean square fluctuation of the detrended series is computed. If log F(n) increases linearly with log n, then the slope of the line relating F(n) and n in a log-log scale gives the scaling exponent d. d is related to the "1/f" spectral slope=If d=0.5, the time-series x(i) is uncorrelated (white noise). If d=1.0, the correlation of the time-series is the same of 1/f noise. If d=1.5, x(i) behaves like Brownian noise. This computation is repeated over all time scales (box sizes) to provide a relationship between F(n) and the box size n. Typically, F(n) will increase with box size n. A linear relationship on a double log graph indicates the presence of scaling (self-similarity) where the fluctuations in small boxes are related to the fluctuations in larger boxes in a power-law fashion. The slope of the line relating log F(n) to log n determines the scaling exponent (self-similarity parameter).

Fractal Dimension measures how complicated a self-similar figure is. To understand a fractal dimension, one must understand what a fractal is. As discussed earlier, a fractal is a repeating, iterated, mathematical formula that produces a geometric pattern: an irregular or fragmented geometric shape that can be repeatedly subdivided into parts, each of which is a smaller copy of the whole. Fractals are objects in space or in time, that represent the pattern that the nonlinear system takes over the time under study. A fractal is infinitely complex, and self-similar under varying degrees of magnification. In effect, it possesses symmetry across scale, with each small part replicating the structure of the whole. Fractals can have their own dimension, called the 'fractal dimension,' which is usually a non-integer dimension greater than its topological dimension, and less than its Euclidian dimension. A fractal dimension is between a point and a plane. Fractals are used in computer modeling of natural structures such as clouds, and of biological structures such as the system of blood vessel within the body. Fractal dimension is a measure of how "complicated" a self-similar figure is. The fractal dimension is a statistical quantity that gives an indication how completely a fractal appears to fill space, as one zooms down to finer and finer scales. These fractal patterns can be measured quantitatively, discriminating between health and disease, as well as discriminating one condition from another.

Sometimes, it is possible to diagnose a pathological condition through study of variability in a single physiological parameter. An example of single parameter variability is the spatial-temporal envelope of temperature variability that characterizes relapsing malaria. However, the majority of physiological and psychological disorders need two or a maximum of three physiological measures with descriptions of their envelopes, for precise and accurate diagnosis. According to Taken's Theorem, all nonlinear biological systems can be accurately characterized through study of the variability of a maximum of three physiological measures. Taken describes a technique for extracting an estimate of the controlling variables from a time series of data which appears random. This technique works even when the descriptive equations are completely unknown. The result is that a hidden state of multi-dimensional dynamical system can be reconstructed from measurements of a scalar value (a time series of a physiological signal). A fractal is a repeating geometric pattern is an irregular or fragmented geometric shape that can be repeatedly subdivided into parts, each of which is a smaller copy of the whole.

Emergence is an important aspect of the behavior of a nonlinear biological system. The behavior of the overall system cannot be found by summing the behaviors of its constituent parts, and thus the whole system is greater than its parts! Emergence arises within the system during the process of self-organization, producing novel and coherent structures whose patterns and properties have boundless complexity. An example of emergence is the evolutionary phenomenon of vision. Vision, with all of its complexity, could not be deduced or predicted from the (levels below itself), such as wavelengths of light. Complexity emerges within the system through adaptive self-organization of iterated patterns in response to task performance. Complexity cannot be predicted from its component parts, yet emerges through self-organization of the system. Self-organization is due to emergent features of multiple agents following their own local laws. Emergence reduces entropy as it creates order out of chaos. The phenomenon of emergence is widespread, from galactic super clusters to all forms of life (bird flocking), etc. When dynamical systems show a combination of small scale order (local attractions) and large scale disorder (uncorrelated over distance), the patterns that result are emergent. Order (temporal ordering) within a system is information. The complexity of a system can be classified by how much information is needed to describe it. Local interactions can give a dynamic structure to the system which can cause the emergence of unexpected features. These features are not predicted by traditional entropy considerations for they are too improbable. During transitional states, the system has more degrees of freedom (is more chaotic) as it explores novel spaces. Novelty can be seen as an increase in dimensionality. New emergent variables explore expanded state space during transitions. State space expands continually as these innovative combinations (new building blocks) occur, and therefore maximum entropy also expands. When the system finds a more adaptive, persistent and relatively more stable state, self-organization has occurred, the system has fewer degrees of freedom and entropy is lowered locally.

As part of this invention, important information about adaptability and flexibility is revealed through study of acceleration (or deceleration), i.e., "rate of the rate of change". Accelerations and decelerations are measured as the system transitions between states, and they correspond to adaptability and flexibility within the system. When measurements from several physiological signals are made over time, the health of the system is revealed, along with its ability to adapt to stress. Study of these patterns and the rate at which these patterns change, individually and collectively, provide quantitative information as to whether the system is moving toward health or toward disease. The inventive software uniquely traces the shapes of these spatial-temporal patterns tracked over time. This software employs both linear and nonlinear mathematical tools in the analysis of one or more simultaneously collected physiological signals, along with their combinations of the signals, to distinguish the spatial-temporal patterns characteristic of each psychiatric and physical condition. The complexity of these patterns along with their transition times from and to another pattern, make up a coordinated complex system, one that gradually becomes less organized and less structurally complex, as the system ages.

The invented software describes these patterns from the beginning of life to death, for both males and females, to provide quantitative maps to chart the developmental and gender-specific changes that form a "corridor of health." The unique analyses used here reveals precise information about system state at any moment in time, showing whether the system is healthy or diseased. These analyzed patterns also accurately predict evolving pathological conditions, and they serve to predict cataclysmic events such as epileptic seizures, and even sudden death. Appropriate treatment, by whatever means, moves the system to a healthier adaptation, as reflected in its variability measures. The claims speak to the analysis of these easily collected peripheral measures in diagnosing, monitoring and tracking effective treatment of physical and psychiatric conditions.

Results from these measures may be quantified in numbers or in pictures (in state space), in sound (sonificiation) or in dynamically moving images (movies), with or without words, thus readily communicating information about the system to groups of people of all ages, even to those who don't speak the same language. For example, icons representing Poincare plots could be used as templates in a cardiac defibrillator, transmitting precise cardiac care data to guide treatment without reliance on verbal language (airports, space station, deep sea divers, etc.).

As previously mentioned, PTSD patients show dysregulation of their autonomic nervous system that is even seen in the resting state. PTSD patients show dysregulation of their autonomic nervous system, with loss of flexibility in adaptation to ordinary stress, as measured by (1) significant reduction in heart rate variability (iterated interbeat intervals of heartbeats over time) and (2) significant reduction in variability in parasympathetic (vagal-tone) activity and (3) augmented sympathetic activity in comparison with non-PTSD controls.

SUMMARY OF THE INVENTION

It is an object of the present invention to determine the psychiatric and physical state/condition of a person, animal or other living thing, or population, accurately and effectively.

Another object of the invention is to determine the psychiatric and physical condition/state of a person, animal or other living thing in a precise, consistent and effective manner.

Yet another object is to provide a method for processing spatial-temporal patterns of a person's or animal's physiology to determine that person's or animal's psychiatric state, psychological state and physical state/condition.

It is still a further object to provide hardware for processing spatial-temporal patterns of physiological inputs to determine the psychiatric and physical state/condition of a person or animal.

Yet still another object of the invention is the provision of software for determining the psychiatric and physical state/condition of a person or animal by monitoring physiological inputs of a living being.

A further object of the invention is to provide a procedure for diagnosing the psychiatric and physical health of a person or animal through the being's peripherally collected non-specific physiological outputs.

It is also an object to provide means for defining treatment modalities of psychiatric and physical disorders in an accurate, effective, reproducible and efficient manner.

Yet a further object is the provision of methods and products for processing physiological inputs of a person or animal to measure effects of treatment (pharmaceutical, somatic and therapeutic, or alternative treatments, etc.) of psychiatric, psychological and physical disorders of a person.

Another aspect is to provide software for processing spatial-temporal patterns of physiologic inputs to obtain data relating to different psychiatric, psychological and physical conditions.

A related objective is to provide means for qualitative and quantitative measuring of changes in the psychiatric, psychological and physical conditions with treatment thereof.

A further objective is to provide software for automatically analyzing data obtained from spatial-temporal patterns of physiologic inputs to determine the unfolding of psychiatric and physical conditions.

An additional objective is to provide a method for analyzing collected data relating to psychiatric and physical conditions. This data is obtained by processing through a software program that processes spatial-temporal patterns of physiologic inputs to validate acceptability of software algorithms and provide a screening or preliminary assessment of an examined being's diagnosis and treatment efficacy measures, either in real-time or elapsed time.

It is a further objective of the inventor to provide equipment for healthcare professionals including psychiatrists, psychologists, cardiologists, oncologists, physiatrists (M.D. rehabilitation specialists), and other physicians, as well as medical and biological researchers, physician's assistants, nurse practitioners, social workers and other health practitioners, such as physical therapists, chiropractors, including others involved in health maintenance, such as yoga and exercise instructors, massage therapists and others, as well as agencies monitoring health, insurance companies, employers, educators and laymen concerned with exercise physiology and wellness, to measure specified physiological parameters. The purpose may be diagnoses of psychiatric and physical health and illness and changes therein before, during and after any treatment, for an individual or group. Other interested parties include law enforcement and security personnel, industrial personnel, government and international monitoring personnel, including those on earth, and animals, people and plants and other living beings in extraterrestrial environments, requiring accurate communication and response, sometimes without a common language.

Another objective of the invention is to provide data expression as either quantitative or qualitative icons and/or numbers or language-based or sensory or motor (or other modality) readouts for expressing many conditions understandable by either trained professionals or laymen of all ages and educational levels, including animals, plants and other living beings involved in experiments.

Yet another object is to provide equipment for simultaneously measuring and recording one or more physiological data streams as a single plot or several plots for comparative purposes and for use for a specific purpose that is dependent upon physiological data inputs, for both research and commercial applications in order to track the entire system as it moves through time.

A still further and related object is to provide equipment for simultaneously recording heart rate variability and movement variability, (as well as any other physiological measure) onto a single time-series plot, or as several plots, that are compared to each other and can be converted to normalized units for consolidation, and/or further comparisons, one time series to another.

Another object is to provide data expression that shows the patterns that a biological system takes as it moves through time using both linear and nonlinear analysis. Linear analysis alone doesn't differentiate the ordering of a set of intervals with their variability from a randomly mixed set of the same intervals. An object of this invention is nonlinear analysis that results in animation of sets of intervals of one or more physiological measures to reveal both short and long term correlations in the time series, as well as additional mathematical properties of the time-series, individually, and taken together.

These and other objects will become apparent from the discussion to follow and from the appended claims.

As explained earlier, the nonlinear system comprised of brain and body yields a holistic output, moment by moment, in response to environmental input. The brain/body system is self-organizing and continuously adaptive. The system produces patterns of response that are iterated, with each new pattern dependent upon the previous one taken by the system, making the entire system and the adaptation of the living being measurable, and showing short term predictability.

The present invention in a preferred form involves measuring one or more physiological signals, such as heartbeat and movement, simultaneously over time, to determine the spatial-temporal organization of these physiological patterns, and their linear and nonlinear characteristics.

Pursuant to a preferred form of the present invention, the organization of these patterns and the rate of change from one pattern to the next, as calculated from each of their variances, can be determined by measuring heart rate variability and movement variability, along with other varying physiological parameters.

The invention provides a method and a system for achieving the above objectives by simultaneously measuring one, and preferably two or even three or more physiological parameters, simultaneously collected—the preferred measurements in most cases being heart rate variability and movement variability (voice variability, glucose and other metabolic variabilities, oxygen variability, temperature variability, etc.), and the rate of change of variability in each signal and the accelerations or decelerations of these changes in relation to measures from healthy (age and sex matched) people, animals, plants and other living things, and in comparison of each measure to another. This is easily achieved when measurements are taken from a period of milliseconds, to minutes to a longer period of time—up to 24 hours, or even longer (for patterns with even longer frequencies). The 24 hour collection time allows for delineation of the algorithms providing a normal corridor of health (of variability), developmental, age and gender specific, that may be used to contrast normal, and healthy with altered and pathological conditions. Two minutes is classically taken as the common lowest limit of collection time for most physiological signals because nonlinear analysis requires at least 500, preferably 1000 data points to meet minimum requirements for a data set for nonlinear analysis. Pattern reconstruction from a signal requires the signal to be sampled at a frequency at least twice its normal period. Twenty-four hours is usually the maximum time required to provide all the information necessary to study these patterns in depth, with occasional longer time frames up to months. Once these patterns have been delineated, shorter times of signal collection can yield valuable information, and the measurements can easily be processed in (effectively) "real-time," comparing the data with algorithms for specific purposes. With respect to heart rate variability for psychiatric illness, for example, the variance of interbeat intervals (R-R intervals) are measured. Particular interest is given to delineation of very low and ultra low frequencies for it is these frequencies (along with their spatial-temporal patterns) that correspond with the occurrence and duration of mood and emotional state (two minutes to several hours). These measurements are processed using a computer program, and the processed values can be compared to normal templates or converted into normalized units so that one signal can be directly related (added, subtracted, multiplied or divided) from a different one (i.e., variability in heart rate and variability in movement) to produce a derivative signal that elegantly describes system behavior. Likewise, movement (or other physiological) variability is measured, through calculations of variability in longitudinal and transverse acceleration, or variability in a gyroscopic accelerometer, worn on the body.

The invention provides a method and systems and apparatus for collecting physiological data and giving feedback in "real-time." This can be achieved by template matching, and/or with ongoing software calculations, with appropriate notifications and alarms for specific values of data sets.

The invention provides a hardware system that is ambulatory, wireless and effortless to wear, and is capable of storing several ambulatory physiological monitoring devices that can record for long periods of time (at least 24 hours). The physiological measurement devices can include a Holter (heart rate) monitor, movement monitor, temperature monitor (skin/or core), brain wave monitor (EEG), voice monitor, galvanic skin monitor, metabolic monitors including glucose, oxygen, saliva, etc.).

The invention provides non-invasive and ambulatory system hardware that has high sensitivity, high accuracy in data acquisition, and a high collection rate for each measure in fractions of a second, or other time segments, dependent upon the data required.

The information is retrievable, immediately or in the future, and the invention provides a hardware collection storage method that is lightweight and portable and provides data storage on digital media.

The invention provides for portable, and real-time analysis of part or all of the data for the ambulatory device with universal connectivity through a wireless radio, PDA, "smart" phone or land-line phone, laptop or desk computer, wristwatch or similar wearable device that provides basic analysis for the desired task, and gives appropriate template matching.

It is the intent of the inventor to produce and customize the hardware specific for each application. For example, a specialized vest or shirt with the wireless equipment is part of this invention. Alternatively, the wireless equipment may be affixed to the body with tape or other method of wave conduction, specific for that purpose, or may be made waterproof or childproof, and tamper proof, when needed.

It is the intent of the inventor to produce hardware that has low power use of a battery, or other power source, yet can transfer data at high speed and accuracy. These requirements being met, allowing physiological data to be collected in real-time, with short latencies, for essentially immediate processing and feedback, as appropriate.

The invention provides for the ideal insulated electrode that has little interference and can send a signal without direct skin contact if needed. The invention provides for unobtrusive monitoring, with signal transmission through clothing, or animal hair and skeleton, from lightweight portable monitors.

The invention provides the necessary wireless interface. Media Access Control (MAC), for example is a commercially available rapidly conducting wireless radio system that uses a 1 Mbps radio. Since more than half the volume of the entire wireless system is taken up by the battery, a very low power transceiver, consuming less than 10 mA in transmission mode (1 Mbps) and 22 mA in receiving mode is useful and necessary.

It is provided by this invention that connectivity is made universal through use of interfaces that include USB, Wi-Fi and Ethernet. QUASAR, for example, produces both the sensor, as well as an ultra-compact, low-power wireless sensor node, called Eco, a system smaller than a dime for each sensor. In this manner multi-parameter linear and nonlinear analysis of several simultaneously collected physiological signals such as EKG, movement, oxygen, glucose monitoring, EEG, etc. can be collected in real-time, analyzed with very short latencies, and adapted to a variety of medical, psychiatric, research and general health and developmental issues of living beings.

The invention provides the hardware upload and analysis that can be completed at a remote location such as a computer terminal and sent back to the appropriate personnel, completely analyzed, in digital format, in formats specific for the purpose such as mathematical data, iconic data, sonification data, etc.

Biological systems show nonlinear behaviors while functioning, these behaviors being especially obvious when the system has been perturbed and/or it is transitioning between states as it performs its tasks. It is the purpose of this invention to capture these behaviors over time, including the patterns of transition, to more fully describe both physical and psychiatric conditions, as well as to track changes due to interventions, growth or ageing. Classical linear tools analyze physiological signals in either time or frequency intervals (domains). Either time or frequency intervals can be mapped as a series of numbers, or diagrammed to show the area of space that is occupied by the time series data. Linear processing of the time series, as classically occurring as part of this invention, by sequenced intervals (R-R intervals or movement intervals, etc.), provide data sets whose underlying assumption is that variation between individual data points is random, and independent of past or future data points. Even given these (mostly incorrect) assumptions, linear processing has lead to some useful results, allowing comparison of data to a rich literature regarding these measurements. FIG. 7 is a flow chart for Processing Cardiac Signal from a Holter Monitor. The raw analog electrical signal from the EKG must be converted to a digital signal whose outcome is a valid R-wave data signal, now available for further processing. The software rejects spurious waveforms, and reclassifies others, keeping a temporal place for each waveform so that one physiological signal may be compared to another one, simultaneously collected.

Linear processing of a time series, gives data in a time domain data such as Statistics, Segmented Statistics. Regression Analysis, Histogram, etc. An example of linear processing of the cardiac R-wave is given in FIG. 8 Flow chart for Linear Processing of Heart Rate Variability. R wave data may be evaluated either as a space state portrait, a frequency spectrum or statistics may be performed on the time series.

Linear analysis of a time series, by frequency, produces the following graphs, among others: Spectral Analysis, Waterfall, Contour, Stacked Power, Power Spectral Density and Autoregressive Analysis. FIG. 9 represents Frequency Analysis of Heart Rate Variability. It is a flow chart for linear processing of heart rate variability in the frequency domain. The signal is processed and compared to age, and sex (gender) matched controls.

Linear processing of the time series by time intervals yields statistics about the system, whose mean, standard deviation, and even averaging by normalization, lose the temporal variations, and therefore the pattern, of the original physiological signal. Furthermore, linear measures do not differentiate between the ordering of an actual data set of the timed intervals from a randomly mixed pile of the same timed intervals. Nonlinear Analysis is needed to reveal the temporal organization of a data set of a physiological signal. FIG. 10 represents Physiological Data (Top) and Surrogate Data (bottom). Surrogate data does not contain the temporal ordering of the physiological time series, yet the two data sets are indistinguishable from each other using linear measures, left to right, i.e. heart beats, frequency distribution, histogram and auto-correlation frequency (function). The poincare plot, a nonlinear measure, is the first measure that is able to separate the real (physiological) time series from the bogus data set. Surrogate analysis is used for nonlinear data much as a t-test is run on linear data. This test is part of the invention.

Linear statistics cannot reveal the vibrant dynamics of living beings. Only through results derived from nonlinear data analysis can the difference between a biological time series and a random mix of the same timed intervals be made. Surrogate analysis shows the system to be nonlinear, where the temporal ordering of the signal readily distinguishes a biological system from a randomly ordered one. It is the temporal ordering of the physiological system that provides the information used in this patent.

Examples of nonlinear tools that examine the patterns made by a physiological time series are: Poincare maps, Visual Recurrence Analysis and Approximate Entropy.

Approximate Entropy—Entropy is a measure of change, first used to describe behavior of gases. In time a system will move toward equilibrium and homogeneity, corresponding to a state of maximum disorder and unchanging evenness. For a biological system, this is death of the system. Biological systems have constraints, i.e., boundary conditions that impose limits on their movement. Imposing limits on movement is called reducing degrees of freedom. As the system adapts, its specific boundary conditions restrict the state space of the constituents of the system, and thus compels the organization (self-organization) that results. Classically, entropy has been related to near-equilibrium states, yet biological systems are not close to equilibrium conditions. Non-equilibrium dynamics relate not to steady-state systems (a simplified special case) but to systems undergoing change, systems either on a transient (flow) towards equilibrium or away from it. Which direction the system takes depends upon driving forces. Strong energy input for example, will force the system far away from equilibrium. For such far-from-equilibrium systems, complex behaviors can set in; the stresses on the system become high and, like environmental stress, can cause breakdowns ("chaos"=hidden order) and jumps ("catastrophes"=abrupt changes of state moving over a boundary in system behavior. The system explores all possible ways to reduce the conflict, and self-organization to a more ordered state reduces the rate of entropy production and thus reduces stress. It can be shown that the greater the energy flow in such systems, then the greater the order (and information within the system). Energy flow becomes usefully employed by living organisms to do work in order to create (temporarily) higher-level 'material' structures (the set of chosen states perhaps being those which maximize entropy production).

The methods available depend upon the flexibility and complexity of interconnections within the system. Any system comprising a large number of parts allows a vast range of possible combinations. Within those combinations most will be disordered, yet many forms of order are also possible. The methods used to measure these system states include Detrended Fluctuation Analysis, Visual Recurrence Analysis, Correlation Dimension, Mutual Information, Wavelet transform, Wigner-Ville., Phase Space Portrait Analysis., etc.

Lyapunov Exponent—The Lyapunov characteristic exponent [LCE] gives the rate of exponential divergence from perturbed initial conditions. It is the averaged rate of divergence (or convergence) of two neighboring trajectories, as they move through time. Actually there is a whole spectrum of Lyapunov exponents. Their number is equal to the dimension of the phase space. If one speaks about the Lyapunov exponent, the largest one is meant. It is important because it determines the prediction horizon. Even qualitative predictions are impossible for a time interval beyond this horizon. It is given by $$\lambda = \lim_{t \to \infty} \frac{1}{t} \ln \frac{|\delta Z(t)|}{|\delta Z_0|},$$

where it is the error of the measurement of the initial state. Here, the error is given in units of the averaged amplitude of the nonperiodic oscillation.

Hilbert-Huang Transform with Signal Decomposition in a population of drug abusers is a current use of the invested software. The Hilbert-Huang Transform with Signal Decomposition is also used to diagnose and track developmental, normal and pathological conditions.

The patent, as well as the provisional patent, is built upon earlier experiment in which the criteria that defined a "healthy" subject were as follows: 1. Subjective report of "health." 2. No medical or psychiatric condition by history or examination. 3. No surgical history (in the past two years). 4. No medications, except commonly used vitamins. 5. No anxiety, as assessed by the Hamilton Anxiety Rating Scale and clinical interview. 6. No depression, as assessed by the Beck Depression Inventory and clinical interview. 7. No sleep disturbance as assessed by the Epworth Sleep Scale and clinical interview. 8. Detrended Fluctuation Analysis (DFA) supported the above health criteria. DFA has been previously reported as an identifier of healthy vs. unhealthy subjects. Each subject was instructed to engage in all usual activities, save for bathing. Following a brief medical history and physical exam the Holter monitoring equipment was placed on each subject. Digital Holter monitors were manufactured by one of two companies, Rozinn Electronics and NorthEast Monitoring. Both monitoring units were tested and found to be virtually identical in their outputs. Each company supplied software that allowed R-R intervals to be downloaded. Accelerometers by Body Media were placed upon each subject's dominant arm in order to verify sleep-time from wakefulness and to gather information regarding temperature rhythm, vertical and horizontal acceleration, and galvanic skin response.

BRIEF DESCRIPTION OF THE DRAWINGS

" FIG. 11 (left) represents the electrical excitation taking place over a single heartbeat, while FIG. 11 (right) delineates the R-R interval.

FIG. 20A (left) is heart rate variability, FIG. 20B (bottom right) is transverse (horizontal) acceleration and FIG. 20C (top right) is transverse acceleration plotted against horizontal acceleration.

FIG. 23 (left), shows that deep sleep has minimum entropy and FIG. 23 (right) shows maximum entropy during dream sleep visualized here as power spectral density plots of frequencies.

FIG. 25 (right), the same group of normal males, with their entropy during sleep, but now the depressed male has been treated and he is no longer depressed. He now fits into the corridor of health.

DESCRIPTION OF THE PREFERRED EMBODIMENT

Figure 1:
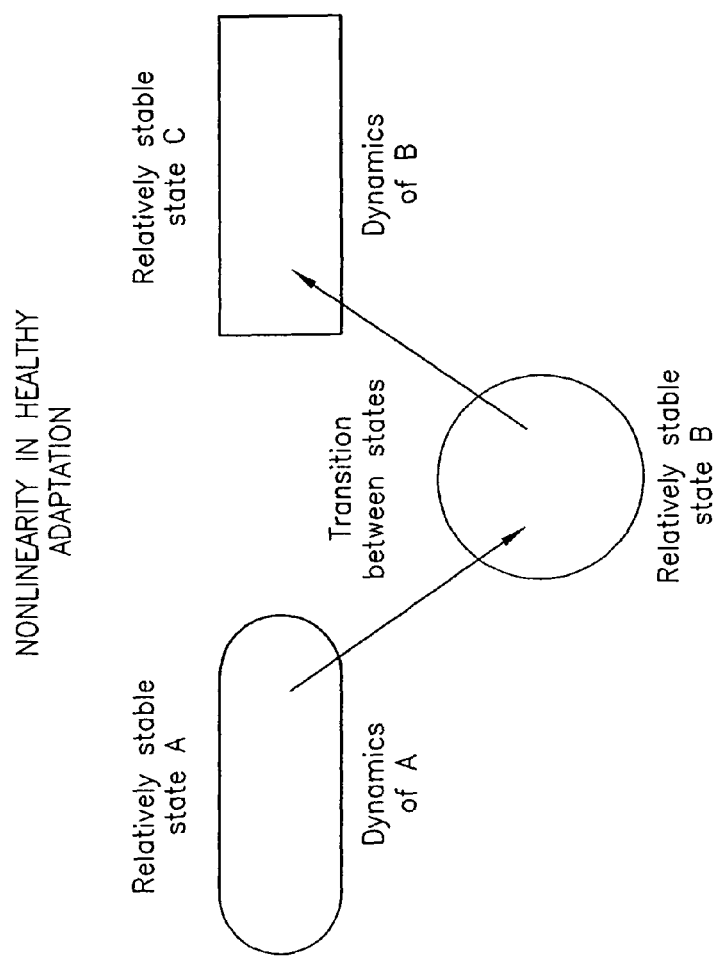
FIG. 1 is a schematic diagram of nonlinearity in healthy adaptation.
Figure 2:
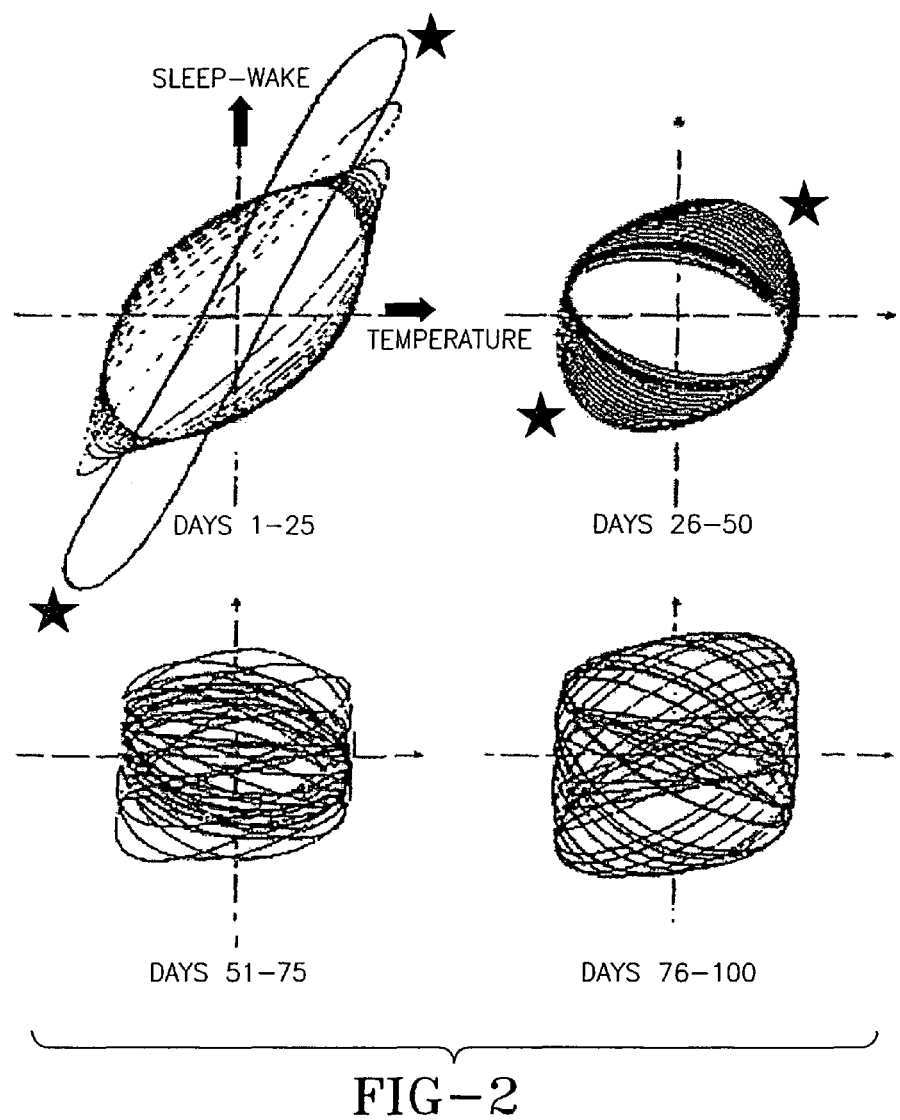
FIG. 2A-2D is a graphical representation of the pattern (in an animal) corresponding to that found in Jet-Lag.
Figure 3:
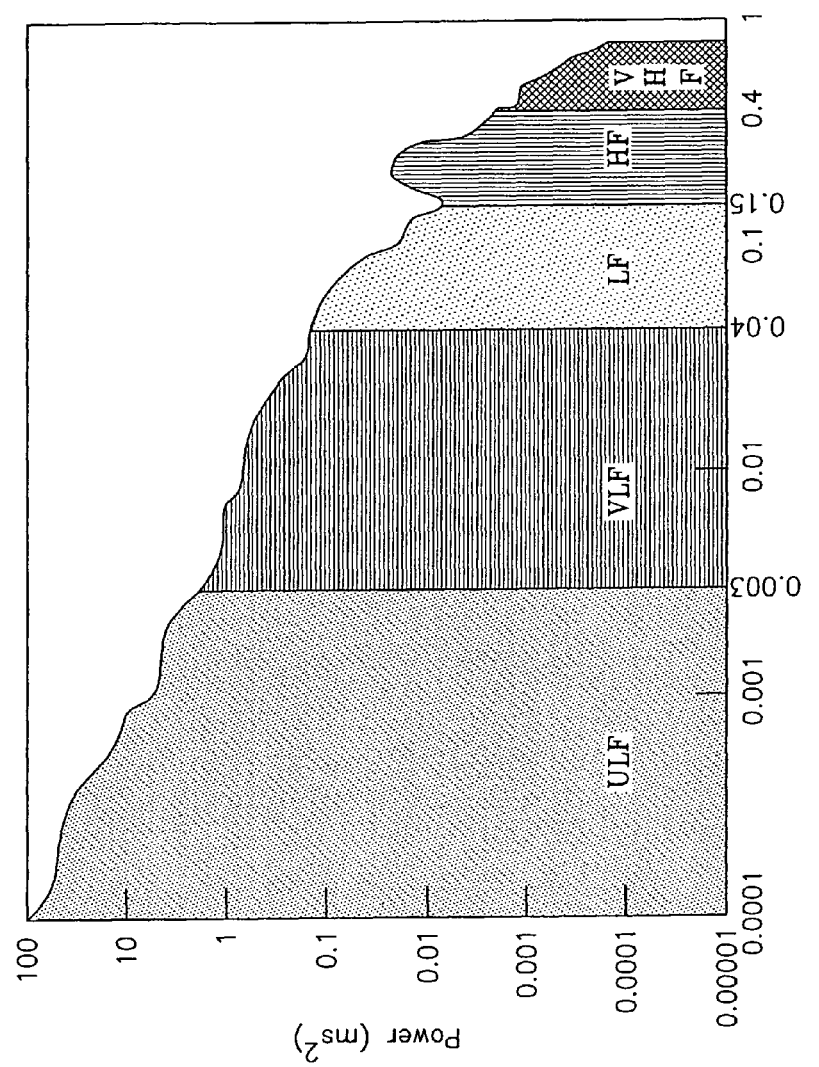
FIG. 3 is a graph representing the frequency spectrum for heart beats.
Figure 4:
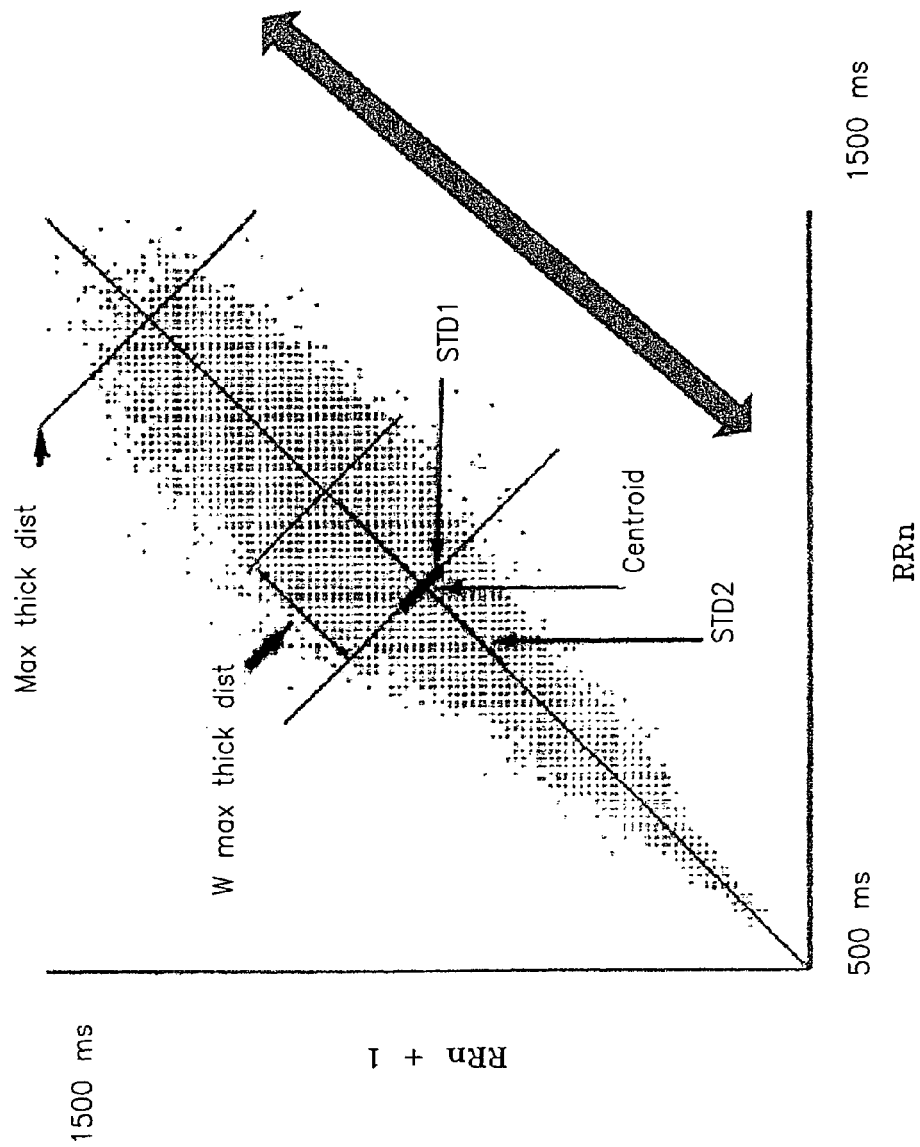
FIG. 4 is a graphical Poincare section for a first recurrence map of heart rate variability showing the intersection of the periodic orbit of the dynamical system of heart rate variability with a higher dimensional subspace, transversal to the flow.
Figure 5B:
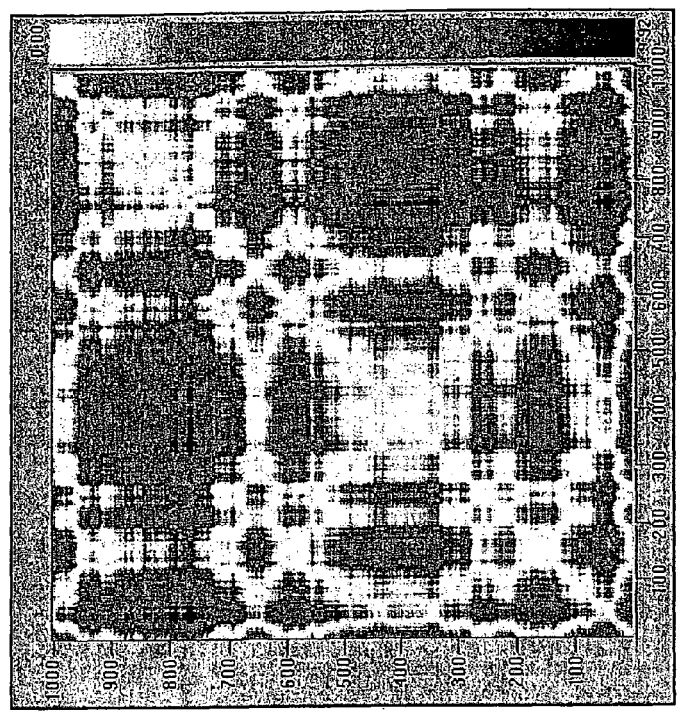
FIG. 5A (left). White noise is considered to be random, having equal spectral power at any frequency, i.e., a flat frequency spectrum in linear space. Brown noise, or Brownian noise=[1/F2] 1/fbeta, where beta=2 [and] is shown in FIG. 5B (right).
Figure 5A:
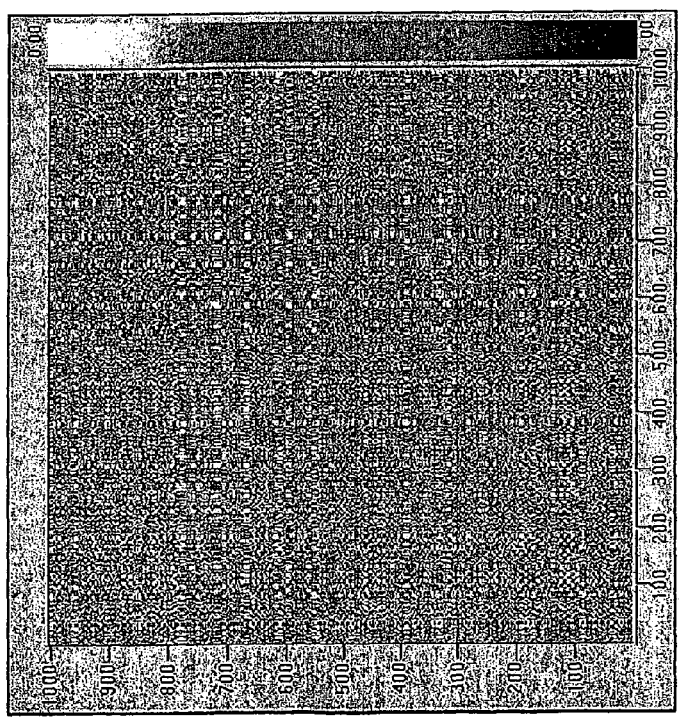
Figure 6:
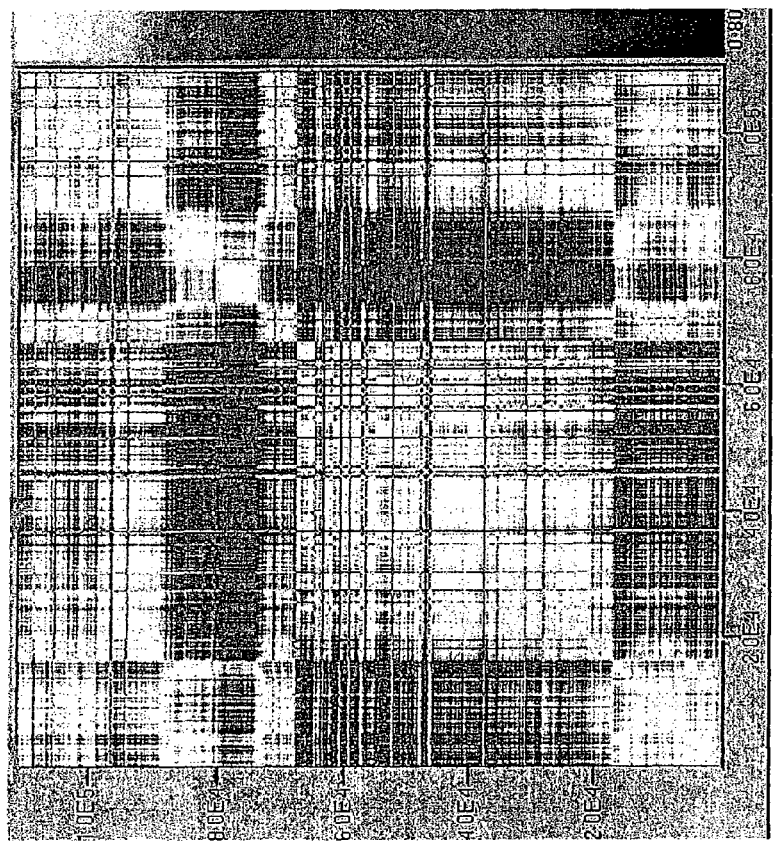
FIG. 6 represents the Visual Recurrence Analysis=VRA, for heart rate variability (HRV) of a person with a healthy heart.

The present invention is based on the understanding that people with dysregulated biological systems have mental and/or physical health problems, and people with mental and/or physical health problems have dysregulated biological systems. These people show alterations in their physiological reactivity during perturbation, as when they respond to stress. Looking at heart rate alone, altered pathologic reactivity under stress may fall into one of two main response patterns: high heart rate under stress, with over-reactive physiology or low resting heart rate and dampened response to stress with physiological under-reactivity. The invention relates to assessing psycho-physiological states and measuring and quantifying changes in reactivity using simultaneously collected peripheral physiological measures, each of which shows adequate variability within 24 hours. The software provided pursuant to the invention, taken together, provides a picture of the brain/body response to stress as well as the spatial-temporal alterations in reactivity. The invention in its preferred form measures both heart rate variability and motor or movement variability (and other physiological measures with their variability) assessed over periods up to 24-hour in duration using software and hardware specific for the purpose. Pursuant to the invention, the changes in spatial-temporal variation of heart rate and movement, along with their transitions during task performance, delineate the dynamics of healthy or maladaptive states. These variations track changes in states and their transitions that are also associated with improvements due to psychiatric, pharmacologic, somatic and/or other treatments. The invention is based upon a nonlinear systems perspective on adaptive processes in persons and other beings being examined.

The invention uniquely combines the measurement of linear and nonlinear parameters, revealing patterns with both short and long-term correlation, and the interaction of each physiological measure with the other. Each physiological measure is manifested uniquely dependent upon both age and gender. For each physiological parameter, for example, both amplitude and frequency of the signal over time, as well the organization and complexity of the measured parameter is made over the course of up to 24 hours (or longer). In addition, each measure is tracked in terms of system states, as well as description of its patterns and their quantitative changes during transitions. Rates of change of each measure are studied, for these indicate flexibility of the system to perturbation. Changes in velocity and acceleration to and from transitional states are measured and quantified. These calculations are completed for each of the simultaneously collected measures. Taken together, they reveal the stability as well as, the flexibility of the system. Healthy systems are both stable and flexible and are able to adaptively respond to environmental change. A nonlinear biological system oscillates between relatively stable states. Perturbation of the system may lead to epochs of instability in system performance, as the system adapts and finds a more stable state. These epochs, representing transitions between relatively stable states, are studied and measured according to the invention. The invention also tracks the spatial-temporal organization of one or more physiological measures of the system as it transitions from one state to the next. The invention further involves measurements of rate of change (acceleration or deceleration) of oscillatory behavior during transitions. In the case of multiple measures one parameter is compared to another. The invention additionally relates to measurement of the number (frequency) and size (magnitude) of transitions. The invention tracks changes in organization of the system (order/disorder). These measures taken within a given period of time indicate the capacity of the system to respond adaptively. At certain times, system oscillations are adequately described by simple, linear, mathematical functions, while at other times, the patterns produced during oscillatory behavior require nonlinear mathematical functions.

Pursuant to an example of the invention in its preferred form, heart rate variability and movement variability are measured simultaneously. After analyzing the heart beats and correcting for artifacts, the spatial-temporal structure of heartbeat data was evaluated using a custom software program. This program summed the heartbeat data as successive inter-beat times, detecting when the sum reached a predetermined time, and the variance was then calculated for that sequence of interbeat times. New variances for each of predetermined time period were calculated using a moving window with or without overlap. To get finer resolution of the data, the overlap was increased. Results yielded a sequence of variances based upon non-overlapping or overlapping periods of a predetermined time period of heartbeats updated at every fixed interval of time. A sequence of such updates of heart rate variances were taken over an extended period (up to the time of 24 hours). Heart rate variability may then be converted into normalized units for consolidated, rather than side by side comparison with a second physiological measure, for example, movement variability.

For example, heart rate variability was collected by a Holter monitoring device.

Figure 11:
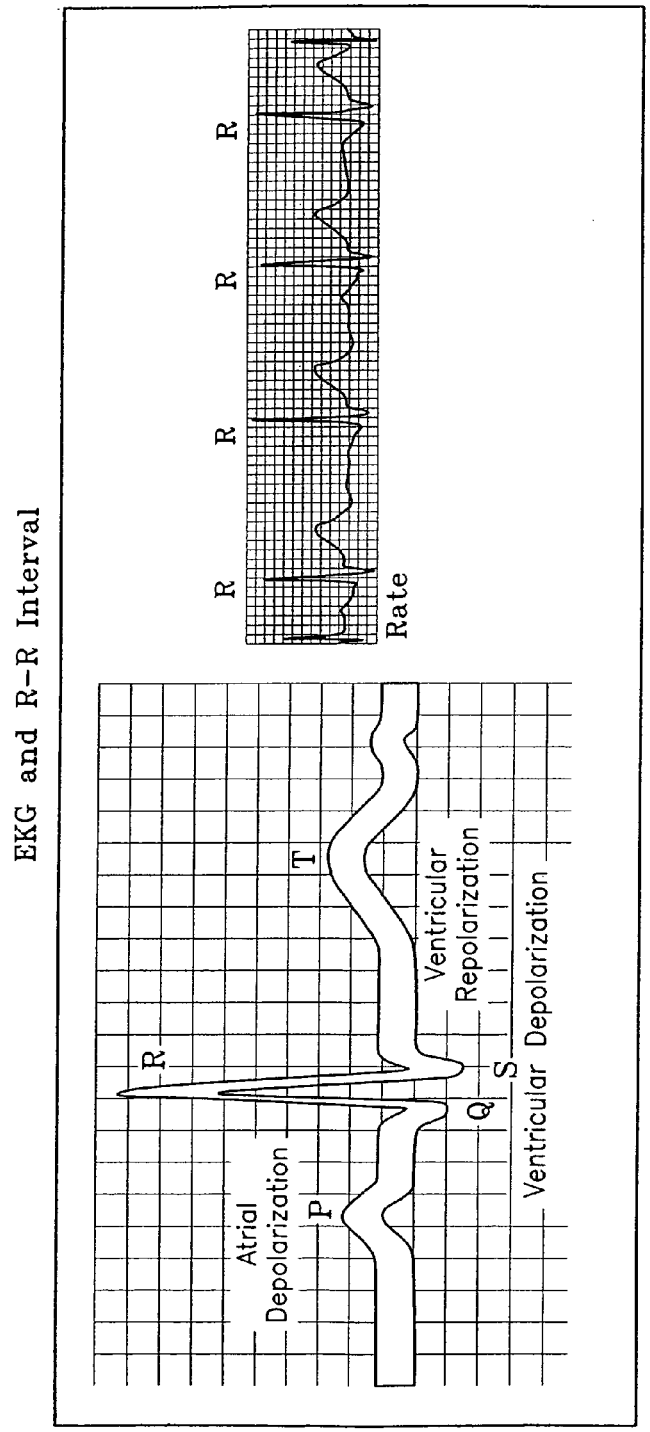
FIG. 11 (left) and 11 (right) are entitled "EKG and R-R Interval.

FIG. 11 (left) and 11 (right) are entitled "EKG and R-R Interval." FIG. 11 (left) represents the electrical excitation taking place over the duration of a single heartbeat. The p-wave represents the electrical depolarization of the atria, the two upper chambers of the heart that receive blood from the veins. The QRS complex is associated with the contraction of the ventricles (the lower chambers of the heart, while the T wave comes after the contraction in the relaxation phase of the cardiac cycle. This information is reported by the cardiac monitor, in milliseconds (y-axis) over time, and reported in seconds, i.e., on the x-axis. After examining the EKG, the interval between an R wave and the next R wave is measured in FIG. 11 (right). This is called the R-R interval.

Movement was sampled in time, and the variability of movement was measured using either a tri-axial accelerometer (gyroscope), or a bi-axial one (measures horizontal and vertical movements separately). In the case of the tri-axial accelerometer, movement variance was obtained using an actigraph, measured either at 'Threshold Crossing' i.e., "Zero Crossing"=recording of each count, (whether the voltage is increasing or decreasing), 'Time Above Threshold' (summing the time that the signal exceeds a previously defined acceleration threshold), or 'Integrated Activity' (summing the deviations from the absolute value of the voltage during the predetermined epoch).

Movement variability was similarly analyzed using a custom software program. Movement data obtained from the actigraph was analyzed using the same time restrictions used for heartbeat variance and collected at conceptually meaningful intervals (one second to five minute intervals). Minute-to-minute measurements of heart rate and motion variance were calculated with a custom software program using a predetermined certain time period. The results were also converted into normalized units for consolidated comparison to and for direct comparison with heart rate variability.

Figure 12:
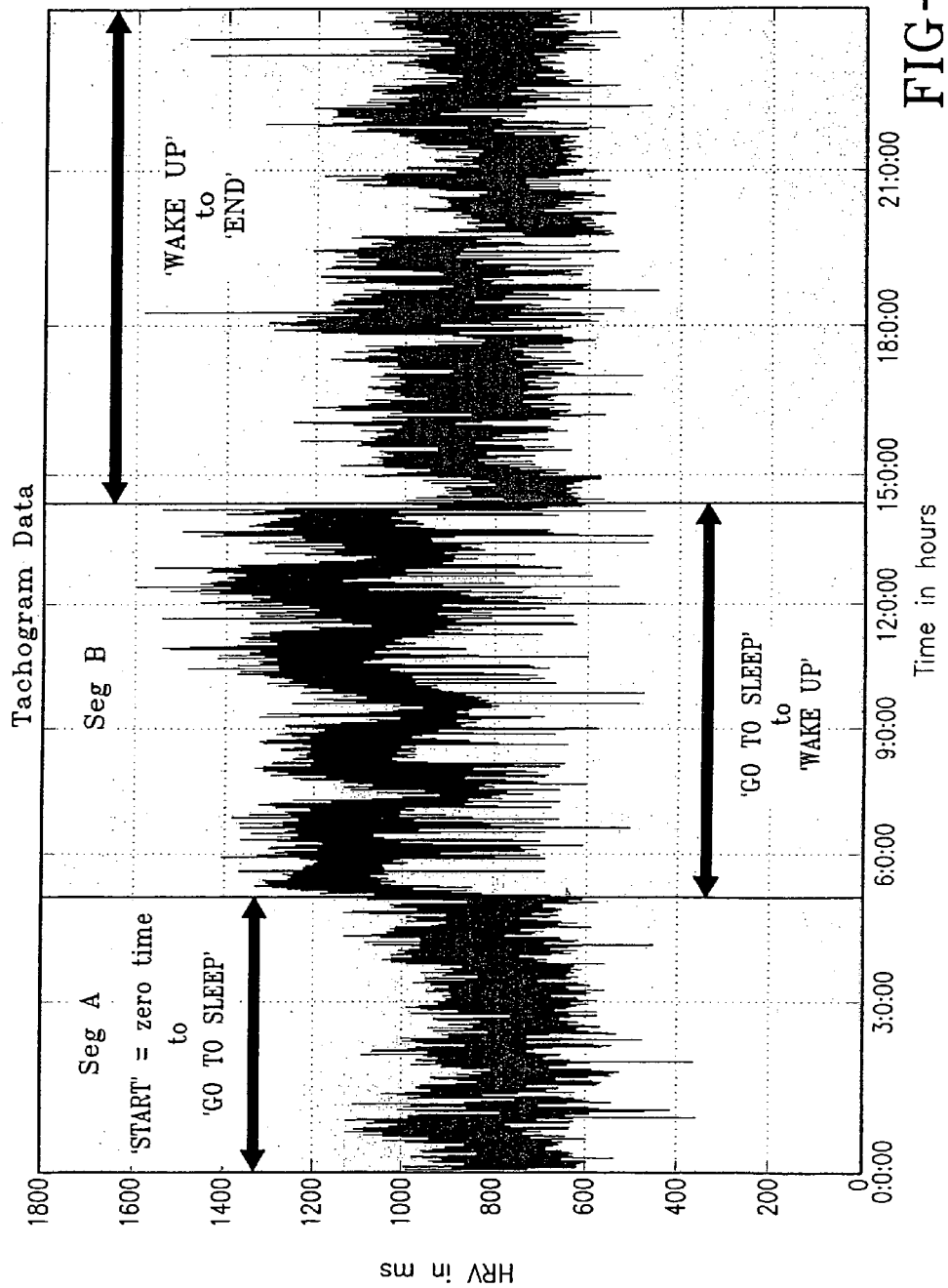
FIG. 12 is a tachogram of heart rate variability. This tachogram is a collection of 24 hours of R-R intervals from a healthy male.

The data obtained was plotted for the variances of both heart rate and movement. These measurements, collected over a time period up to 24 hours in duration, track change during both waking and sleeping states. To diagnose individual healthy conditions as well as disorders such as Sleep Apnea or Depression (each condition or disorder manifesting in a characteristic way according to gender and age), the time series was divided into three unequal segments for further analysis. The first waking segment at the beginning of the 24-hour recording is called 'SEG A'. SEG A represents elapsed time from the 'start-time', ('zero time'), the time at which the (heart, movement) monitoring equipment is placed upon the subject. The end of SEG A is just a heartbeat away from the onset of sleep. The point at which a person falls asleep is called 'go to sleep'. This point starts the sleep segment, 'SEG B'. SEG B represents the sleep segment, with its first measure the elapsed time from sleep onset, 'go to sleep' to 'wake-up.' The architecture of sleep, itself is found within SEG B. FIG. 12 is a tachogram. This tachogram is a collection of 24 hours of R-R intervals from a healthy male, showing how the segments are named.

The three sections have been visually separated, for clarity (standard procedure processes the entire tachogram).

The architecture of a single night of sleep of eight hours in duration, for example, contains shorter patterns of rhythms that correspond to each phase of sleep. Rhythms shorter than 24-hours in duration are called "ultradian." The entire sleep rhythm itself, as well as the internal rhythms delineating each sleep phase are also ultradian. Total sleep time, as well as sleep architecture, change in specific ways over the course of a lifetime, from fetal life through senescence. Examples of classically described, short ultradian oscillations contained within a night of sleep are 'dream sleep' (rapid-eye movement, i.e., REM sleep) and 'deep sleep' (also called "Phase 4" sleep), phase 1, phase 2, and phase 3 sleep. More recently, ultradian sleep rhythms have been described more simply, as 'quiet sleep', 'active sleep' and 'dream sleep'. The variances and organization of interbeat intervals for each sleep show recognizable patterns whose spatial-temporal structure is sex and age dependent. The remainder of the time to the end of the 24-hour monitoring period runs from 'wake-up' to 'end' (equipment taken off subject). This third segment is called segment C or 'SEG C.'. Here is also interest in transitions into and out of sleep, for these transitions reveal a measure of how flexible and adaptable the system is. For purposes of study, the segment that includes a few minutes before, through a few minutes after sleep is called segment D or 'SEG D'. The entire 24-hour segment is called 'SEG ALL'. Linear and nonlinear analysis is performed on each of these segments for each physiological time series.

Figure 13:
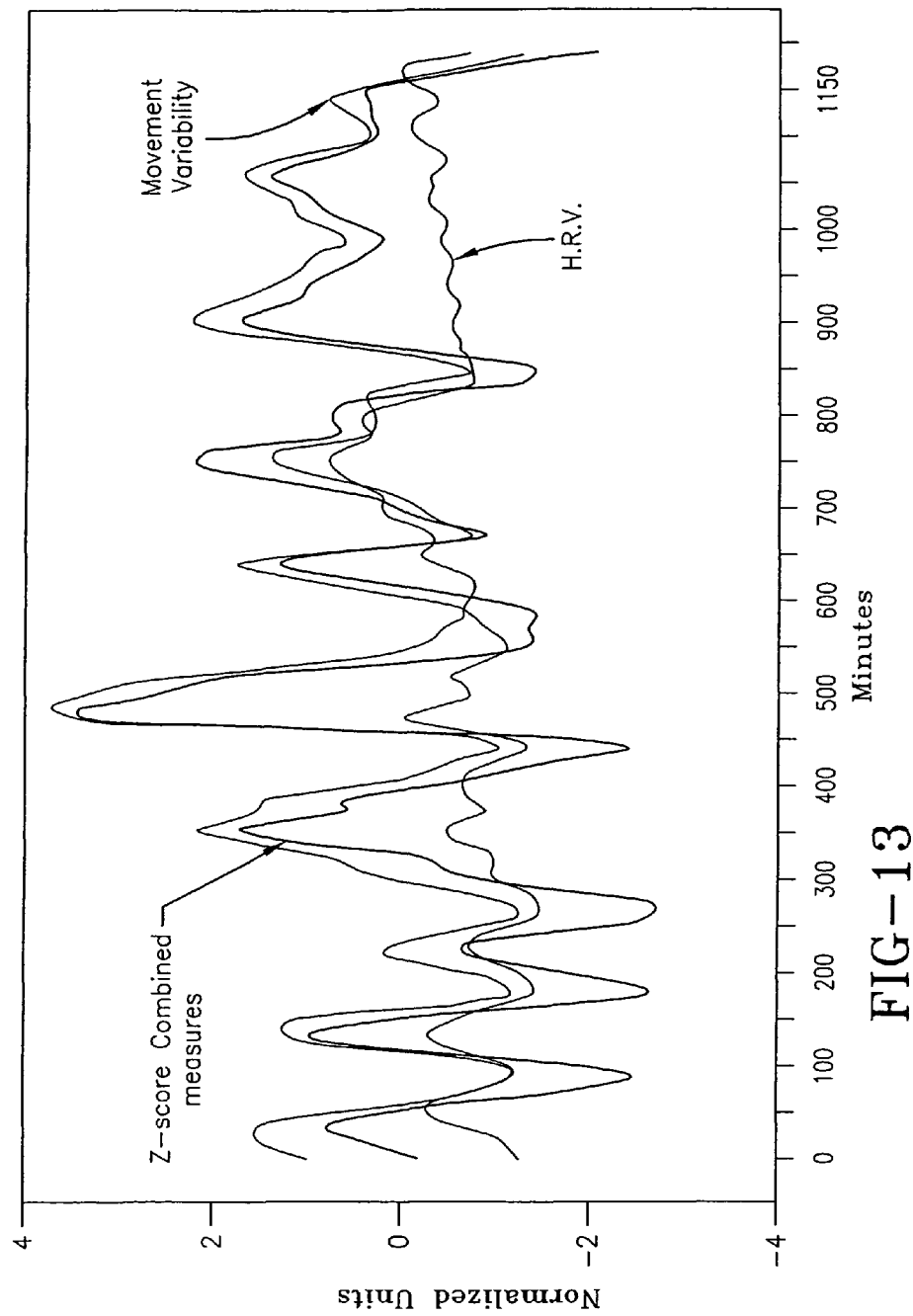
FIG. 13 shows Heart Rate Variability and Movement Variability Combined As One Signal, called a 'z-score'. The time series is from a normal youth. The two data sets are converted into normalized units, so that one can be directly compared with the other.

The data obtained is then shown as a time-series plot for both heart rate variance and movement variance. Any one or more physiological measure(s), sampled more or less frequently, such as temperature, oxygen saturation, blood pressure, glucose concentration, voice, etc. may be used. Interest lies in both the short and long term correlations of each individual signal as well as in the cross-correlations of several simultaneously recorded signals. Theoretically each of these measures has an infinite number of indices that characterize patterns in the data, dependent upon the initial conditions and the tasks that the system performs. The spatial-temporal structure of respective transitions of an individual physiological variable is studied. The interaction of one ultradian rhythmic pattern with a second or third, (mostly orthogonal), ultradian rhythmic pattern provides a wealth of information about the integrated, coordinated function of a biological system. The inventor has found that the spatial-temporal characteristics of compound records are useful. These methods, taken together, reveal previously hidden, systematic patterns that now emerge using the inventive type of analysis. FIG. 13 shows Heart Rate Variability and Movement Variability Combined As One Signal. The time series is from a normal youth. The two data sets are converted into normalized units, so that one can be directly compared with the other. The combined signal of variability is called a Z-score. There are nine peaks in variability with twice as many transitions over the 20 hour period of the recording.

In the examples to be discussed below, reference is made to transitional states, i.e., the places where the system changes state, as discussed earlier. Acceleration or deceleration of the rate of change in variances through the period of transition, as well as the spatial-temporal changes in system organization (or disorganization) are quantified through use of nonlinear tools, customized for these applications. These tools include, but are not limited to, Approximate Entropy, Fractal Dimension, Lyapunov exponent, Detrended Fluctuation Analysis, Visual Recurrent Analyses, False Nearest Neighbor, Mutual Information, Hilbert-Huang Transform and Signal Decomposition Analysis etc. The acceleration or deceleration of the variances, along with the organizational complexity of the ensuing system states (age and gender specific); define a 'corridor of health', whose scale-free units offer both quantitative and quantitative analyses of health or of disease.

Changes of state with their (inherently) less organized transitions, have been found by the inventor to provide a scale-free measure (a fractal pattern) representing the system's flexibility as well as its stability to perturbation. The inventor named this scale-free measure an 'Adaptation Ruler', one that can be used to quantify health. A subject's psycho-physiological state is reflected in all aspects of system behavior. Thus behaviors of one part of the system are reflected and linked to other parts of the system.

The inventor has found that the measurement of one or more physiological parameters distinguishes various physical as well as psychiatric diagnoses, such as Major Depression, Bipolar Disorder, Attention Deficit Hyperactivity Disorder and Anxiety Disorder with Panic Attacks, as well individual physical disorders such as Diabetes Mellitus, Sleep Apnea, Carcinoid Syndrome, Guillain-Barre Syndrome, Epilepsy, etc.

The inventor has found that each psychiatric diagnosis, for example, is characterized by a collection of variances of heartbeats and movement whose responses complement each other over the collection period. People with psychiatric conditions, for example, may show either slower or more frequent response to perturbation, where amplitude and acceleration during transitions may be abnormal. These patterns are useful in distinguishing one psychiatric condition from another and from a healthy control.

A precise measure of system adaptation is found in scale free measures called Fractals. They are present at every level of magnification, and have structures that are both self-similar and infinitely complex.

In making an evaluation pursuant to the invention, the waveforms of the variances of two or more, physiological signals are compared side to side or converted into normalized units for consolidated comparison. The change in their velocities over time, along with the magnitude of their accelerations into and out of transitional states, measures the stability and flexibility of the system.

It is well known that moods occur over minutes to hours. In order to investigate the ultradian rhythms of mood state changes which occur over minutes to hours, attention is directed to those long frequency waveforms whose periods correspond to those time intervals. The data collection must occur over periods at least twice as long as the longest period (cycle) under study. As part of this invention, spectral analysis of these long waveform envelopes are used to assess mood states. Both linear and nonlinear analysis methods were used to reveal previously hidden patterns in the data and to study the dynamics of change over time. The invented software can be used to track dysregulated states with their altered fractal patterns that evolve into psychiatric illness. For example, patterns of neurocardiac and motor dysregulation develop over time eventually presenting as clinical depression. The invention allows for these measurements.

Several early studies were completed on a number of individuals according to the invention showing 'proof of principle'. It was demonstrated that the measures described in the invention diagnose both physical and psychiatric illnesses, as well as distinguish improvement (system movement toward health). One such study had as subjects twelve incarcerated adolescent males, before and after therapeutic and psychopharmacological interventions. Two physiological measures, heart rate and movement, were collected simultaneously. Each youth served as his own control. The three examples discussed below represent "proof of principle."

Physiological data in the form of electrocardiograms (Holter monitors) and accelerometers (movement monitors) were collected on each youth, before and after psychotherapeutic interventions. Each youth who wore the monitor was categorized as being under-reactive, normally-reactive or hyper-reactive, based upon clinical information obtained before wearing the equipment.

All of the youth participated simultaneously in each programmed activity, such as wake-up, breakfast, school, gym, TV-watching, lights-out, sleep, etc. The rigidity of each youth's schedule in the setting of a youth prison allowed for easy recognition of the physiological patterns corresponding to particular activities.

Each of the youth's activities was correlated with information from the EKG (electrocardiogram, Holter) and actigraph (movement monitors). This enabled recognition and identification of those patterns common to group activity as well as to those unique to each individual youth as he transitioned from one required pursuit to the next. Reports regarding psychological and behavioral states were made three times a day by both youth and staff.

The Holter monitors (Rozinn Electronics, N.Y.) were used in a one-channel EKG configuration. The Holter and actigraph monitors were worn simultaneously and started synchronously.

Each youth's self-report included information about their mood and behaviors over the recorded period.

The Holter data was analyzed by an M.D. who generated complete analysis reports and data files including a full disclosure (i.e., each heartbeat for the entire 24-hour period) as well as a complete record of each youth's inter-beat intervals for the entire period of the recording. Actigraph records were read using Motionlogger Actigraph Software purchased from the manufacturer Motionlogger Actigraphs, Ardsley, N.Y. Data files of movement analysis consisted of five-second activity counts collected in the "zero crossing" mode (integer counts of movements exceeding a standard threshold).

The inventor oversaw computer analyses of spatial-temporal structure incorporating custom programs. The first program summed the heartbeat data as successive inter-beat times, detecting when the sum reached a predetermined amount (in this case, five minutes), and then calculated the variance for that sequence of inter-beat times. New variances for each of the predetermined time periods (i.e., five-minute intervals) were calculated for a portion of each interval (in this case, for each minute) yielding a sequence of variances based upon overlapping periods of the time period (five minutes, or 300 seconds) of heartbeats updated every minute. This resulted in a sequence of one-minute updates of heart rate variance for a period of 20 hours.

The actigraph data was similarly analyzed using a custom program. Actigraph files were studied over a fairly long period of time (in this case, 20 hours) of activity, with five seconds of activity counts, and calculated using routines comparable to those for the heart rate. New variances for the same time period used for heartbeat counted intervals (in this case, five minutes or 300 seconds) were calculated at one-minute updates, yielding a sequence of variances based on overlapping periods of five minutes (300 seconds) of actigraph measures, updated every minute. This resulted in a sequence of one-minute updates of movement variance, each overlapping the previous one by 20%.

Minute-to-minute measures of heart rate and motion variance were smoothed using a symmetric, tapered, smoothing program with an effective time period of about 20 minutes. It is these smooth variance data from which both the heart rate and movement were obtained for this study. In the test discussed below, recognizable patterns in heart rate variability and activity variability records enabled precise marking of sleep and 'wake-up' (get out of bed) times for each subject. The data for each was converted into normalized units, and, in the case of FIG. 13, the variance of heart rate and movement were added producing a z-score, i.e., the combined signal.

The results of this pilot project delineated normal physiology from either physical or psychiatric illness. Three individuals have been chosen to represent each situation: Andy, Eddy and Michael.

Figure 14:
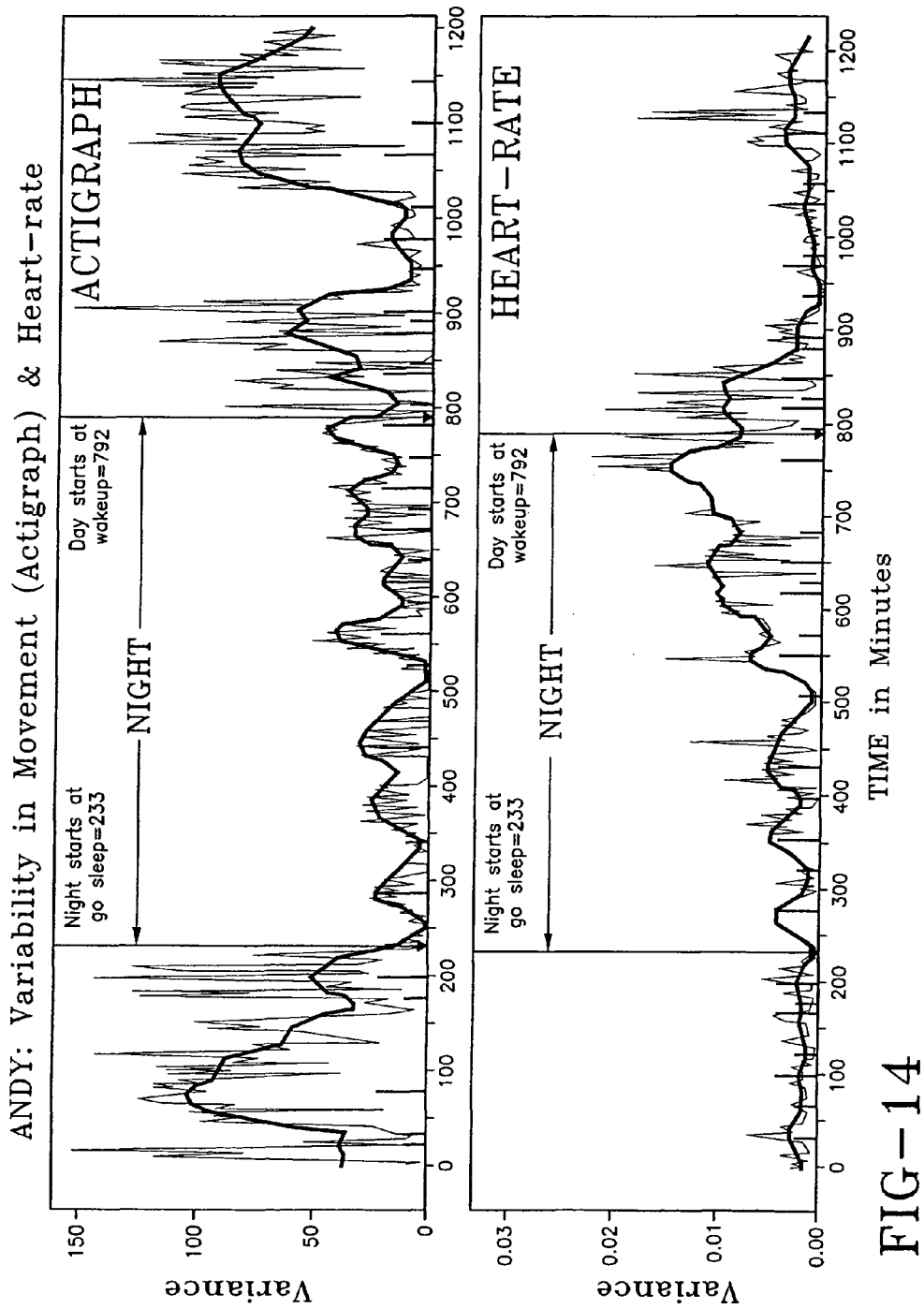
FIG. 14 showing heart rate variability (Bottom of figure) for Andy., and movement variability (top of figure) simultaneously collected for the same youth. Andy had normal physiological reactivity. Twenty hours of the time series is shown, with "go to sleep" and "wake-up" indicated.

Reference is made to FIG. 14, showing heart rate variability (bottom of figure) for Andy. Andy had normal physiological reactivity. Twenty hours of the time series is shown, with "go to sleep" and "wake-up" indicated. Night is indicated by the region between "go to sleep" and "wake-up." The x-axis denotes elapsed time, in minutes, with updates charted every five minutes from "0" (zero) time, ("start time") with one minute overlap. The y-axis provides variance values (in hundredths of a second) for each five minutes of heartbeats occurring before the corresponding one-minute update (one minute overlap of five minute segments). In this figure are shown minute-to-minute heart rate variances as the smoothed curve of variance for 20 hours, marked in minutes of elapsed time over the time series. The plot shows that Andy went to sleep at 233 minutes (3.88 hours elapsed time), and that the day started with wake-up at 792 minutes (13.2 hours elapsed time) into the recording. The changing patterns in the time series are due to transitional events.

An actigraph time series, recorded simultaneously from the same youth, Andy, is slown in FIG. 14 (top of figure). Night and day are also delineated. Zero time is the start of the recording.

Simultaneous measurements of heart rate and movement provide complementary (sometimes orthogonal) measures over 24 hours of data collection. The variances of both heart rate and actigraph are shown for the same time series for Andy. A rapid decrease in variance in Andy's actigraph occurs at the time of sleep onset, with small fluctuations in variance throughout the night, corresponding to individual sleep stages. In contrast, heart rate variance, increases dramatically at the time of sleep onset, and it fluctuates throughout the night. FIG. 14 Variability in movement and heart rate for Andy. Note how movement variability is greater during the day while heart rate variability shows greater fluctuations at night during sleep.

Both heart rate and actigraph time series are then converted into normalized units, enabling comparison of one variance to another. The behavior of these signals varying one to another, over the course of 24 hours, permits description and analysis of the spatial-temporal characteristics of these compound records.

Details of the interbeat interval distribution of heartbeats over 24 hours may be calculated using linear or nonlinear tools and displayed in a variety of ways. The time series many be studied with linear tools, such as Fast Fourier Transform (FFT), in the time domain (standard deviation) and in the frequency domain (power spectra). Additional information about the dynamics of the time series is revealed through nonlinear analysis. For example, approximate entropy, a nonlinear tool, measures regularity of the signal.

Andy's interbeat intervals may be plotted as a histogram where groups of heartbeat intervals, as counted lengths, are plotted over twenty four hours and fitted to a Gaussian distribution, a linear measure. The bell-shaped curve shows that heartbeats collected for 24 hours follow a bimodal distribution. The longest heartbeats are those found during sleep, with a second pattern seen during wakefulness. For those people who exercise, there is a third pattern that comprises the shortest inter-beat intervals, the remainder making an awake-time, i.e., daytime, distribution. A healthy person has a bi-modal or tri-modal distribution.

Histogram plots may be used to represent the times and duration of transitional events. A histogram is a plot or graph that represents the end duration of transitional events. The inventor shows that that the onset and offset of transitional events, as well as the length of these events, separate healthy adaptations from unhealthy ones, and are thus useful for diagnostic purposes.

The histogram of heart rate variability shows that cardiac transitional events are longer in duration at night than they are during the daytime. Heart rate transitional events at night can be seen to have had longer onsets than offsets.

Figure 15:
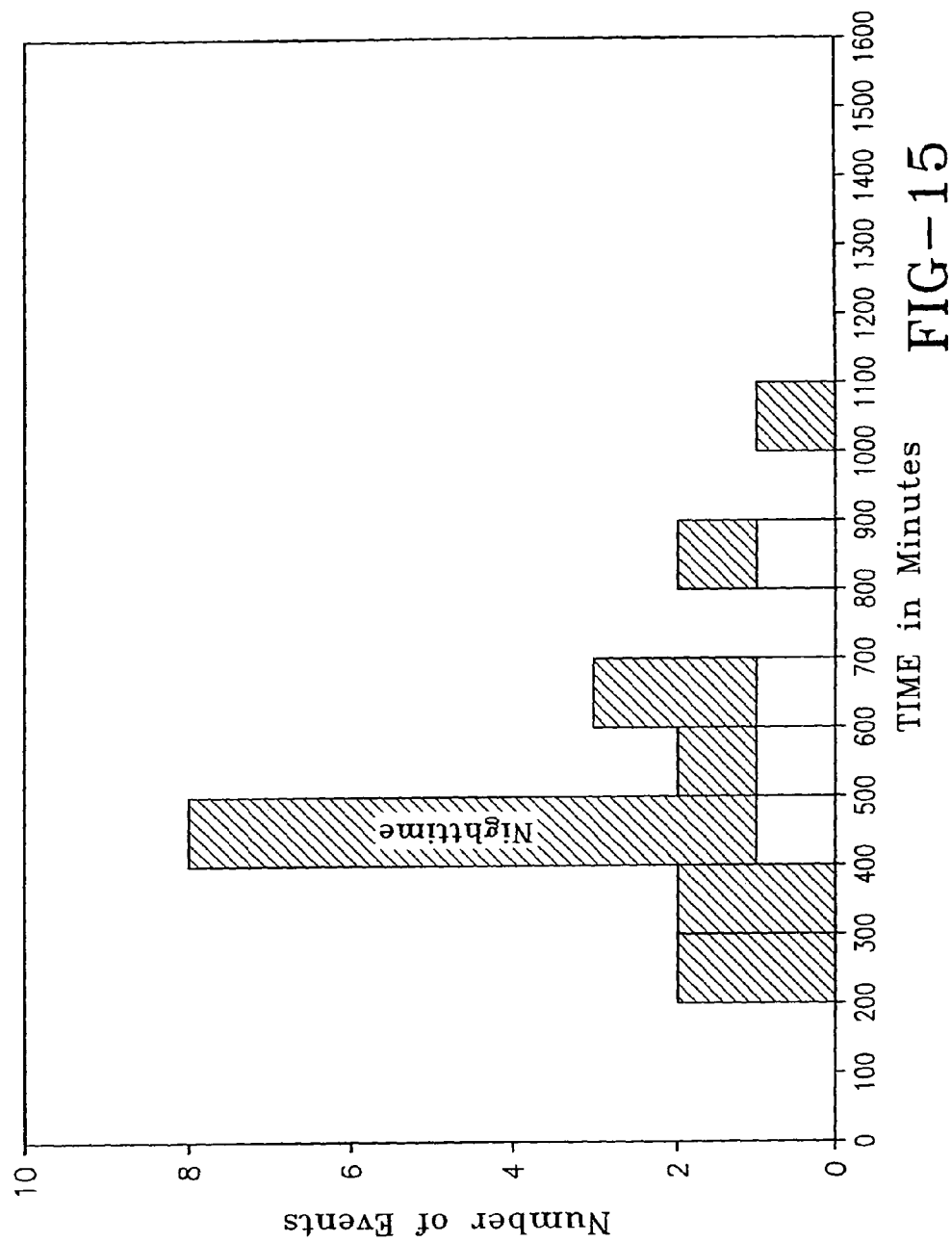
FIG. 15 shows an Event Histogram for the Duration of Heartbeats in a youth with heart disease, requiring a pacemaker. His nighttime heartbeats were of exceptional length, and several of his nighttime sleep phase transitions were exceptionally, pathologically long.

The next youth studied was Eddie. Although he had several psychiatric diagnoses, Eddie felt himself to be in good physical health and his physical examination was also unremarkable. However, his 24-hour EKG Holter monitor showed paroxysmal third-degree heart block, a medical emergency. This condition, called "Sick Sinus Syndrome" requires immediate surgical implantation of a cardiac pacemaker. Although completely asymptomatic, Eddie's event histogram shown in FIG. 15 shows that his nighttime heartbeats were of exceptional length, and several of his nighttime sleep phase transitions were exceptionally, pathologically long. Untreated, he would have certainly died in his sleep, for his heart stopped for several seconds, off and on, all night long.

Figure 16:
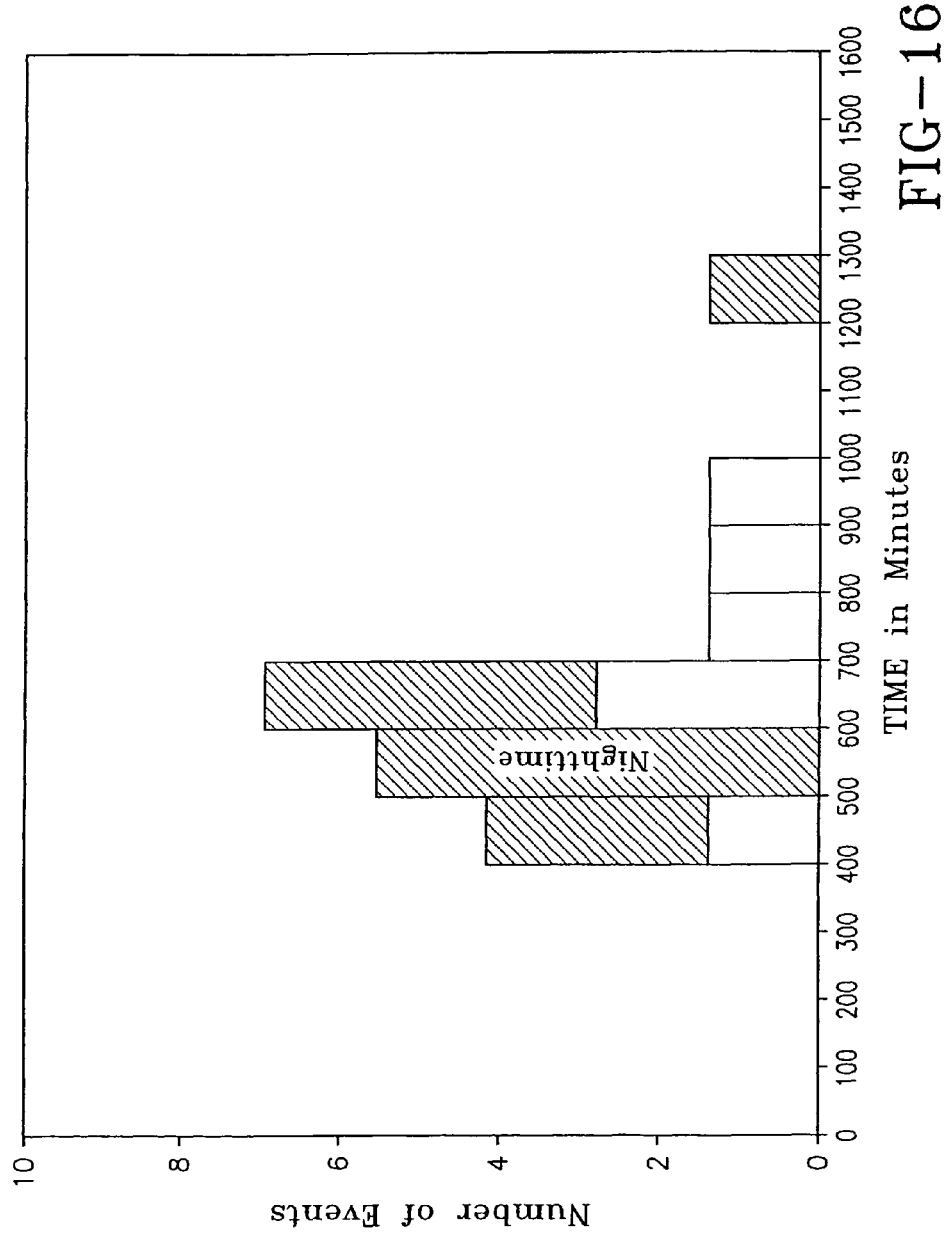
FIG. 16 is an Event Histogram in the same youth for the Duration of Heatbeats, taken two weeks after a pacemaker is implanted. It shows too little variance, both day and night. This is a common situation soon after a pacemaker implantation.

Two weeks after Eddie's cardiac pacemaker was implanted, Eddie's event histogram shown in FIG. 16 shows too little variance, both day and night. This is a common situation after a pacemaker implantation, and the usual procedure is to adjust the pacemaker to allow greater flexibility in heartbeat periods. The inventive software shows not only the pattern of the abnormality, but tracks the movement toward health.

Figure 17:
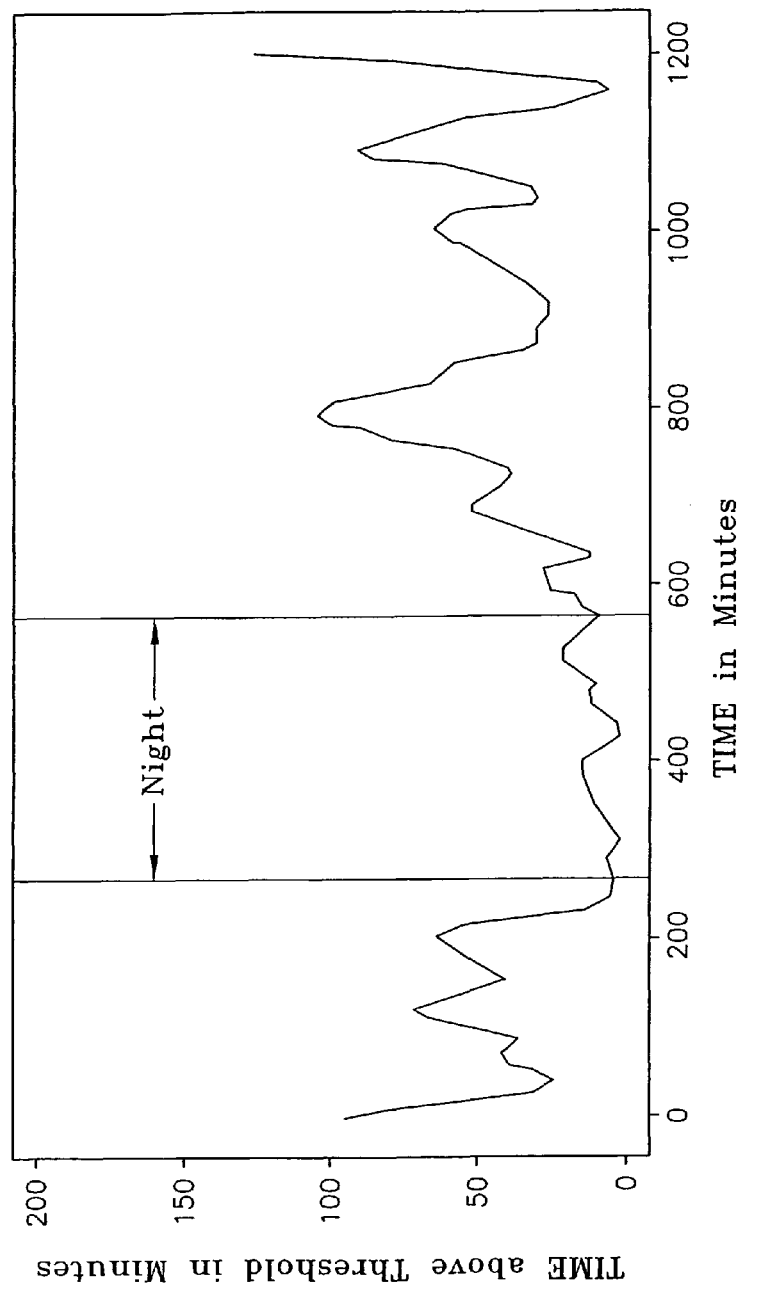
FIG. 17 is an actigraph of a youth, Michael, showing Movement Variability in Depression, collected over a 20 hour period.

Michael, the third youth, suffered from severe depression yet he had hidden this from staff. The heart rate variability and movement measures revealed both the existence and the severity of his depression. For example, the variance in his heart rate, normally greater during sleep, was quite reduced for his age and gender. His accelerations into and out of transitions during the night indicated that he had abnormal sleep architecture. His actigraph recording showed that his sleep was poor and he had too much motion at night. FIG. 17 is an actigraph showing Movement Variability in Depression with movement variance shown over a 20 hour duration. Night, i.e., Seg B, is indicated by the bars. FIG. 17 represents Michael's movement variability before treatment. This is for Michael before treatment. This 20 hour recording of Michael's motion variability shows that he sleeps poorly at night and moves around too much, with transitions that are too frequent both into and out various of sleep stages. This is a pattern associated with clinical Depression. He has less variability in movement during the day than is normal. This pattern is typical of depression. The x-axis is time in minutes, while the y-axis is time above threshold in minutes.

Figure 18:
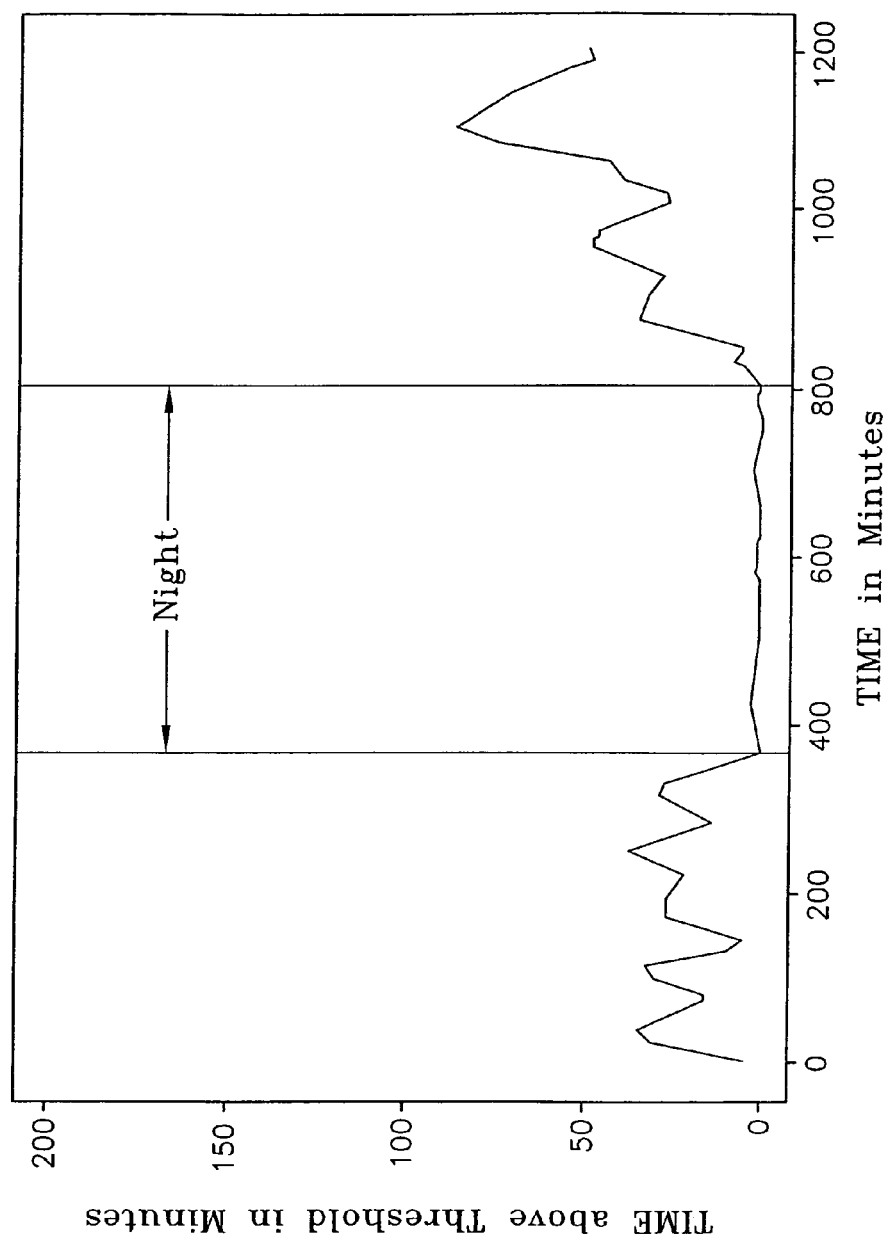
FIG. 18 is an actigraph for the same youth depicting his movement variability after treatment for Depression. Michael's movement has normalized, both day and night after medication was given for depression.

FIG. 18 is an actigraph for Michael depicting Movement Variability After Treatment for Depression. Michael's movement has normalized with medication for depression. The axes are the same as for the figure above.

Michael had a dysregulated pattern of both movement and heartbeat variability consistent with Depression. Michael had difficulty falling and staying asleep, and his sleep was disrupted as well. Although the total time he was lying down was 7 hours (from 220 minutes until 640 minutes in elapsed time), he was constantly moving all night with frequent awakenings. In contrast, he had less frequent variability in his movements during the day than is normal for his age and gender. After pharmacological treatment for his depression, his actigraph showed him to be sleeping very soundly at night, for longer time periods, with little variability in movement during sleep. The variability in his daytime movement returned to the normal range.

Using these test results, it is possible pursuant to the invention to differentiate between people with various undiagnosed psychiatric and physical conditions.

Results obtained through the use of linear and nonlinear analysis are of these two measures lead to diagnoses of several physical and psychiatric conditions. Several examples of the usefulness of this approach are discussed below.

As part of the invented software, healthy corridors, both sex and age specific were constructed from groups of normal individuals who met the following strict criteria:

Turning first to linear analysis in the time domain, the following are mathematical processes exemplifying the type of analysis: Segmented Statistics, Trend Analysis, Histogram. Next, linear analysis was completed in the frequency domain, and the following are reflective of the latter kind of analysis: Waterfall, Contour Graph, Frequency Spectral Analysis, Power Spectral Analysis.

Movement Variability—The latter measurements are also processed by an appropriate computer program and the values are converted into normalized units. The synchronously collected heart rate variability measurements are converted into normalized units, allowing both measures to be directly compared to each other in scale-less units. After correlation, this information is used to create templates of psychiatric and physical disorders.

Figure 7:
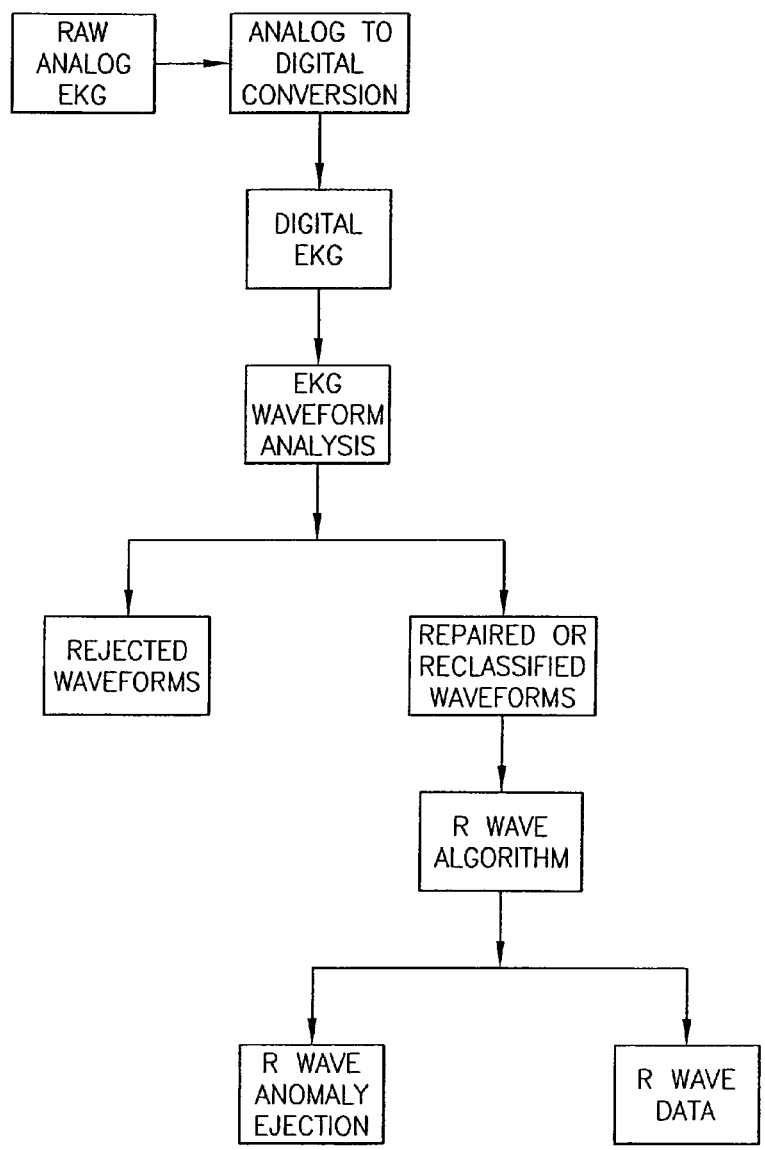
FIG. 7 is a Flow Chart for Processing the Cardiac Signal from a Holter Monitor. The analog electrical signal from the EKG must be converted to a digital signal whose outcome is a valid R-wave signal, now available for further processing.

A summary will be made to explain the processing of a cardiac signal and the processing of heart rate variability signals. Turning first to FIG. 7 raw analog EKG electronic signals are the input to the system. The analog signals are changed to digital signals by an analog to digital converter. Digital EKG is then plotted as a wave form over time as an EKG waveform analysis. Waveform signals which are outside of the normal range, and artifacts at the beginning and end of a session are discarded as rejected waveforms. The repair or reclassified waveforms are then processed to yield a heart beat or R wave algorithm. Those algorithms which fall outside the normal range of such algorithms are rejected as R wave anomaly rejection, keeping the temporal placing within the signal, and the R wave data are captured for further processing.

Figure 8:
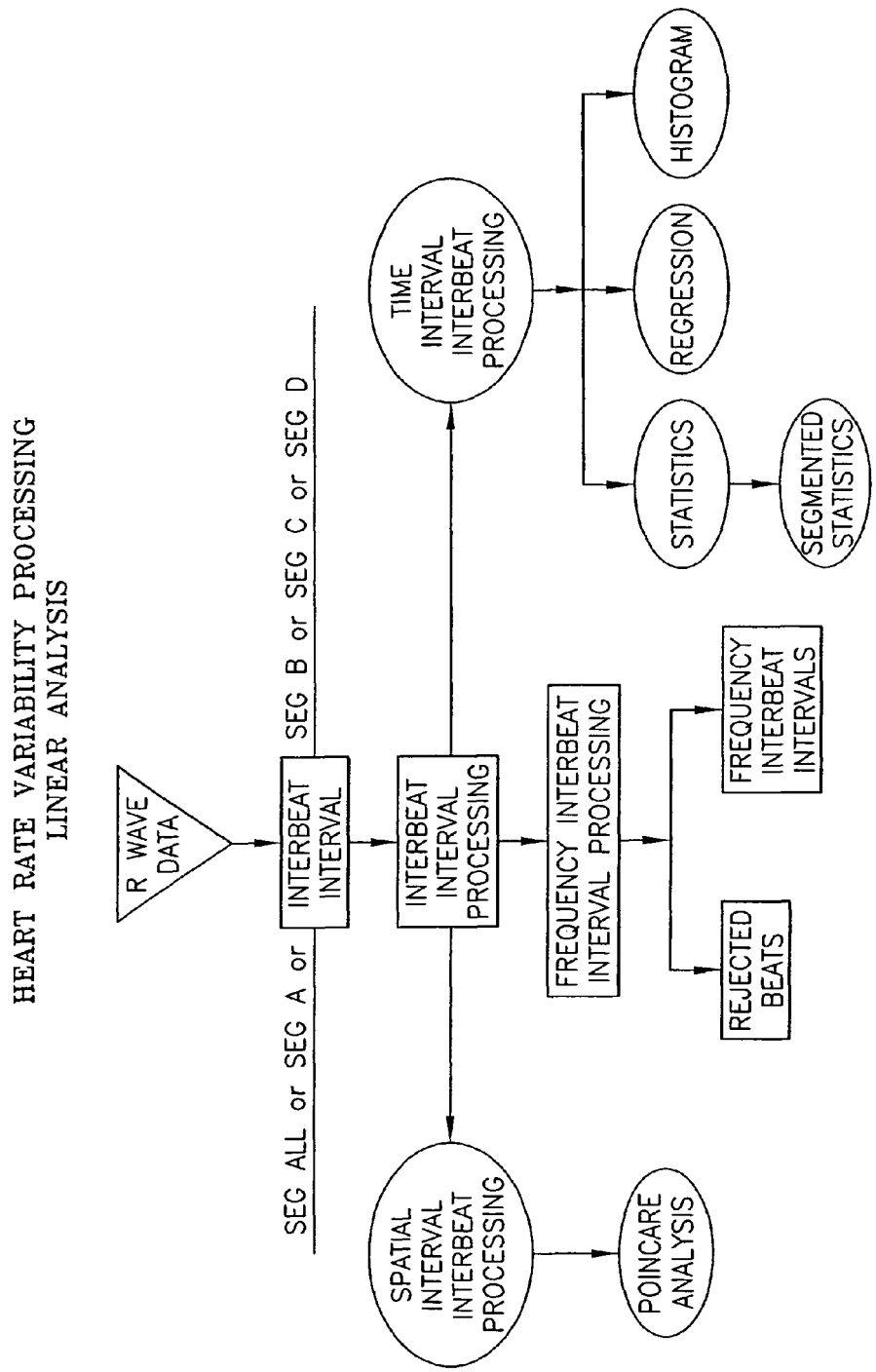
FIG. 8 is a Flow Chart for Linear Processing of Heart Rate Variability.

Turning next to FIG. 8, the R wave data is processed to determine the interbeat intervals over a period of time; and these are divided into several segments (SEG), one covering the entire test period (SEG ALL), another covering a particular period (A) such as a start or zero time until when the person goes to sleep (SEG A), period of time when the person goes to sleep until when the person wakes up (SEG B), the time when the person wakes up until the end of the set collection period (SEG C), and finally from the end of the first period, Seg A, until the test is terminated (SEG D).

The interbeat interval processing is done as both spatial processing and time processing. The special interval interbeat processing involves a Poincare analysis. The time interval interbeat processing is used to produce statistics, which can be the segmented statistics (SEG ALL, SEG A-SEG D), regression and the histograms, all discussed above.

The frequency of the R wave data is also processed. FIG. 8 includes the step frequency interbeat interval processing, from which beats falling outside an expected range are rejected, and the frequency interbeat intervals are further processed as indicated in FIG. 8. The frequency is plotted and an envelope of the maximum and minimum value of the beat is prepared. The plot measures frequency (in hertz) against power, a spectral analysis is prepared categorizing the spectrum into ULF, VLF, LF, HF and VHF. The ULF is most important with respect to the present invention. From ULF spectral analysis, the following graphs can be prepared: waterfall graph, contour graph, stacked power, power ratios and an auto-regressive analysis. The auto-regressive analysis is processed to yield diagnostic templates and age/sex matched normals.

Figure 9:
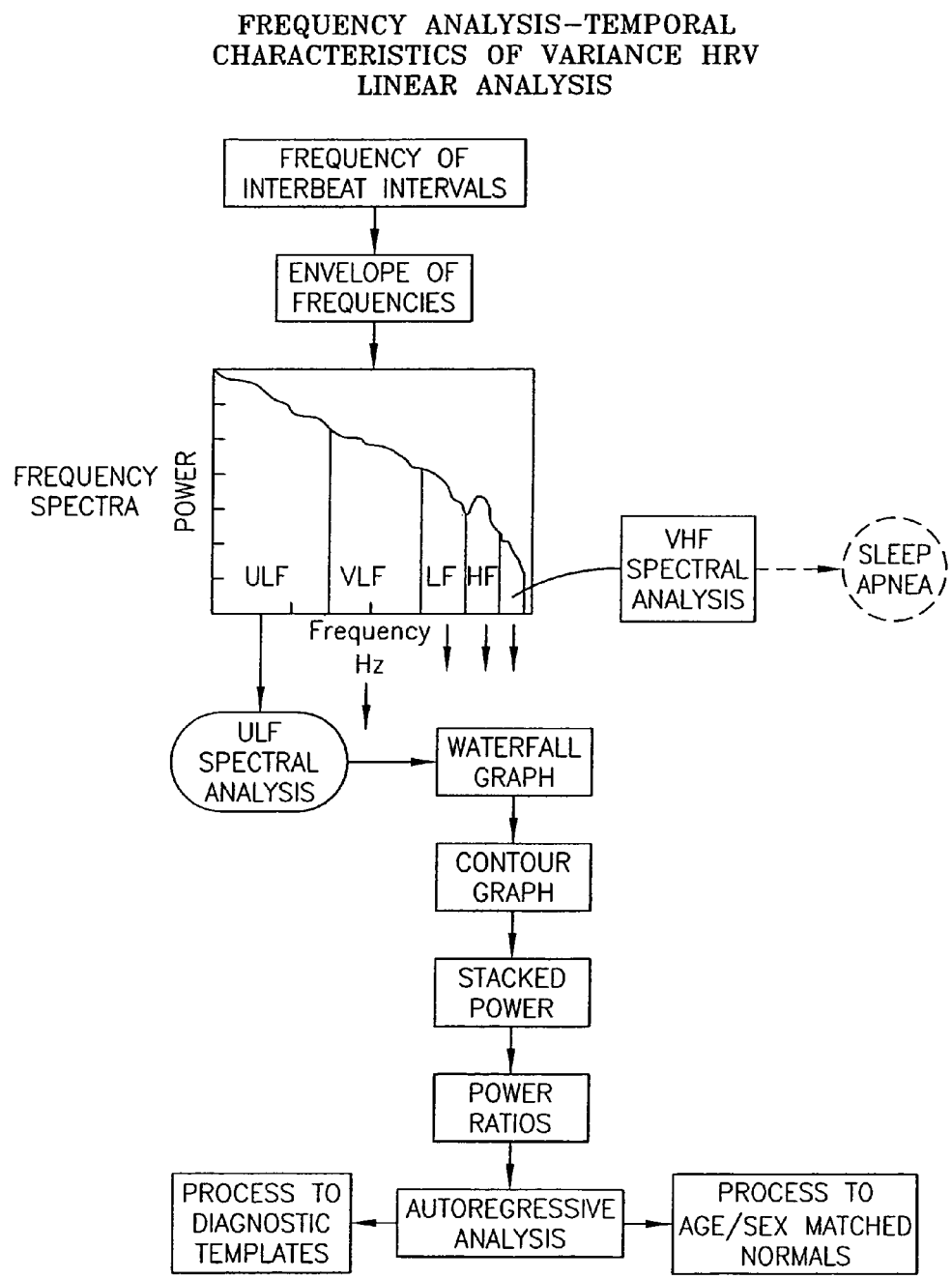
FIG. 9 represents Frequency Analysis of Heart Rate Variability. It is a flow chart for linear processing of heart rate variability in the frequency domain.
Figure 10:
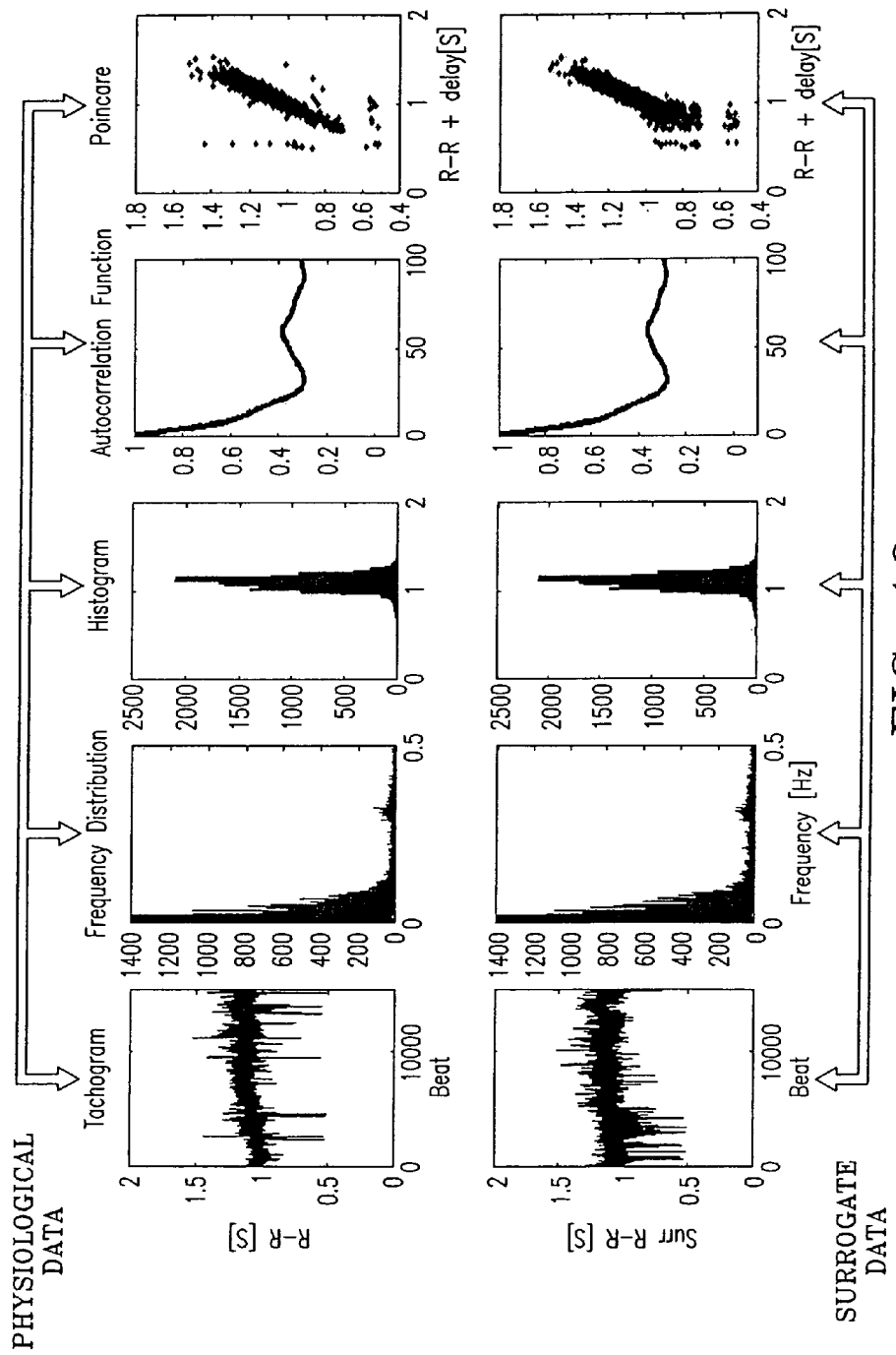
FIG. 10 represents Comparison of Physiological Data (Top) with Surrogate Data (bottom). Surrogate data does not contain the temporal ordering of the physiological time series, yet the two data sets are indistinguishable from each other using linear measures. Only when nonlinear measures are used on the two sets, does the real data separate out.

A flow chart for general nonlinear analysis is shown in FIG. 9. The input is a linear analysis. The time domain and frequency domain are input into the general nonlinear analysis. The general nonlinear analysis can process either of the inputs with any of the nonlinear processing tool for the particular purpose as shown. Alternatively, all of the tools can be used. The time domain and frequency domain inputs can be processed with the Hilbert-Huang Transform from which signal decomposition is determined, and from which various analyses can be made depending upon which of the decomposed waves are analyzed. A visual recurrence analysis can be made. Another possible processing step is used to determine the approximate entropy. A detrended fluctuation analysis can be run on the time series. A dynamic Poincare (movie) processing can be made from the Poincare map. Correlation dimension can be determined. The Lyapunov exponent derived from the Lyaponov dimension can be determined. The Wigner-Ville determination can be made. A fractal exponent can be determined from the fractal dimension. A false nearest neighbor mathematical process can be performed on the time domain input and the frequency domain input, to give information about the embedding dimension. These are all nonlinear processing functions, and one or more are used for a particular purpose to characterize the system and its changes.

Figure 20:
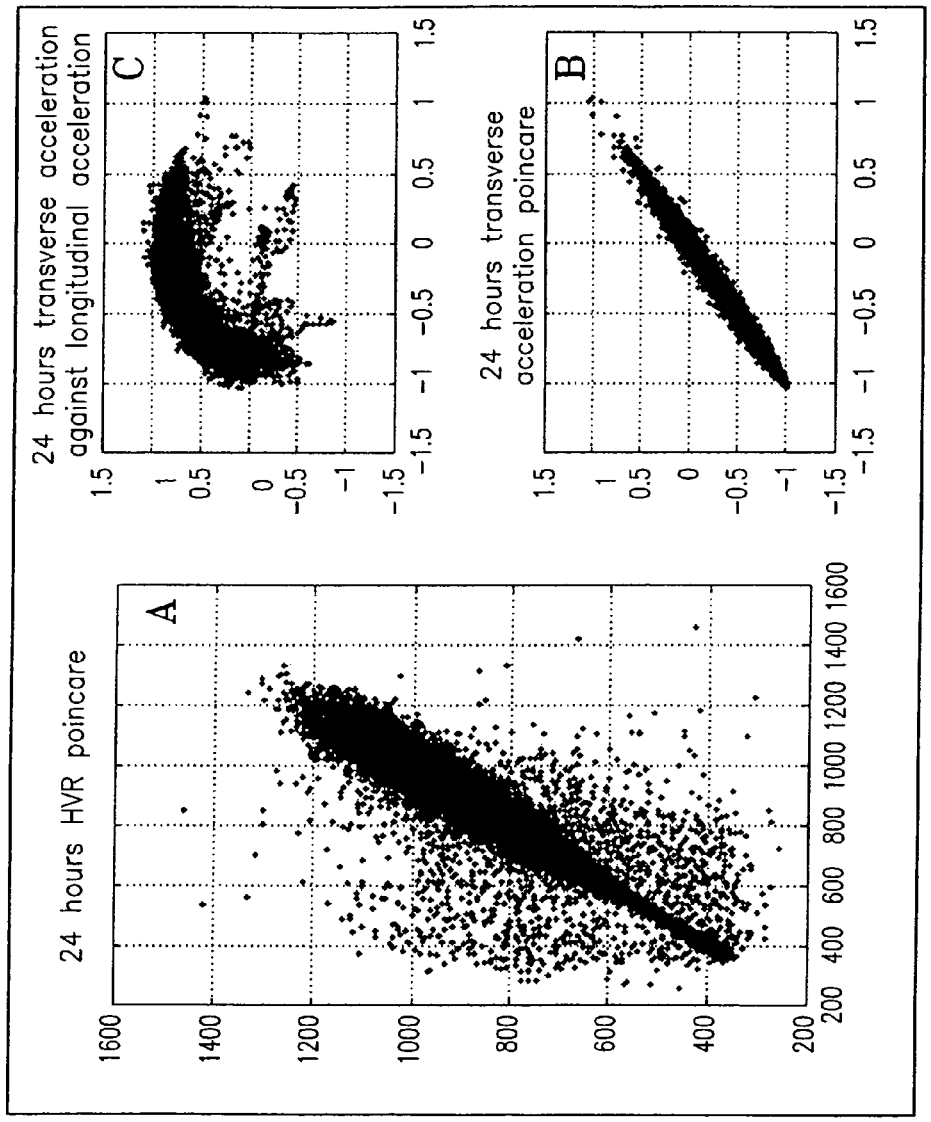
FIG. 20 shows three Poincare graphs representing the variability of three physiological signals, heart rate, horizontal and vertical acceleration, simultaneously collected and analyzed over twenty four hours, as examples of nonlinear analysis of these signals.

Movement variability over 24 hours is plotted. Acceleration variability on the longitudinal axis (walking, jumping, etc.) is plotted against that of the variability of the transverse accelerometer (moving arms side to side, lying down, etc.). Both measures are first put into normalized units. This is shown in FIGS. 20A, 20B and 20C, which are Poincare graphs. FIG. 20A is a Poincare of Heart Rate Variability over 24 hours, where the x-axis is heart rate variability, R-R interval, in minutes, and the y-axis is the R-R interval +1. FIG. 20B is a Poincare of Transverse (Horizontal) Acceleration simultaneously collected over the same 24 hours. The Poincare graph in FIG. 20B for transverse acceleration is cigar shaped, narrower in short term variability yet it occupies a greater region of state space that does the corresponding Poincare of heart rate variability, with larger and longer term correlations in the variability of movement, compared to variability of heart beats. It is plotted with variability of movement on the x-axis using "Zero-Crossing," and the y-axis is "Zero-Crossing +1." A Poincare of transverse acceleration is plotted against longitudinal acceleration in FIG. 20C. The units are scale-free and this shape is a fractal, transversal to the attractor, although the attractor of movement hasn't yet been described. For the Poincare in FIG. 20C, Transverse Acceleration is plotted on the x-axis, against longitudinal acceleration on the y-axis.

Approximate Entropy=ApEn—Entropy is a dynamic measurement of information production while Approximate Entropy is a set of measures denoting system complexity. As part of this inventive work, heart rate variability was studied during sleep and wakefulness in healthy controls of both sexes, from infants to those of old age allowing quantification of an entropy "corridor of health." Then persons with psychiatric conditions were placed into that corridor.

Figure 21:
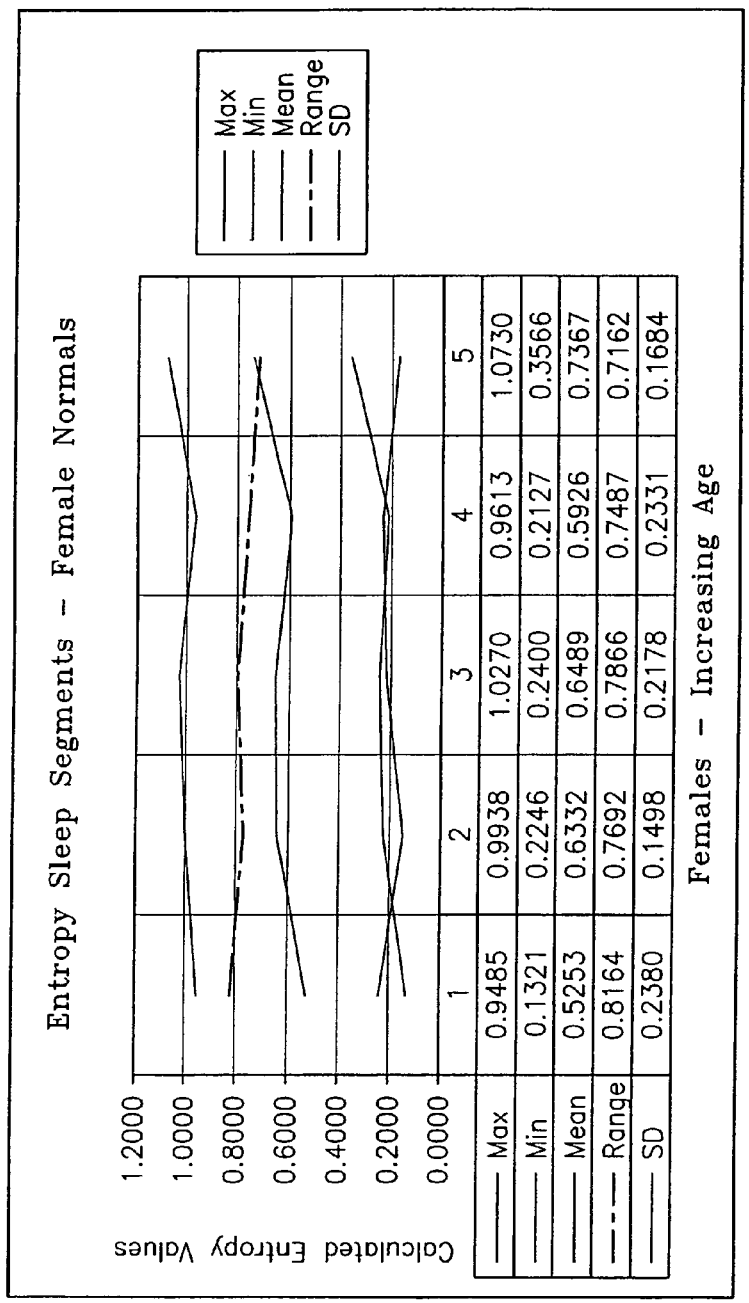
FIG. 21 shows the healthy corridor for entropy values during sleep for females of increasing age (from left to right), showing the gradual decline in dynamic range, with reduction in entropy, i.e., a more regular signal, during normal ageing

FIG. 21 relates to the healthy corridor for entropy of heart rate variability during sleep in females. It is from healthy females (ages 7 to 67 years old, from left to right). One can see that entropy decreases as women age. However, as the body's systems start to break down, entropy then increases until death.

Figure 22:
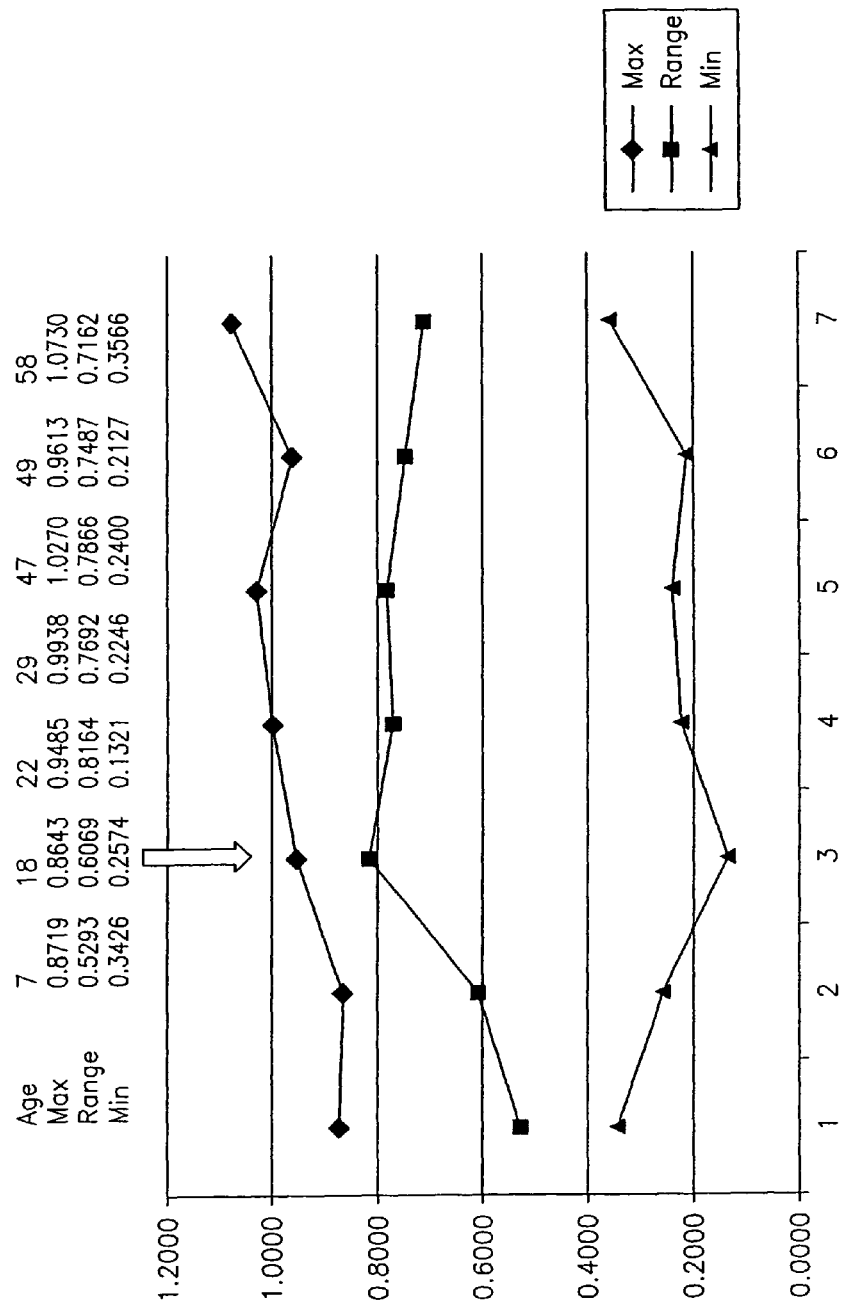
FIG. 22 is a diagram of values for entropy during sleep in females of increasing age, including one female with Post-traumatic Stress Disorder (arrow), whose entropy sleep entropy is clearly abnormal, compared with the "healthy corridor," due to her psychiatric condition.

Approximate Entropy (ApEn) thus provides quantified physiological information underlying variability of the cardiac cycle. This corridor of health could then be used as a template to compare with those who had physical or psychiatric conditions, as seen in FIG. 22. A female with Posttraumatic Stress Disorder has been placed within the appropriate age-matched place within the entropy "healthy corridor" for sleep. ApEn of sleep in females (normal) including one woman with PTSD, see arrow. Her sleep shows disturbed organization with higher than expected entropy for her age, in both maximum and range. Her minimum entropy is lower than other healthy women her age. Of note, after treatment (not shown), these values returned to age adjusted norms. Age is on the x-axis and the scale-less units of a fractal are on the y-axis (same as for the figure above).

Changes in entropy as a function of sleep phase were revealed by separating the time series into five minute segments and using a variable moving window without overlapping. Results showed higher variability in entropy during sleep than during wakefulness, with entropy decreasing as a function of age.

Approximate Entropy (ApEn) quantified physiological information underlying variability of the cardiac cycle. The ApEn algorithm (NnR) was applied to successive sections within the 24 hour time series for each subject to quantify entropy during sleep and wakefulness along with its changes as a function of age. Then changes in entropy as function of sleep-phase (stage of sleep) were studied, by separating the time series into five minute segments and using a variable moving window without overlapping. Results showed higher variability in entropy during sleep than during wakefulness, with entropy decreasing as a function of age. Entropy during individual sleep stages, showed largest entropy during REM sleep and during intra-sleep awakenings. The minimum (smallest) entropy occurred during deep sleep.

Figure 23:
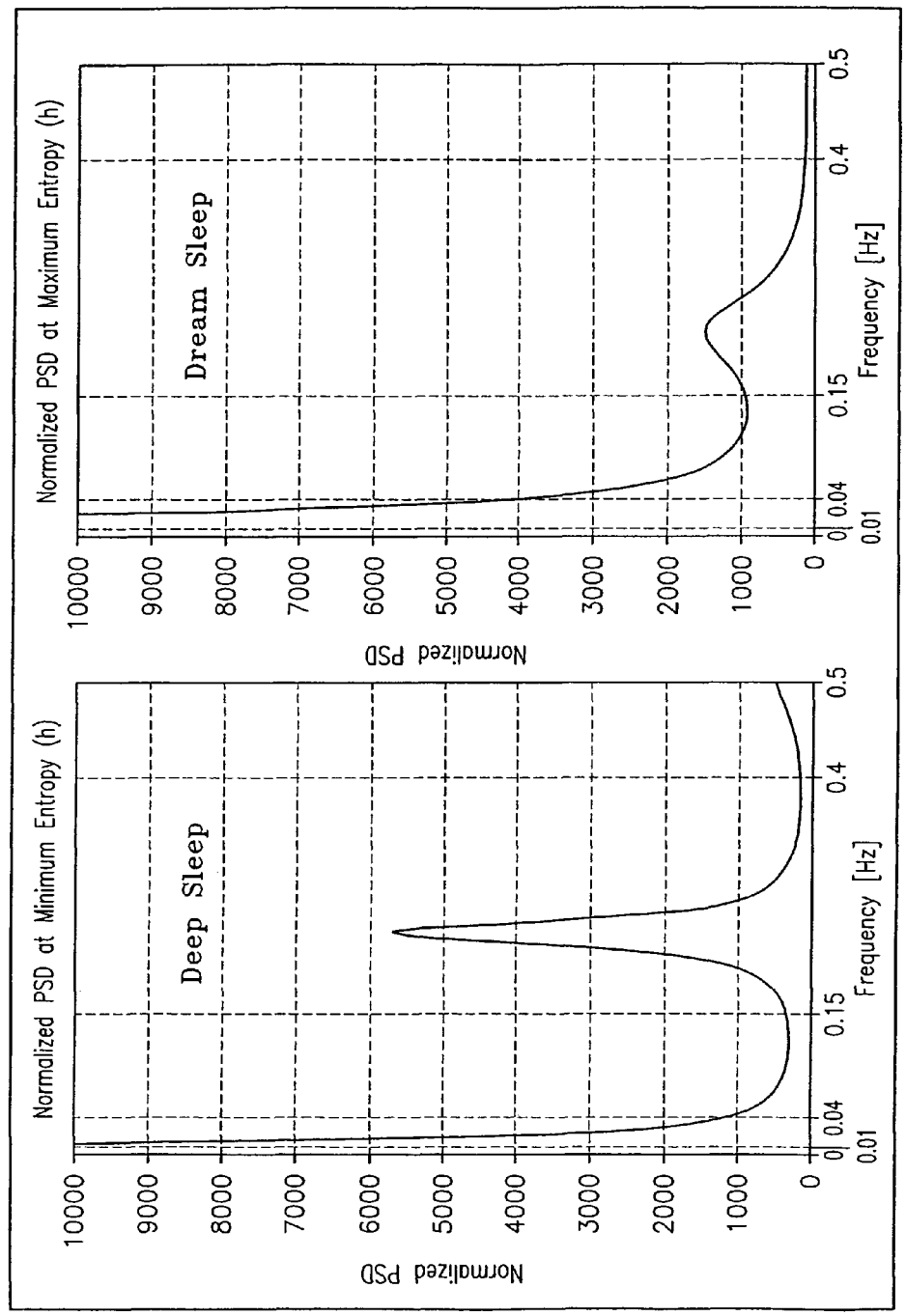
FIG. 23 (left) shows entropy at two sleep stages.

FIGS. 23 (left), 23 (right) are plots showing entropy of heart rate variability at two sleep stages. The lowest entropy FIG. 23 (left) is recorded during deep sleep, while the highest entropy is seen during dreaming, FIG. 23 (right). Both records are from one healthy adult. For this figure, entropy is calculated from the frequencies of heart rate variability with the x-axis in Hertz (Hz) and the y-axis in normalized units of power spectral density (scale-less units).

Entropy=H is a measure of disorder in a system, as well. Calculation of entropy is done by the approximate entropy=ApEn algorithm: ApEn (N,m,r). HRV variability data was given visual representation as quantitative Poincare plots with the Poincare on the left (FIG. 24A) showing dream sleep (REM sleep), and that on the right (FIG. 24B), showing deep sleep (Phase 4 sleep). ApEn was calculated and showed differences in the shape of the Poincare plot, with REM sleep having the most widely distributed pattern, while deep sleep has the smallest, and least distributed pattern. Changes in entropy as function of sleep-phase was made by separating the time series of R-R-intervals into five minute segments using a variable moving window without overlapping. Entropy during individual sleep stages, showed the largest entropy during REM sleep, with H=1.1261 and the smallest entropy (most orderly) occurring during deep sleep, H=0.7796. Entropy was quantified using the Approximate Entropy algorithm—ApEn(N,m,r))x. This algorithm quantifies the predictability of subsequent amplitude values of the signal based on knowledge of the previous amplitude values present in the time series. Approximate Entropy, ApEn (N,m,r), is a measure of whose relative values depend upon three parameters: the length of the analyzed sample (N); the number of previous values used for prediction of subsequent values (m), and the parameter r, usually called the filter factor. The filter factor is the most sensitive parameter, which, with an infinite amount of data, should approach zero. With finite amounts of data or/and measurement noise, its value must be greater than the level of signal noise. Entropy for each sleep stage was quantified, using a moving window of five minutes, with no overlapping. In this case, N corresponded to the interval inside each window, with N between 100 and 5000. The parameter, m, was selected between two and three and the filter factor r was selected as 0.1 SD.

Figure 24:
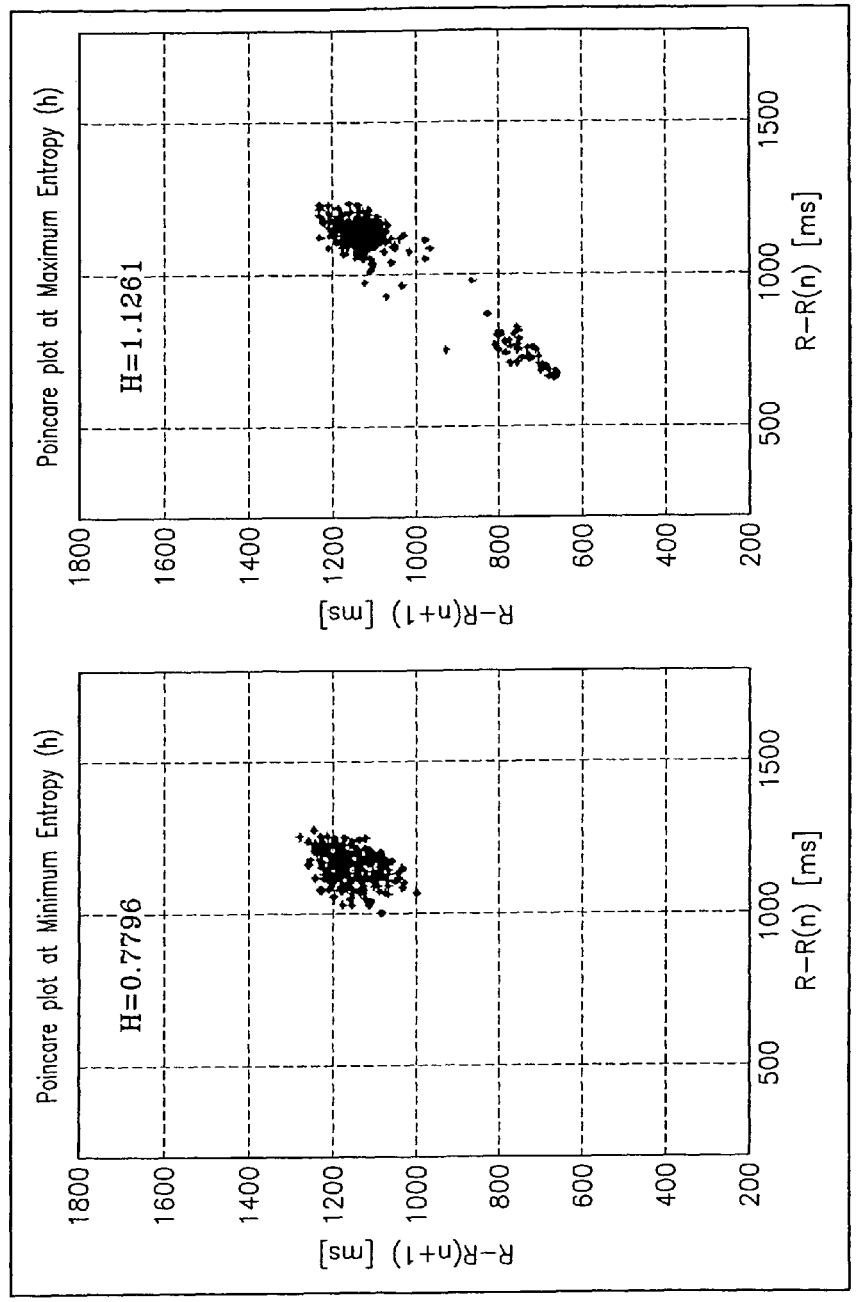
FIG. 24 shows entropy at minimum values, as Poincare during deep sleep H=entropy=1.7796 (left) and Poincare at maximum values of entropy during dream sleep H=1.1261 (right). This corresponds to poincares of deep sleep, and dream sleep, respectively.

FIGS. 24A, 24B are plots showing a Poincare graph of entropy at two sleep stages. They are the same two sleep stages in the same person as in FIGS. 23A and 23B. The highest entropy is seen during dream sleep, FIG. 24 (right) and the minimum (lowest) entropy is seen during deep sleep, i.e., FIG. 24 (left).

Figure 25:
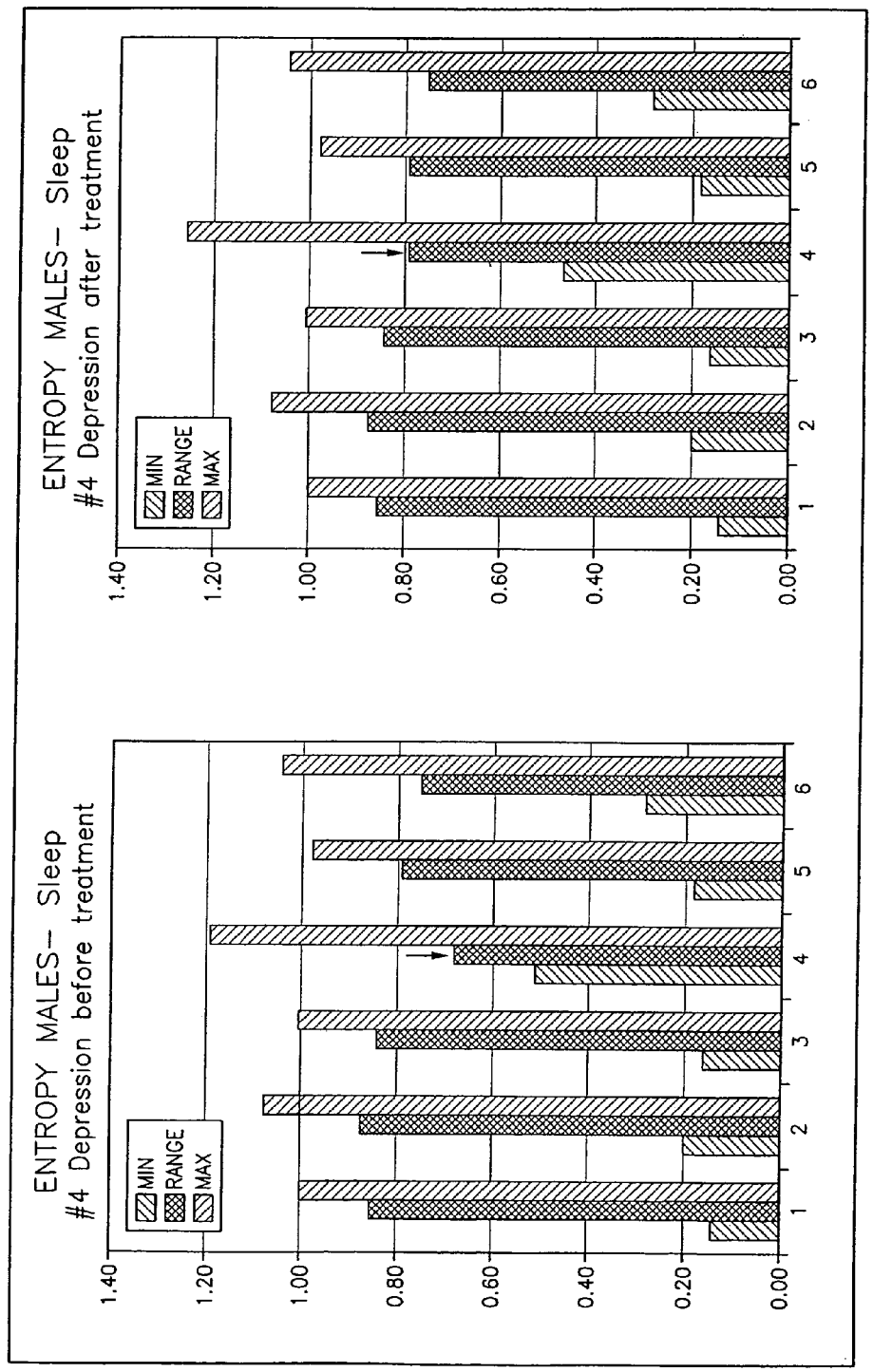
FIG. 25 are entropy graphs during sleep time, of normal males of increasing age (from left to right). The graph includes one male with depression.

Entropy of heart rate variability during the entire sleep cycle is shown for five normal men (#1,2,3,5,6,) from youngest (#1) to oldest (#6) along the x-axis in FIG. 25 (left); The Healthy Entropy Corridor of Normal Males is compared with that of a depressed male, before and after treatment. The minimum and maximum entropy of each male form a corridor showing healthy adaptation. The minimum and maximum entropies of each form a corridor showing healthy adaptation. Note how the adaptive range slowly decreases with age, with (minimum) entropy, the baseline, increasing gradually with age. In contrast, the sleep entropy of a depressed male (#4 arrow), FIG. 25 (left) is inserted at his chronological age within the entropy corridor. The diagram on the left shows that both his minimum as well as his maximum entropy during sleep is larger than normal, indicating that his sleep is more disordered than normal for his age due to his depression. His adaptive range is quite limited and it is also quite decreased. After treatment for Depression, the sleep entropy of the same individual is shown to be within the corridor of health, seen in FIG. 25 (right). Now his adaptive range (#4 arrow) falls within the normal range within the healthy corridor for his sex and age, indicating successful treatment. The axes of the two figures are: x-axis is age, increasing from left to right, and y-axis is scale-less.

The heart rate variability data were given visual representation as quantitative Poincare plots, corresponding to total sleep-time as well as to individual phases within the sleep cycle. Healthy people show characteristic shapes of their Poincare plot. These results were correlated with ApEn and showed differences in the shape of the Poincare plot, with REM sleep having the most widely distributed pattern, (as if the person were awake) while deep sleep has the smallest, and least distributed pattern. An "entropy corridor" for health was obtained.

Figure 26:
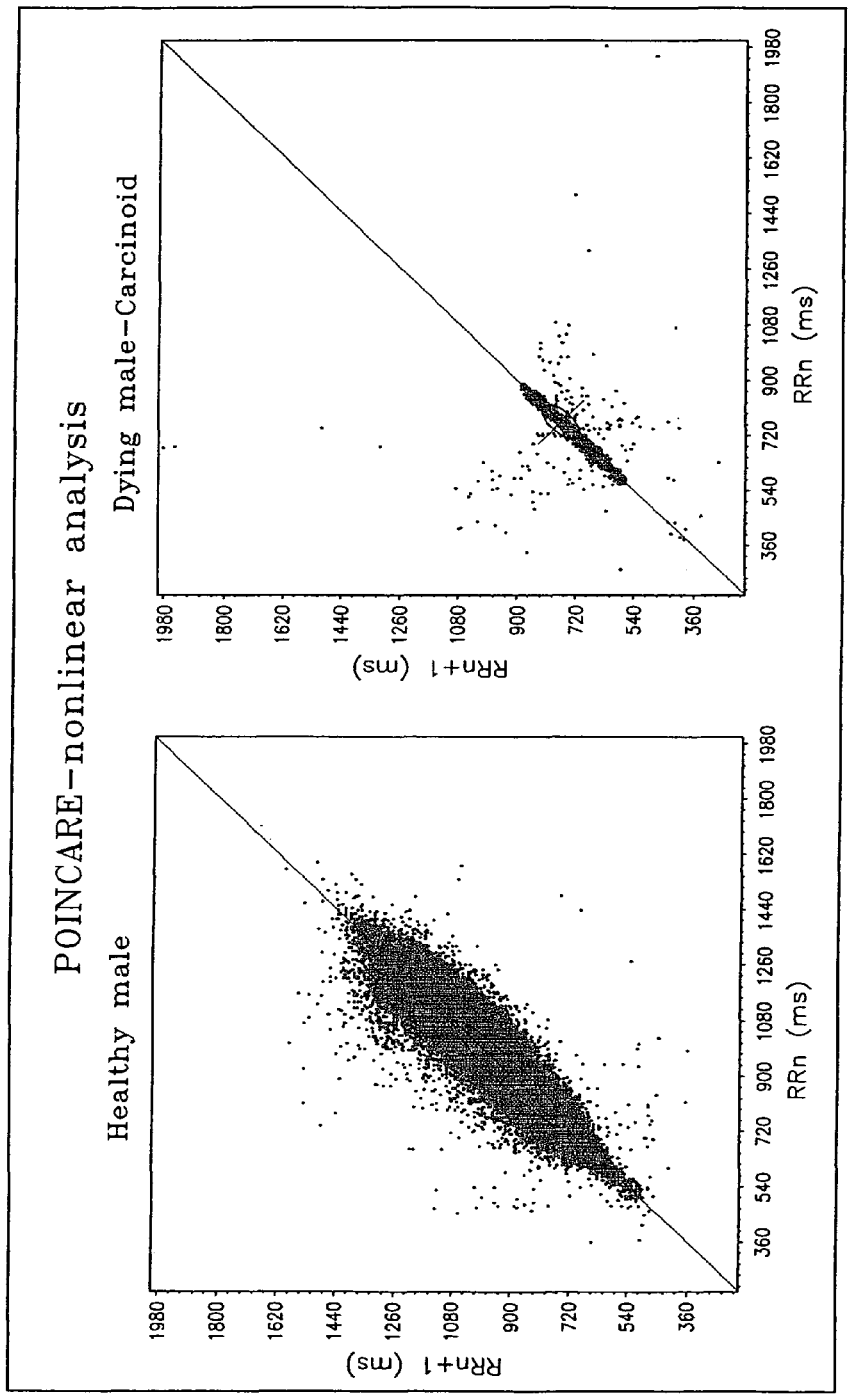
FIG. 26 includes Poincare plots of heart rate variability over 24 hours of a healthy male and a male with carcinoid tumor (cancer) who lost all flexibility of response and died within a month after this study.

Several pathological conditions can be seen diagnostically if this "baseball bat" characteristic shape is not displayed, such as congestive heart failure; carcinoid tumor, etc. As proof of the value of the Poincare, this inventor was able to accurately determine age, gender, health and diagnostic status using data sets blinded to her. FIGS. 26 left, and right, respectively, are Poincare plots of a healthy person versus a person with a Carcinoid Tumor. Both are 24-hour Poincare diagrams heart rate variability of sex (gender) and age matched adult males. The Poincare, a recurrence plot, shows the pattern of heart rate variability over 24 hours. The R-R interval (heart rate variability=HRV) is plotted on the x-axis while R-R +1 is plotted on the y-axis. The Poincare on the left, FIG. 26 is that of a healthy male, collected over 24 hours, the same age as the gravely ill man whose Poincare appears on the right FIG. 26. For a healthy person, the Poincare is shaped like a baseball bat, whose long axis corresponds to long term changes in HRV, and whose short axis corresponds to short term changes in HRV. In contrast, the Poincare on the right is that of a man whose variability is much impaired, both long and short term. He died a few weeks after tracing was made from a rare cancer; a Carcinoid Tumor. Nonlinear measures of heart rate variability, such as this Poincare recurrence plot, have been found to be 96% accurate in (short-term) predictions of sudden death.

There are some linear Statistical Calculations (Centric, Ellipse Area, R2, SEE, SD1, SD2) which have been used to provide quantitative information regarding the Poincare graphic shape. The long axis of the Poincare plot indicates long range correlations of the signal, while the short axis of the Poincare indicates short-term correlations of the signal. The concept, and execution of a Dynamic Poincare plot is part of the inventive software. The movie is the result of an iterated mathematical formula. Characteristically, "time" is lost from a Poincare chart except for total time of the record. Current interest lies in the evolution of the Poincare plot and therefore, in an evolution that tracks time, and gives nonlinear analysis in a graphical form. Using either one physiological signal of more than one signal, put into normalized units, and even as a z-score. Interest in state change of physiological oscillation pressed the inventor to have software written that would show the details of evolution of the 24 hour Poincare. For example, first, a 24-hour Poincare plot (a recurrence plot with a lag of 1) of heart rate variability was created from a 24-hour Holter monitor recording. Then, the R-R intervals are extracted from the Holter recording. Next a single parameter of intervals (R-R) is plotted on the x-axis against the next R-R interval in the series plus one (R-R+1) on the y-axis. The calculation is iterated, with a selected "slice" of time as the chosen interval, in a moving window, from the first R-R interval to the last one recorded by the Holter monitor. A Poincare plot for 24-hours Holter monitoring contains twice 80,000 to 120,000 data points (heart beats). A healthy subject will display a characteristic Poincare shape showing how the beats are distributed. The shape of the Poincare plot is both age and gender specific. A dynamic Poincare plot is constructed by having a moving window of heartbeats in five minute segments, with no overlapping, for example. Each five minute calculated segment is shown on the outline of the 24 hour Poincare plot in a contrasting color (produced as part of the software). The program is run at a rate varied by the viewer, allowing correspondence between the log of activities and other physiological measures.

Figure 27:
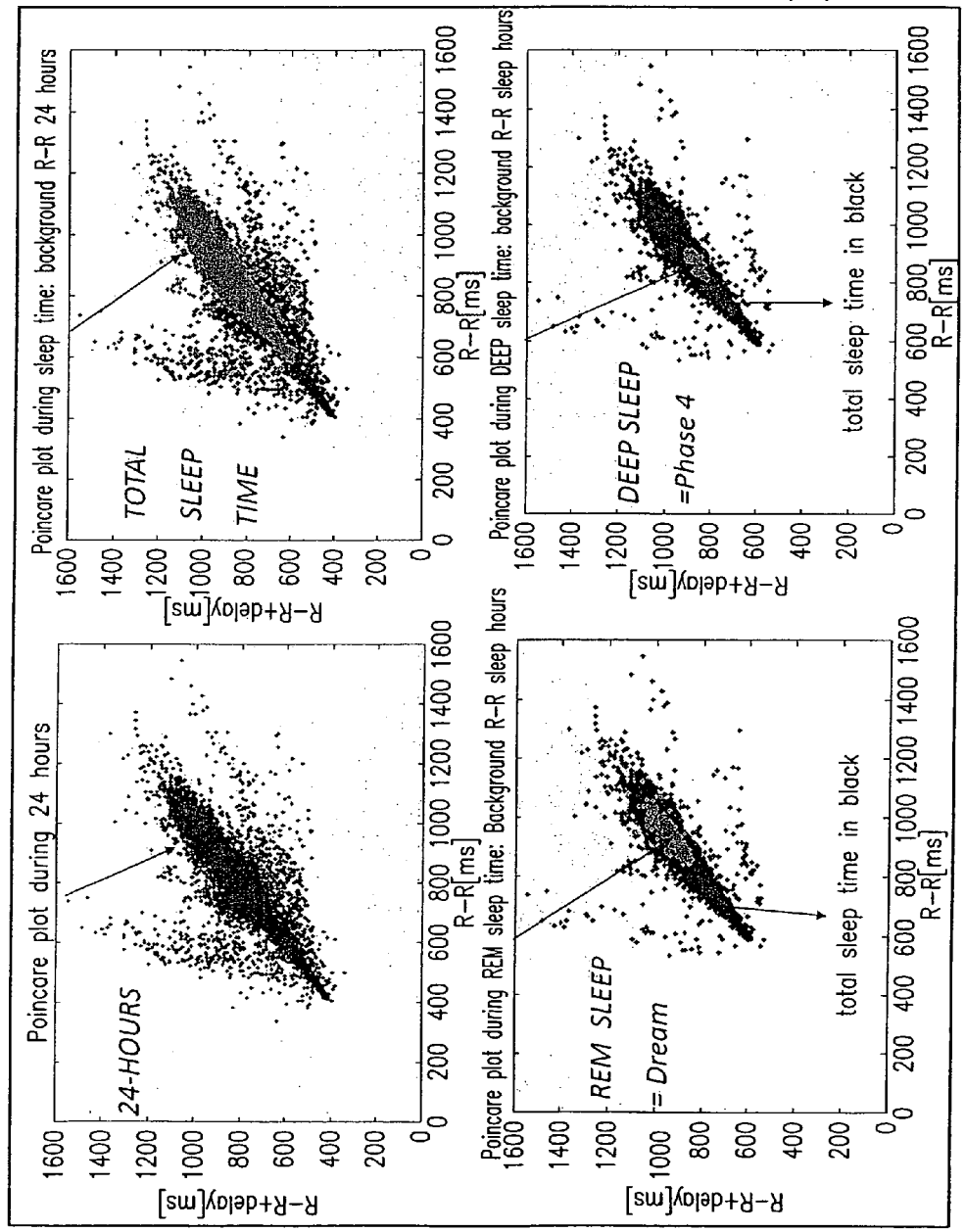
FIG. 27 are still frames captured from a movie of dynamic Poincare plots of heart rate variability sampled over 24 hours to show the relationship of several stages of the sleep cycle to the architecture of sleep.

We have observed that the Poincare plot, while varying between individuals is characteristic for a specific individual and recognizable over time. The Poincare plot diagrams a summary of the total data points that were processed. The inventor recognized that the Poincare plot is a static summary of the transitions made by a living system over an extended period of time. As such, it loses the temporal structure that orders the relationship of one component to the next, and transitions between states are therefore not seen. Understanding the limitation of the classical Poincare plot, this invention developed software was produced to visualize a Dynamic Poincare as an important element of this invention. The Dynamic Poincare is generated by processing shorter intervals of data points and overlaying that image on the 24 hour Poincare plot. The inventor calls these shorter intervals, slices of the number of data points that can fit into an interval of time. The slice is adjusted to contain a pre-selected time interval of data points, depending upon the application. For example, in the case of Holter data, a useful size slice for visualization of transitions of R-R intervals was empirically found to five minute intervals. The five minute slices contained hundreds of seconds of heartbeats. This slice (interval) is used to create a five minute Poincare plot which is then overlaid on an image of the full 24 hour Poincare Plot (in a contrasting color). As the next interval of five minutes is calculated by the software, the first interval plot (slice) is removed, and the process is re-iterated to produce the next interval (slice). The result is a dynamical view of a selected time slice interval) showing the evolution of the Poincare plot for the entire 24 hour recording. The result of this interval slicing dramatically reveals state changes during transitions, just as MRI's of the heart, sliced thinly, reveal the dynamic structure and function of the heart. Using this technique, state transitions became apparent both day and night, with moving icons tracking neurocardiac adaptation. During daytime, state changes of this biological measure (R-R intervals), are visible as the subject adapts to various intensities and types of activities. Likewise, it is obvious when the subject goes to sleep, and the architecture of the sleep is visible, as are the transition from sleep to awake. FIGS. 27(top left), 27(top right) are stop animation of a movie of dynamic Poincare plots. The top left is a 24 hours. Poincare, and the top right shows the part of that 24 hours that is sleep times. FIG. 27 (lower left) diagrams REM sleep, and FIG. 27 (lower right) diagrams dream sleep in relation to the 24 hour Poincare. These are still captures of the Poincare movie that is part of the invention. They are plots of Dynamic Poincare and the entropy analysis that they refer to. The x-axis is R-R interval for heart rate variability, and the y-axis is R-R+delay.

Although the Dynamic Poincare was initially developed to observe and analyze the evolution of the RRI from a time series, similar algorithms have been written on the request of this inventor, and applied to other physiological measures (data) that are utilized by this invention. A living organism is best observed dynamically, as it performs the processes of living.

Fourier and Wavelet analysis have been classically used to analyze a time series, however both of them treat the data as if it had stationarity, i.e., a single fractal pattern. These methods impose a fixed basis set on the data, and leave time-frequency uncertainty in the analysis, and this invention incorporates the understanding that all physiological signals are multi-fractals, and therefore, newer, nonlinear methods, as described elsewhere in this patent are more applicable to extract the important temporal information from the data sets.

Figure 28:
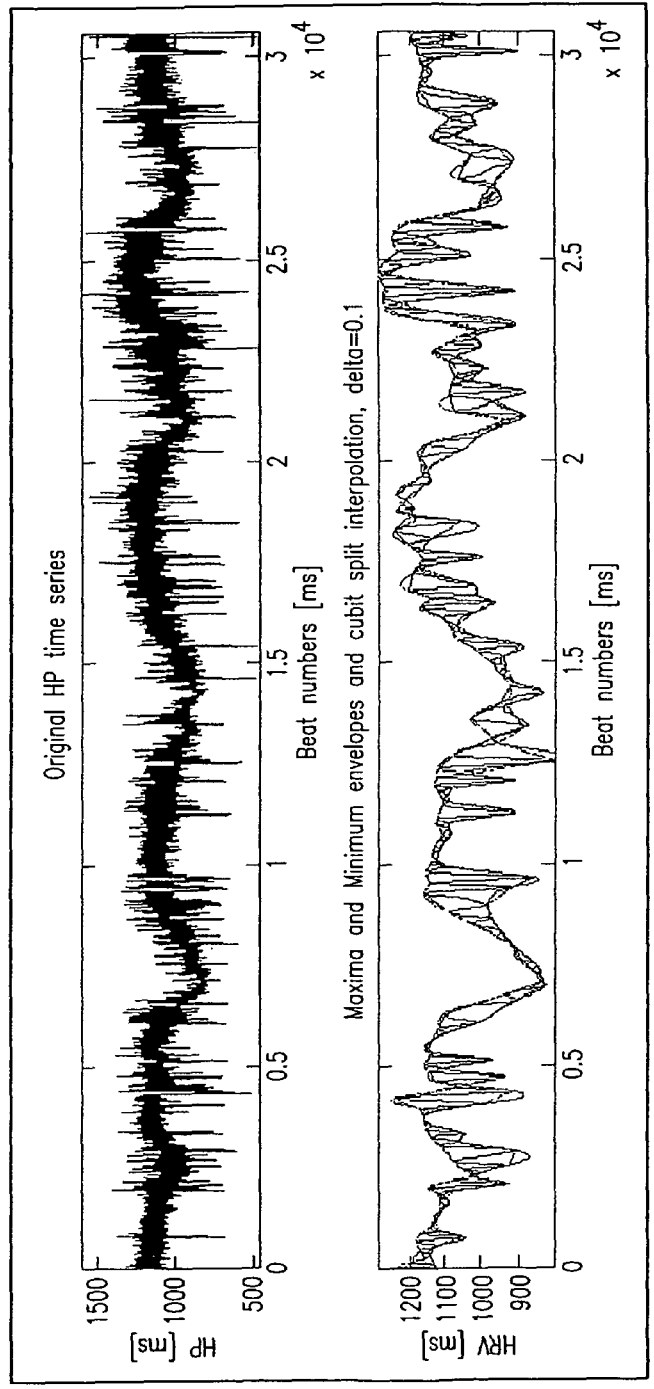
FIG. 28 is a Hilbert-Huang Transform from a 24 hour time series of heart rate variability.
Figure 29:
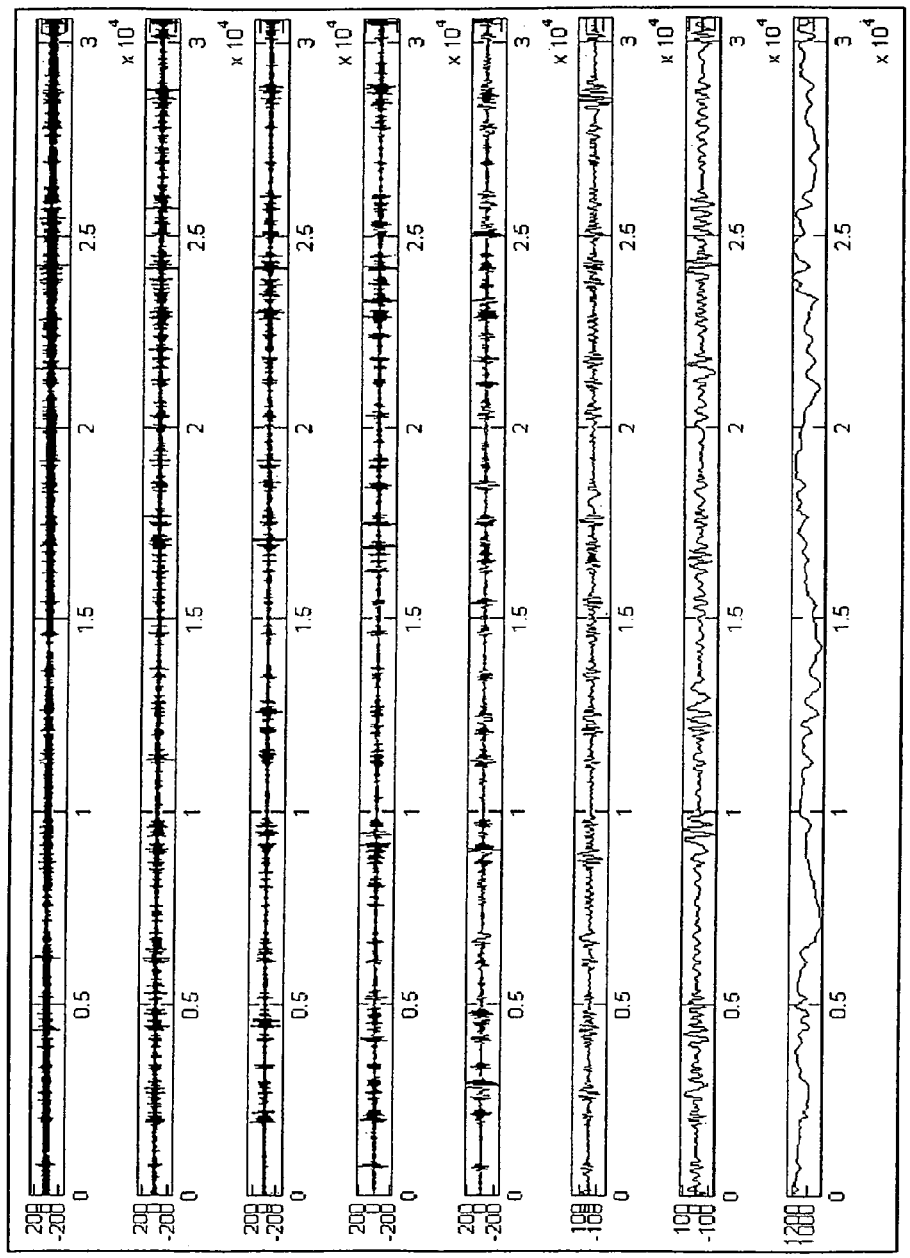
FIG. 29 is the Signal Mode Decomposition produced from the time series in FIG. 28.

The Hilbert-Huang Transform and Signal Decomposition, i.e., Empirical Mode Decomposition, originally invented to look at radio waves in the universe, has been found to be useful in processing other types of time series that are nonstationary and nonlinear. These are the properties of physiological signals. Heart rate variability is a data set that is nonstationary and nonlinear. Its signal can be decomposed into a small number of intrinsic mode functions using Hilbert transforms. The intrinsic mode functions yield instantaneous frequencies that are a function of time. The period of the signal can be found with distribution of the main frequency, and each of the higher frequencies equals the reciprocal of the signal period. FIG. 28 is part of the set of Hilbert-Huang Transform and Empirical Mode Decomposition graphs. The Hilbert-Huang Transform is applied to 24-hours of Heart Rate Variability data, and the signal is decomposed into its intrinsic modes. FIG. 29 (top) shows the time series for heart rate variability, with the lower drawing showing the maxima and minimum envelopes and cubit spline interpolation. FIG. 29 represents the fully decomposed signal of heart rate variability. This decomposed signal of heart rate variability has eight intrinsic modes, each of which codes within itself all of the patterns that make up heart rate variability, i.e., breathing, blood pressure, etc.

The Hilbert-Huang Transform and empirical mode decomposition for heart rate variability is shown for this nonstationary (multifractal) and nonlinear process. The data set consists of intrinsic modes of oscillations, where each mode consists of different simple intrinsic modes of oscillations. The data may have many different coexisting modes of oscillation, on superimposing on the others. The result is the final complicated data. Each of these oscillatory modes is represented by an intrinsic mode function (IMF), defined as follows: For the whole dataset, the number of extrema and the number of zero-crossings must either equal or differ at most by one, and at any point, the mean value of the envelope defined by the local maxima and the envelope defined by the local minima is zero. The IMF can have a variable amplitude and frequency as functions of time. In this example, the heart rate variability signal is decomposed into eight modes, each of which represents an oscillatory component of the heart rate variability, such as breathing, hormone release, etc. This inventor has found that the rate of change of the entropy of the high frequency oscillation is equal to the rate of change of the low frequency oscillation. This mathematical relationship can be used to decompose a complex nonlinear oscillation into its component frequencies, allowing for real time analysis with a single oscillatory input.

This inventor has found a relationship among the decomposed signals after application of the Hilbert-Huang transform to the entropy of intervals of the signal. It appears that the rate of change of the entropy (acceleration/deceleration of the system's orderliness) of the high frequency oscillations is the same as the rate of change of the low frequency signal.

A biological system whose rate of change of organization or disorganization of its highest frequency signal is equal to the rate of change of its lowest frequency signal, builds in itself a recursive element. When the system self-organizes, this recursive element, allows the system to remain synchronized over the entire range of its frequencies even as emergent properties develop. This is analogous to reverse engineering a system to into its constituent parts to understand how they work together.

The example of an amoeba will illustrate this point. An amoeba is a microscopic single-celled organism. Its digestive system is simply a tube that forms around its food, with an input and an output. As a rhythmic oscillation occurs along the length of the tube (amoeba), food is propelled in . . . and then out . . . . For an organism so small, oscillations of a limited number of frequencies are all that is necessary to serve as a simple digestive tract. The frequency of the oscillation changes depending upon the task the amoeba is involved in, yet the organism is small and simple enough in construction that this system of digestion works well.

As organisms grew more complex and larger, over evolutionary time, an entire digestive system emerges. In humans each part of the digestive system has its own intrinsic rhythm, yet the rhythms also share a mathematical relationship to one another so that their coordinated activities of digestions can occur. This coordination moves food through the system starting at the mouth and discharging waste from the anus. Using digestion in humans as an example: If swallowing has the highest frequency rhythm, and its entropy is equal to the rate of change of the longest frequency digestive rhythm (the colonic oscillations) peristaltic waves will move food along the entire length of the gastro-intestinal tract, even though parts of the tract, such as the stomach, might have a different rate of propulsion than either the mouth or colon.

Figure 30:
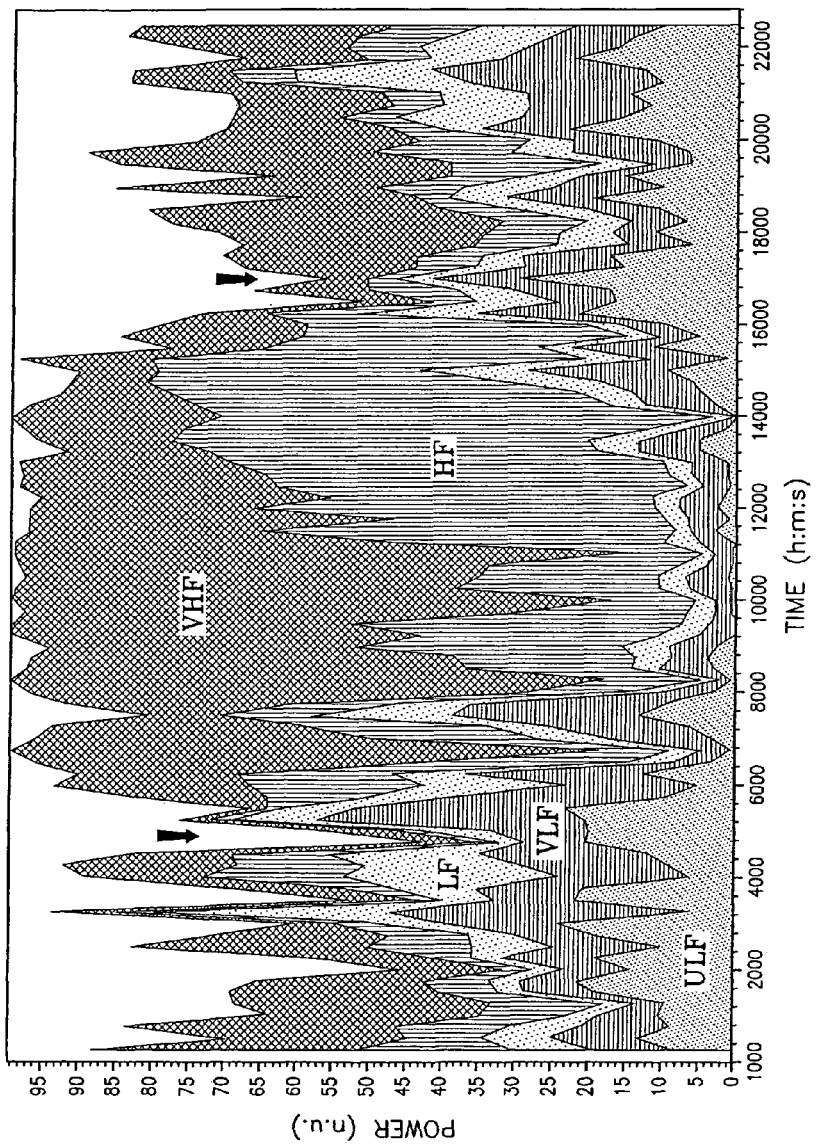
FIG. 30 is a stacked power graph of frequencies of heart rate variability collected over 24 hours from a person with server sleep apnea. Nighttime is between arrows, and VHF oscillations are prominent in Sleep Apnea.

The output from, at most, three physiological signals are all that is needed to describe the dynamics of a nonlinear system. The use of variability of heart rate, movement and EEG is a project that will provide a useful method by which to give a good way to study Drug Abusers. The expectation is a more complete understanding of the dynamics of that condition. After extracting the R-R intervals for each healthy subject during a 24-hour period, the sleep-time segment was separated from the awake-time segment. We used the accelerometer activity to verify the segments. FIG. 30 is a Stacked Power Graph showing a person with severe sleep apnea. This diagram of frequency power shows night (between the arrows). VHF oscillations have prominent power at night, indicating the apneic condition.

This person has sleep apnea as seen in the heart rate variability analysis by frequency. Note the peaks at the top of the stacked power graph that occur during the night in the very high frequency range.

Figure 31:
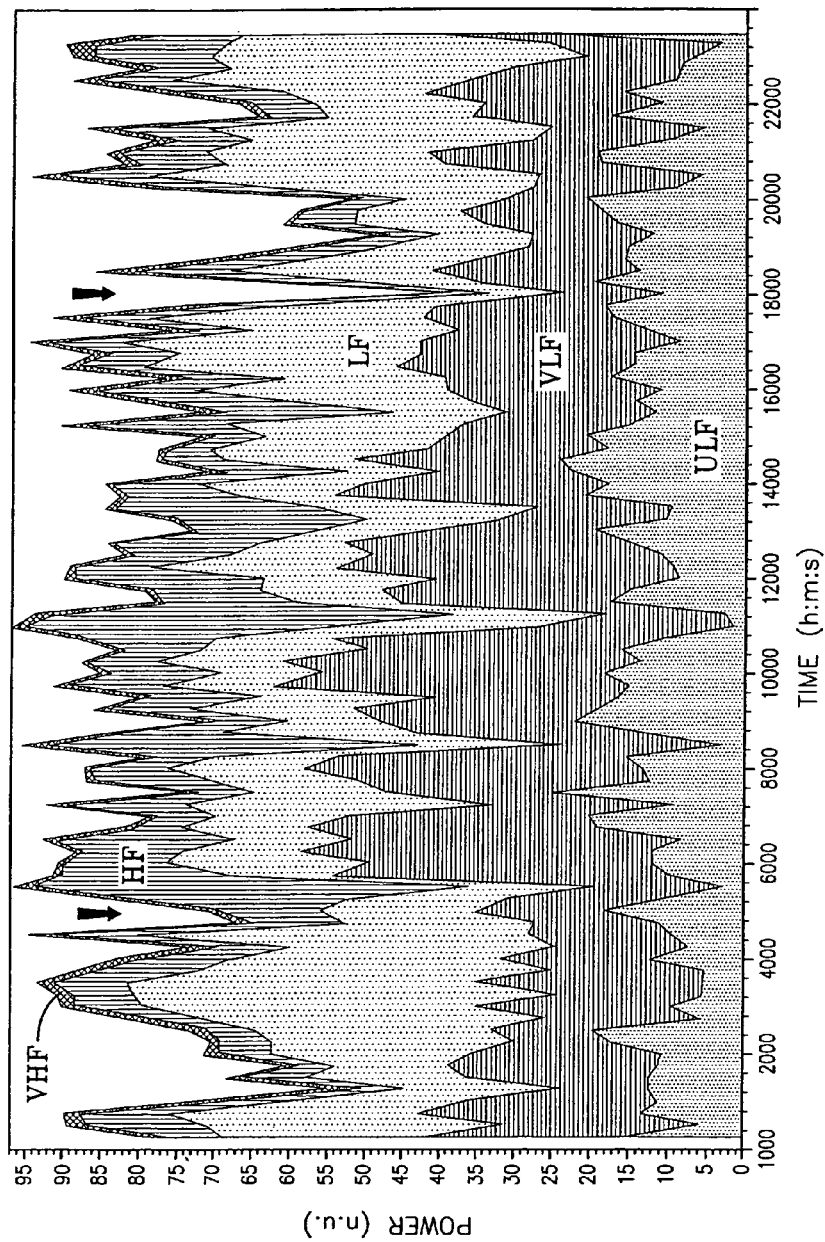
FIG. 31 is a stacked power graph of frequencies of heart rate variability over 24 hours from a person after treatment for sleep apnea. Nighttime is between the arrows, and VHF is no longer prominent after treatment.

FIG. 31 is a Stacked Power Graph of treated sleep apnea. Note that the VHF peaks have become normal size in size and the frequency no longer holds the power in it, but rather the frequency distribution is normal. Not sleep arrows. The x-axis is time in hours, and the Y-axis is power spectral density in normalized units (as is FIG. 30's axis).

Healthy people show greater oscillations in heart rate variability during the night. At night, healthy people (with normal hearts) have an equal quantity of high frequency and low frequency components or an LF/HF ratio of 1.0. In contrast, people with sleep apnea have an unusual inequality of very high frequency components and increased power in low frequency components, as well.

The diagnosis of Attention Deficit Hyperactivity Disorder was made in those people in whom the heart rate variability signal was processed in the frequency domain, people with Attention Deficit Hyperactivity Disorder characteristically showed a 30 second oscillation in their Autoregressive Spectrum analysis, a frequency spectrum of heart rate variability. After treatment with stimulant medication along with symptom resolution, that frequency peak is no longer present.

Figure 32:
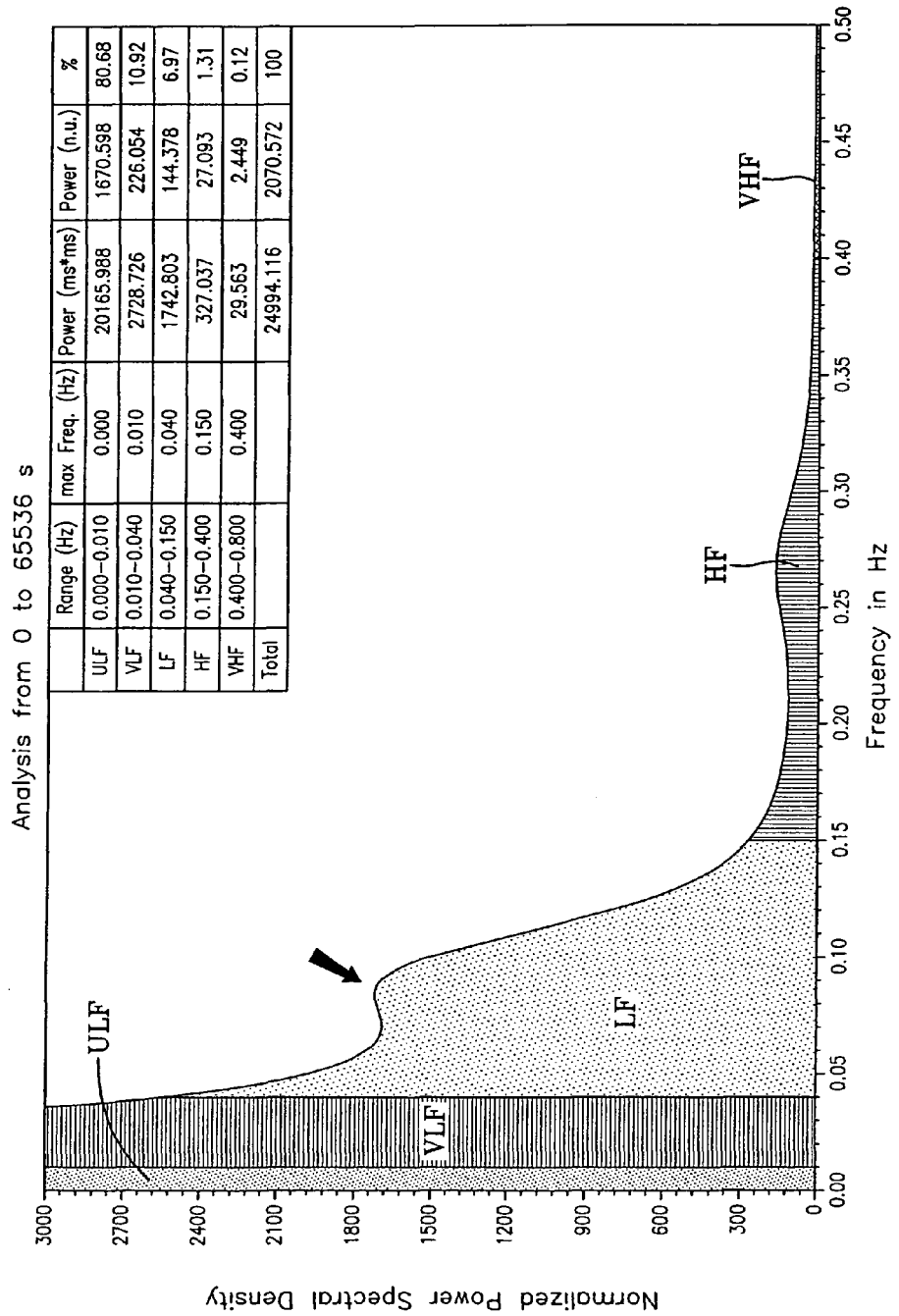
FIG. 32 is a frequency plot showing autocorrelation of heart rate variability frequency over 24 hours from a male with untreated Attention Deficit Disorder. Note the 30 second frequency peak in LF.

FIG. 32 is a plot of a male with untreated Attention Deficit Disorder. This autoregressive spectrum shows the power in each part of the frequency spectrum. With a 30 second oscillation (arrow) peakings both day and night, LF, in this person (and others, not shown) with Attention Deficit Hyperactivity Disorder.

Figure 33:
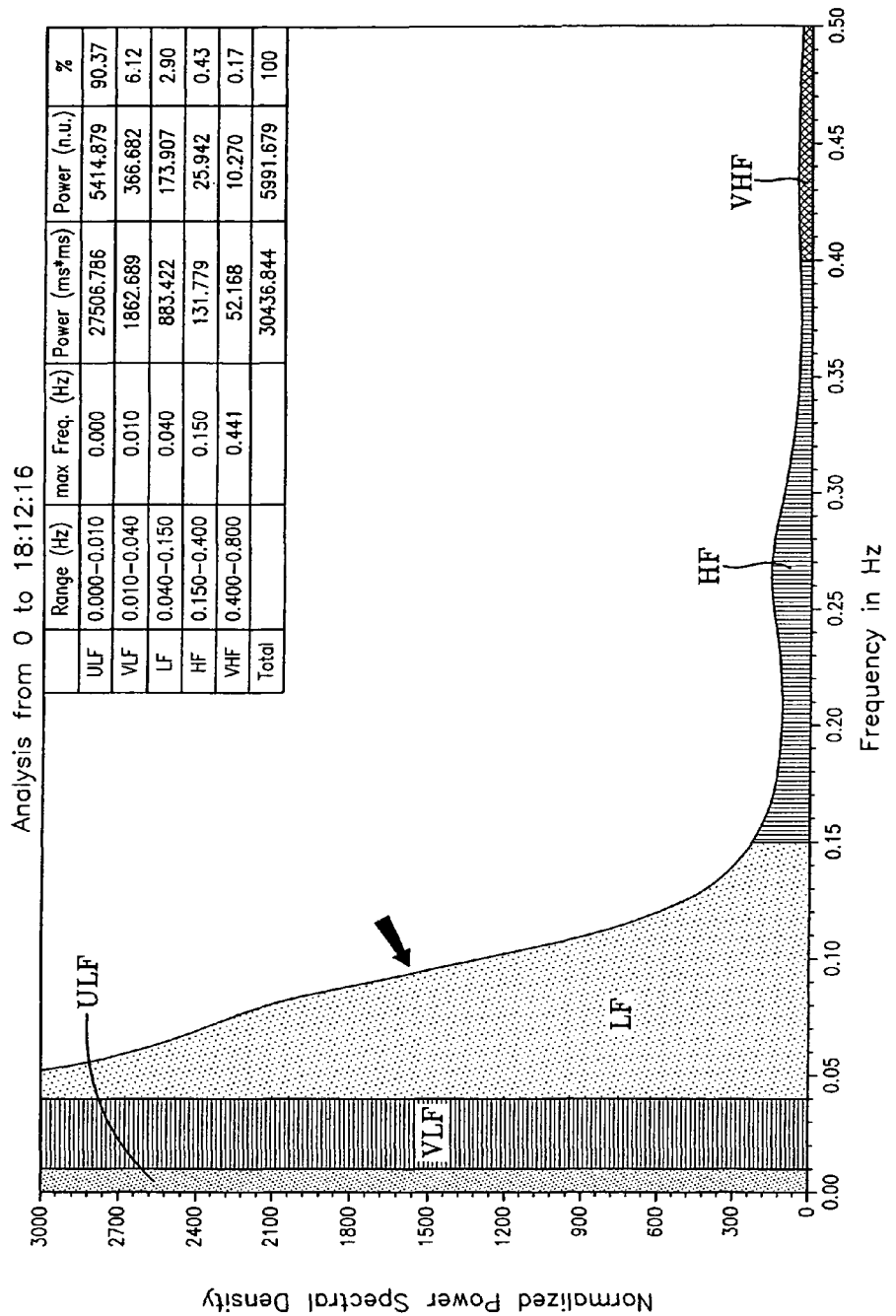
FIG. 33 is the same style plot in the same male after treatment. Note disappearance of the frequency peak at LF.

After pharmacological treatment, that frequency power in that peak returns to normal. FIG. 33 is the same plot after treatment for Attention Deficit Disorder. Note that the prominent 30 second oscillation has disappeared. Frequency is in Hz on the x-axis and power spectral density is on the y-axis.

As part of the inventive disclosure, a "Healthy corridor" (age and sex specific) was constructed using quantification of the algorithm for Approximate Entropy for heart rate variability. The algorithm $(ApEn(N,m,r))x$ quantifies the predictability of subsequent amplitude values of the signal based upon knowledge of previous amplitude values present in the time series. Approximate Entropy, $ApEn(N,m,r)$, is a measure whose relative values depend upon three parameters: the length of the analyzed sample (N); the number of previous values used for prediction of subsequent values (m), and the parameter r, usually called the filter factor. The filter factor is the most sensitive parameter, which, with an infinite amount of data, should approach zero. With finite amounts of data or/and measurement noise its value must be greater than the level of signal noise. First, entropy of sleep as well as that of wakefulness was investigated as two single values, where N is the length of each corresponding segment. Next, entropy for each sleep stage was quantified, using a moving window of five minutes, with no overlapping. In this case, N corresponded to the interval inside each window. The parameter, m, was selected between two and three and the filter factor r was selected as 0.1 SD.

Figure 34:
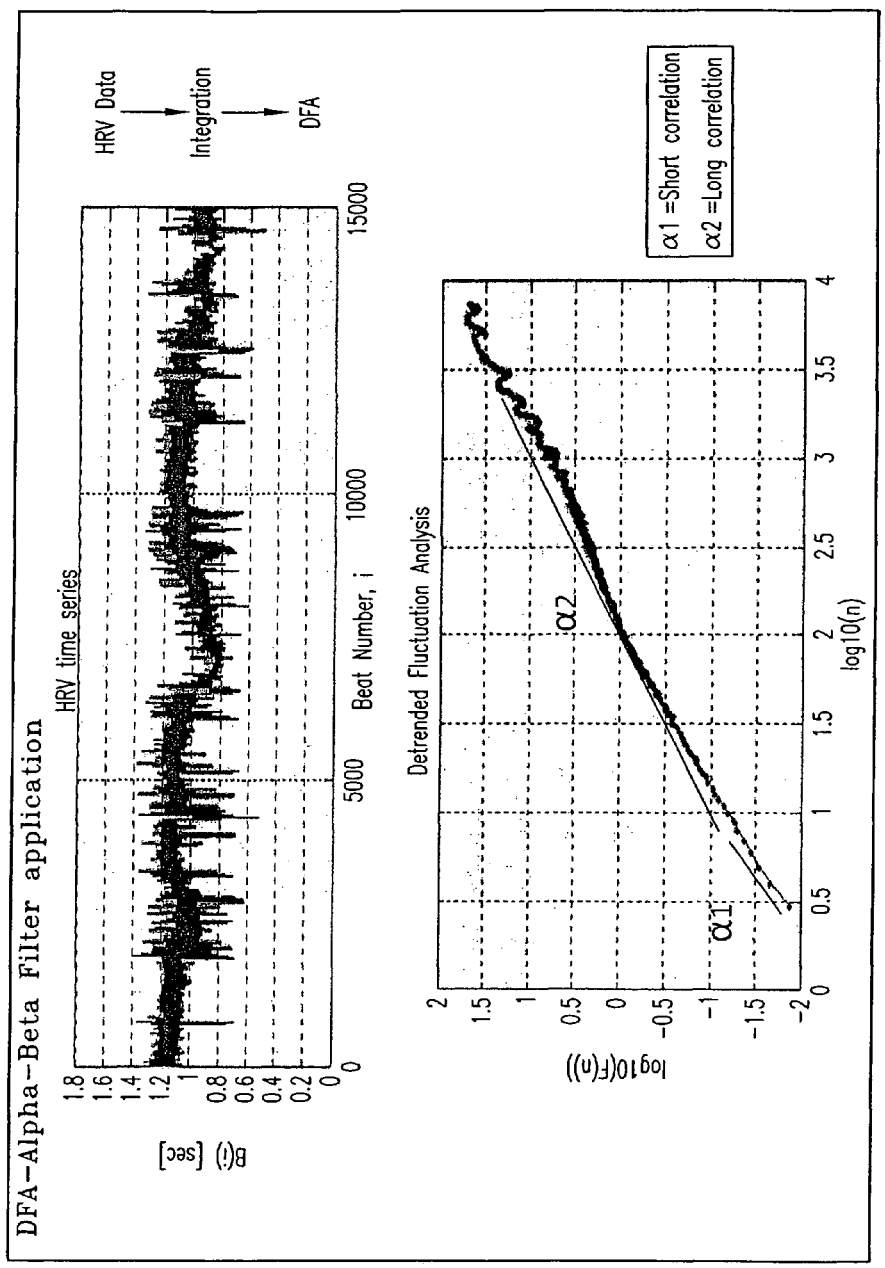
FIG. 34 is a graph showing the steps for Detrended Fluctuation Analysis for a single healthy female taken from a time series of heart rate variability over sleep.

Neurocardiac control comprises a nonlinear dynamical system, one that exists far away from equilibrium conditions, and as such, reveals long-term correlations that are self-similar. To demonstrate these correlations, we used Detrended Fluctuation Analysis, DFA. DFA is a nonlinear algorithm showing long-term correlations in a non-stationary time series, such as heart rate variability using a modified root-mean square analysis of a random walk (Echeverria et al., 2003). Using the interbeat interval, FIG. 34 is a graph showing the steps for Detrended Fluctuation Analysis for a single healthy female taken from a time series of heart rate variability collected over 24 hours. The top chart represents the HRV time series while the bottom chart shows by the short and the long correlations in the signal of the same single healthy subjects. The bottom diagram shows that time series analyzed as DFA showing the alphas.

Figure 35:
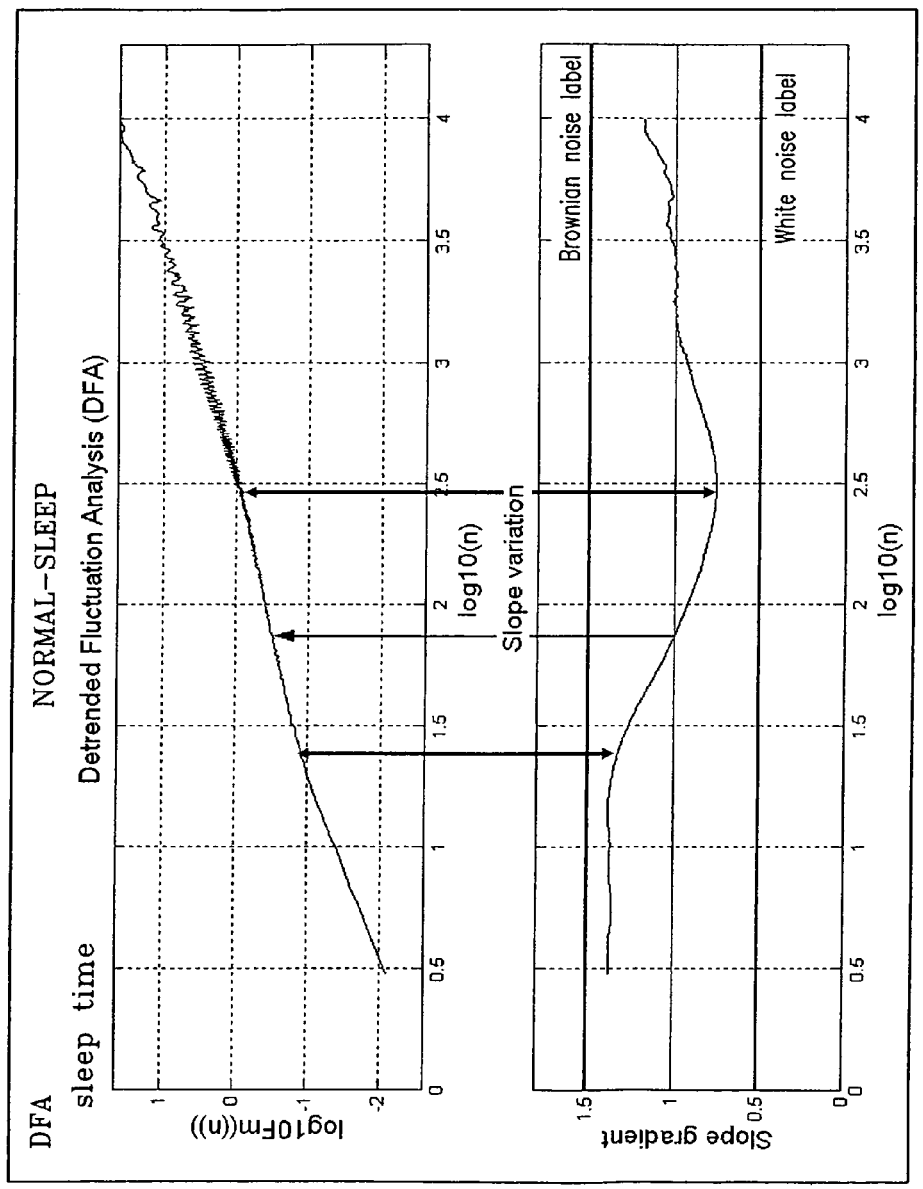
FIG. 35 is a graph showing Detrended Fluctuation Analysis of the same female and the method for capturing slope variations over the sleep time.
Figure 36:
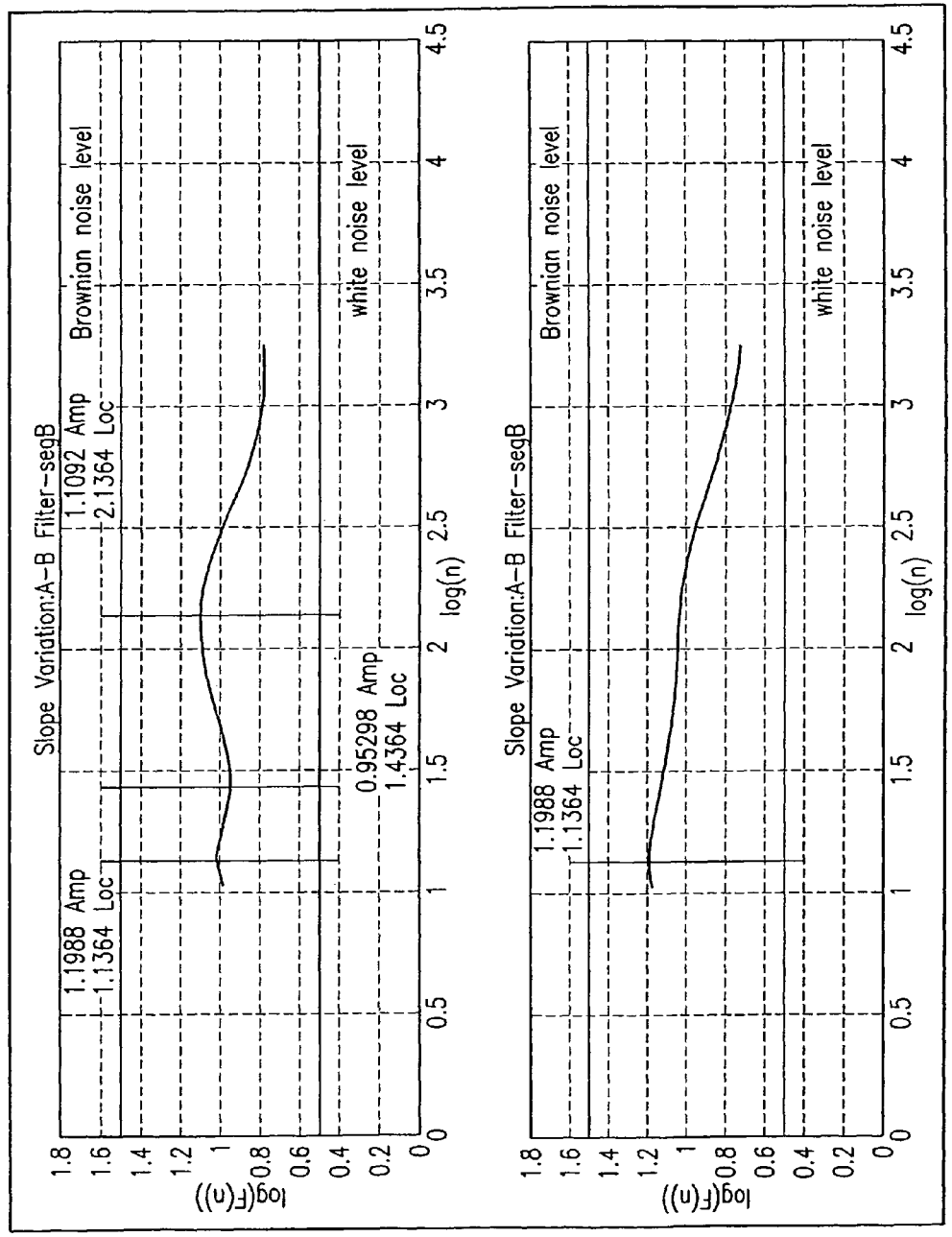
FIG. 36 is the Detrended Fluctuation Analysis of the healthy female (above) compared with an age matched female with Posttraumatic Stress Disorder.

FIG. 35 is a graph showing Detrended Fluctuation Analysis of the same female and the method for capturing slope variations at short time intervals over the course of the time for sleep. Taking many instaneous slopes gives a dynamic nonlinear analysis of sleep using DFAs. FIG. 36 is the Detrended Fluctuation Analysis of the healthy female (above) compared with an age matched female with Posttraumatic Stress Disorder, over the course of the nighttime. FIG. 35 shows the DFA of one healthy volunteer subject, while FIG. 36 shows the DFA for one-healthy subject (top) and for one unhealthy subject (bottom) of a person with Posttraumatic Stress Disorder.

Figure 37:
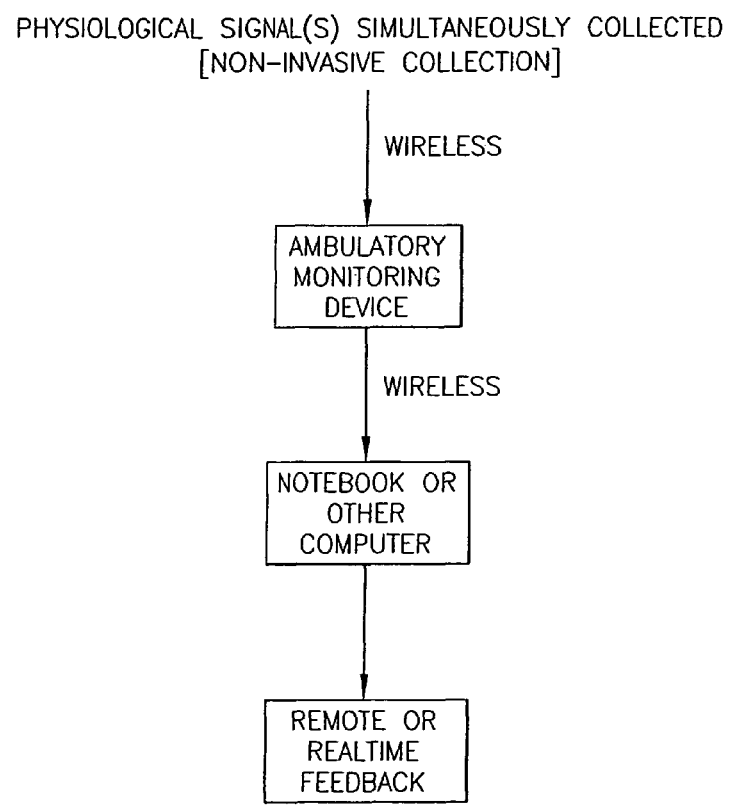
FIG. 37 is a flow diagram representing some basics in signal processing hardware defining this patent.

FIG. 37 is a flow diagram representing some basics in signal processing and hardware defining this patent. First, non-specific physiological signal(s) are collected over a time period using non-invasive collection procedures. These are brought to a wireless monitoring device worn on the subject. Through another wireless interface, the signals are transferred to a notebook (or other computer) or, alternatively, given back to the user in real time using algorithms. Linear and nonlinear processing of the signal(s) give either remote or realtime feedback for the specific purpose. Nonlinear processing of signals when simultansously collected and orthogonal to eachother are used to construct a precise temporal/spatial monitoring device used for diagnosis, tracking and treatment and developmental issues.

To further characterize the system, the inventor examined entropy as a function of age. There is a decrease in entropy as a function of age in the awake and sleep segments. Healthy ageing of the system results in more regularity in the system, with loss of complex organization. Entropy during sleep, decreasing with age, is still comparatively larger than that during wakefulness. Large variations in entropy are seen during sleep-time compared with wakefulness. Entropy during the sleep cycle contains large transitions from wakefulness to sleep as seen. Entropy is a robust measure of system complexity, and it is used in this patent.

Chaos, in the technical sense, is used to denote a type of time evolution in which the difference between two states that are initially closely similar grow exponentially over time. Chaos is more easily understood through a comparison with randomness and periodicity. Random behavior never repeats itself and is inherently unpredictable and disorganized. Periodic behavior is highly predictable because it always repeats itself over some finite time interval. Chaos is distinct from periodicity and randomness, but has characteristics of both. It looks disorganized but is actually organized. The most important criteria for chaotic behavior can be summarized as follows:

Chaos is deterministic and aperiodic and never repeats itself exactly. There are no identifiable cycles that recur at regular intervals.

Most chaotic systems have sensitive dependence on the initial conditions. In other words, very small differences in the initial conditions will later result in large differences in behavior.

Chaotic behavior is constrained. Although a system appears random, the behavior is bounded and does not wander off to infinity.

Chaotic behavior has a definite form. The behavior is constrained, and there is a particular pattern to the behavior. Nonlinear equations are of two types, monotonic and folded (i.e., exponential or parabola-like). This ambiguity gives rise to chaos under suitable conditions.

A simple attractor in which the orbit is a closed loop corresponds to sustained oscillation. This attractor is not chaotic. A chaotic attractor is a continuous curve confined to a finite region of phase space, which never crosses itself, and yet never closes on itself. These attractors are called "strange attractors." Chaotic behavior is also constrained, and there is a particular pattern to it. The patent is able to reconstruct the attractor of the physiological signal using nonlinear processing.

A fractal system was explained earlier and will further be explained at this point. A fractal system is a specific form of chaos. The geometry of chaotic attractors often suggests the existence of fractals. A fractal is a system which has the same structure on many measurement scales as discussed earlier. The normal heart rate time series is fractal-like and seems to display the fractal property of self-similarity over different time scales without a characteristic time scale. The power spectra of heart rate time series have been shown to concur with 1/f behavior, which is essential for fractal-like behavior and also characteristic of chaotic behavior.

Approximate entropy is a measure and parameter that quantifies the regularity or predictability of time-series data. It has been developed for time series to classify complex systems that include both deterministic chaotic and stochastic processes. The obvious advantage of this method is its incapability to discern changing complexity from a relatively small amount of data. This makes the approximate entropy measure applicable to a variety of contexts. This measure cannot certify chaos. Detrended fluctuation analysis was also discussed above. This analysis technique is a measurement which quantifies the presence or absence of fractal correlation properties and has been validated for time-series data. It was developed to characterize fluctuations on scales of all lengths. The self-similarity is a reference table of linear statistics of time/frequency which was obtained from commercial software.

The technical jargon meaning of chaos as 'deterministic' is exactly opposite to its common meaning of 'disorder.' Such a system can be described by nonlinear difference or differential equations that have a few independent variables. It is a dynamical system, meaning that the values of the variables can be determined from their values at the previous instant in time. However, their accuracy decreases as the calculation is continued for even longer times. Thus, their values are unpredictable in the long run, even though the system is completely deterministic. This is called sensitivity to initial conditions. The variables do not take on all possible values but are restricted to a limited set called a strange attractor which often has a fractal structure.

Chaos methods can analyze experimental data to determine if a system is random or if it can be described by a simple, deterministic set of nonlinear equations. These methods include determining the fractal dimension of the phase space set, Lyapunov exponents, and entropy measures. If the system is deterministic, these methods can uncover the relationship between the variables so that one can understand the system. They can also describe how to perturb the variables to control the behavior of the system. Many ecological systems have behavior so complex that it was assumed they could never be understood or controlled. If this analysis reveals that some of these systems are chaotic rather than random, then one may be able to understand and control them.

The nonlinear analysis aspect of the present invention is summarized at this time. References made to FIG. 9 which shows a flow diagram for part of the linear analysis and included the general nonlinear analysis.

Figure 19:
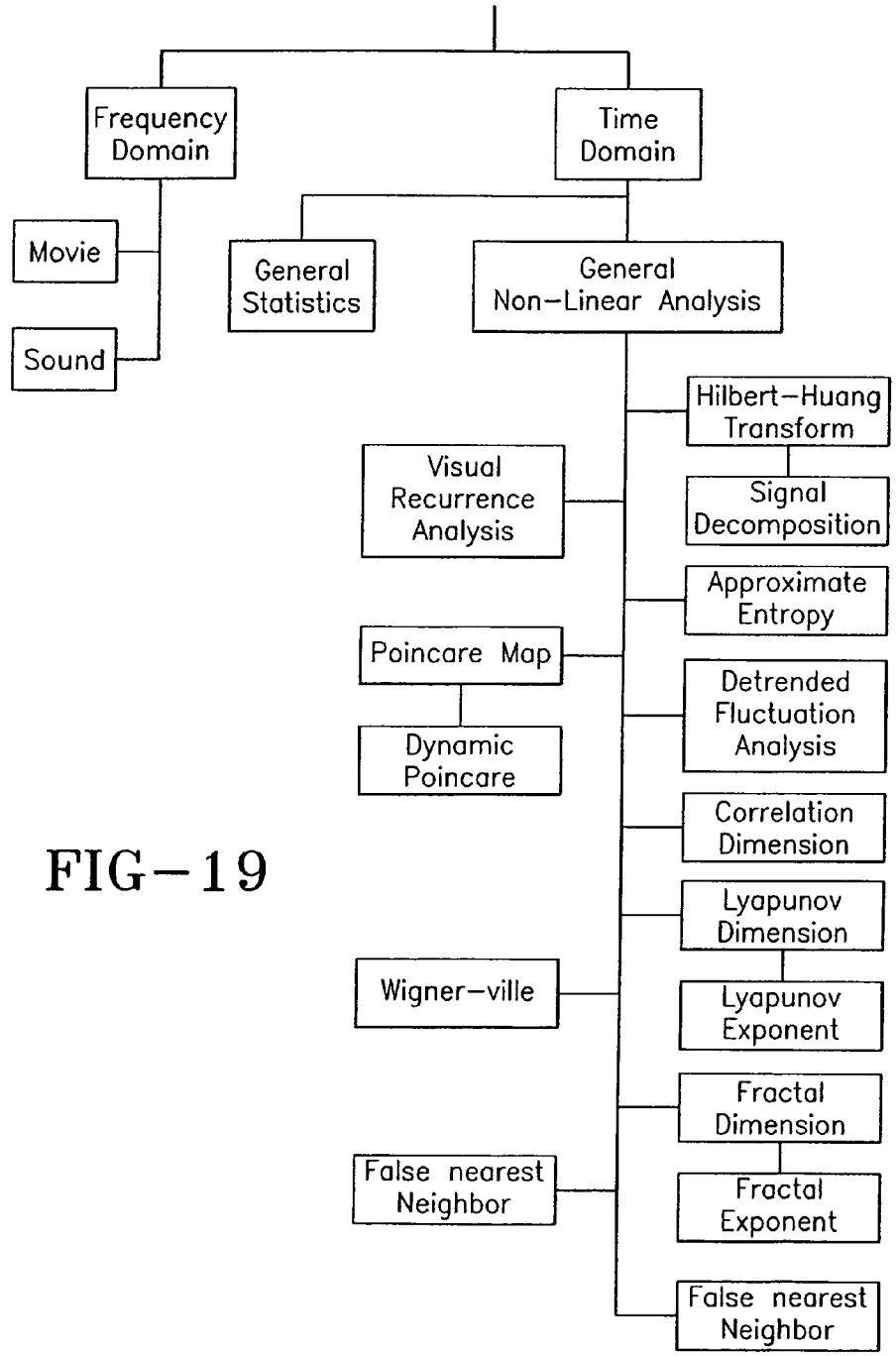
FIG. 19 is a flow chart showing nonlinear analysis from a physiological time series input. It represents several mathematical processes, a physiological signal, first linearly in both time and frequency domains, and then analysis by nonlinear mathematical methods.

The inputs to the general nonlinear analysis are the outputs from the time domain and the frequency domain referred to a layer in FIG. 19. The type of nonlinear analysis to be performed on the input signals depends upon what information is being sought. The Hilbert-Huang Transform decomposes the signals fed to the transform, and the respective transformed signals can be used to analyze the particular characteristic of a body being examined. The entropy of the envelope of the wave forms in the Hilbert-Huang Transform are the same for all frequency oscillations of the person being studied. Another nonlinear analysis is the Visual Recurrence Analysis. Hilbert-Huang Transform Signal Decomposition and Visual Recurrence Analysis is used to provide a qualitative and quantitative assessment and nonparametic prediction of nonlinear and chaotic time series.

Approximate Entropy is used to provide quantified physiological information underlying variability of the cardiac cycle.

The Approximate Entropy analysis is used for studying the changes in entropy during sleep and wakefulness, and is used for quantifying the predictability of subsequent amplitude values. Another nonlinear analysis is the detrended fluctuation analysis which is use for showing long-term correlations in a non-stationary time series.

The Dynamic Poincare is obtained from a Poincare map, and it shows the evolution of the Poincare plot. The Dynamic Poincare is calculated in subsequent time sequence, and its sequence is used to indicate various health characteristics of the person being studies.

The Correlation Dimension is another nonlinear analysis which can be performed. The Correlation Dimension is used to determine the dimensions of fractal objects, which can be used for examining the heart-time-rate series discussed above.

The Lyapunov Dimension, a measure used in the study of fractals, is another nonlinear value that can be obtained and from it the Lyapunov Exponent. The Lyapunov Exponent is a measure of the unpredictability of a time series as discussed above.

The Wigner-ville is a distribution which is used in the non-stationary analysis of electrocardiograms. The Wigner-ville nonlinear values are also obtainable using the nonlinear analysis pursuant to the present invention.

Fractal analysis can be an important part of the present invention. Another nonlinear analysis is the Fractal Dimension which is a measure of how complicated a self-similar figure is, and from this the Fractal Exponent is obtained. The Fractal Exponent of an electrocardiogram-derived RR interval variability is used for extracting hidden information from the heart rate variability as well as other measurements made according to the present invention.

False Nearest Neighbor is another nonlinear type of processing which can be used according to the present invention. The False Nearest Neighbor is an algorithmic technique for determining when the best shape of an attractor has arrived. Other nonlinear processes could be also be used in accordance with the present invention, depending on what values are sought to be obtained.

This invention finds applicability in diagnosing and monitoring the recovery from physical and psychiatric conditions. Examples of these conditions are the following:

Psychiatric conditions such as Depression, Anxiety, Post-traumatic Stress Disorder, Schizophrenia., and Attention Deficit Hyperactivity Disorder.

Psychiatric/neurological conditions such as migraine headaches, chronic pain.

Alzheimer's and other dementing diseases, etc.

Neurological conditions such as Lupus Erythymatosis, Multiple Sclerosis, Epilepsy, Systemic Sclerosis, Guillain-Barre Syndrome, paraplegia and quadriplegia.

Medical and psychiatric effects of aging.—both healthy aging and states of illness.

Normal and abnormal development from in-utero, infancy, childhood to old age.

Medical conditions such as diabetes mellitus and other metabolic conditions, cardiac conditions such as arrhythmias, heart block, heart transplants, endocrine conditions such as hyperthyroidism, Cushing's disease, and infectious or disease processes of the body/brain.

The invention can be used in the following applications:

Rehabilitation diagnosis, monitoring and treatment from virtually any psychiatric or physical condition.

Health maintenance.

Exercise physiology, training issues and predictive recognition of those young athletes at risk for sudden cardiac death.

Monitoring devices such as defibrillators, anesthesia machines, emergency medical technician devises, and other field devices prediction of acuity of emergency conditions.

Drugs and their effects both for pharmaceutical companies and for individuals.

Effectiveness of treatments (whether pharmacological, psychological, physiological, alternative therapies, health foods, and health supplements), for these measures are holistic.

Insurance companies and managed care corporations for measuring efficacy of treatments, in part because physiological measures can be used to distinguish insurance fraud from valid claims.

Fitness for duty for government crisis workers including police, firemen and emergency personnel.

Iconic representation of physiological parameters that can be easily read by all people regardless of language and culture. This allows these measures to be used for teaching in medical, security, health and other fields.

Recognition of terrorist and other subversives.

Mental retardation and autism, both for monitoring and tracking treatment.

Research and development of new medical and psychiatric treatments.

Accurate medical diagnosis by physicians and paraprofessionals.

Response of patients with cancer to cancer treatment.

Teaching about the body, brain and response to stress.

Prevention of stress related conditions.

Physical and psychiatric effects of toxins, natural disasters, and other crises.

Measurement of sequelae of medical and psychiatric conditions.

Risk management decisions.

Normal and pathological sleep: normal sleep development as well as diagnosis of pathological conditions with portable apparatus that allows one to sleep at home.

Chronobiology, space and deep sea environments, and other altered physically

Challenging environments.

Military classifications.

Communication with those who cannot speak or are not conscious in the usual sense (high transactions of the spinal cord, persistent vegetative states).

Criminal investigation and culpability issues.

Identification of at-risk children and adults.

Fitness to work: dangerous jobs following trauma,

Exercise physiology: personal fitness

Following neurological disease: Guillain Barre Syndrome, Epilepsy

Timing for chemotherapeutic agents

Toxicity of chemotherapeutic agents

Health and well-being after cancer chemotherapy
Anorexia nervosa
Brain infarction
Panic disorder
Work stress
Effect of kidney dialysis
Chiropractic—subluxations
Diving
Paragliding
Dangerous occupations: mining
Mental stress: policemen, rescue workers
Possibly for alcohol and drug recovery
Measures of emotional stress: pilot training, police and fireman training.

Single measure of heart rate variability has applications to the following:
Diagnosis of Attention Deficit Hyperactivity Disorder
Healing from Attention Deficit Hyperactivity Disorder
Sleep disturbance associated with Depression
Dementia
Schizophrenia—active disease, healing
Normal/abnormal sleep patterns associated with dangerous occupations
Autoimmune disease—tracking healing
Spinal cord Injury—autonomic dysfunction
Fitness to work: dangerous jobs following trauma,
Exercise physiology: personal fitness
Following neurological disease: Guillain Barre Syndrome, Epilepsy
Timing for chemotherapeutic agents
Toxicity of chemotherapeutic agents
Health and well-being after cancer chemotherapy
Anorexia nervosa
Brain infarction
Panic disorder
Work stress
Effect of kidney dialysis
Chiropractic—subluxations
Diving
Paragliding
Dangerous occupations: mining
Mental stress: policemen, rescue workers
Possibly for alcohol and drug recovery
Measures of emotional stress: pilot training, police and fireman.

This measure is somewhat predictive of the following as well.
Depression
Infant/child development: measures central nervous system complexity
Mental retardation
Sleep/wake rhythm disturbances
Monitoring antipsychotic drugs, and other psychoactive drugs as well.
Sleep screening and Diagnosis
Heart rate
Oxygen
Movement Embodiments of the present invention measure 99% of all sleep disorders. A family practice doctor or an internist can purchase the inventive equipment and then send a patient home with it to sleep one night. The doctor uploads the data to a central processing center. A report can be prepared to come back to the doctor (or the patient) the same or next day. Pediatricians, neurologists, psychiatrists, internists, family practitioners, cardiologists, oncologists, pulmonologists, nephrologists (dialysis), physiatrists, surgeons, emergency room physicians, etc., should be able to have effective uses of the inventive concepts disclosed herein. This includes all the sleep disorders, and with the correct algorithm, including nocturnal epilepsy as well.

Hardware Design for Multiparameter Analysis

The hardware systems used for our research have been commercially available ambulatory physiological monitors such as Holter monitors, movement/temperature/galvanic skin response and oximeter monitoring devices that collect large amounts of data that then need analysis and template matching.

It is the intent of the inventor to produce and customize the hardware specific for each application. There is a need for a monitoring device that is completely wireless, effortless to wear, with universal connectivity to a computer, PDA, or cellular phone interface. Thus the hardware needs universal connectivity, It must use low power, off the battery, yet transfer data at high speed. Meeting these requirements, allow physiological data collected in real time, with low latencies for what amounts to immediate processing and feedback. Ideally, the physiological bio-electrodes should be well insulated so as to reduce interference. Bio-electrodes of this nature can even send a signal without direct electrical contact with the skin, allowing for signal transmission through clothing. Thus a shirt, specialized for this purpose, could contain the necessary bio-sensors, making the equipment both lightweight and effortlessly wearable for long periods of time.

Wireless monitoring systems have used interfaces standard for these systems, i.e. GPS (1.2276 and 1.57542 GHz); Bluetooth=802.15 (2.45 GHz); 802.11, 802.11b, 802.11g (2.4 to 2.483 GHz) and 802.11a (5.180 GHz to 5.805 GHz). These interfaces have resulted in system that are not easily worn (poor wearability), or in systems whose sampling rate is inadequate for nonlinear analysis. At least 1000 data points are necessary to begin to perform nonlinear analysis and many more data points results in ever more accurate system analysis. Current technology employing high data sampling rates uses up enormous amounts of battery life. The result is a system with short battery life and slow transmission speed as well as lack of wearability. Systems that use the most popular wireless transmission, that of Bluetooth were designed for event monitors, rather than continuous monitors. Media Access Control (MAC) is a commercially available rapidly conducting wireless radio system that uses a 1 Mbps radio. Since more than half the volume of the entire wireless system is taken up by the battery, a very low power transceiver, consuming less than 10 mA in transmission mode (1 Mbps) and 22 mA in receiving mode is useful and necessary. FIG. 27. Drawing of wireless hook-up.

The connectivity is made universal through use of interfaces that include USB, Wi-Fi and Ethernet. QUASAR produces both the sensor, as well as an ultra-compact, low-power wireless sensor node, called Eco. The system is smaller than a dime! For each placed sensor. In this manner multiparameter linear and nonlinear analysis of several simultaneously collected physiological signals such as EKG, movement, oxygen, glucose monitoring, etc. can be collected in real time, analyzed with very short latencies, and adapted to a variety of medical, psychiatric and general health issues.

The invention has been described in detail with particular emphasis on the preferred embodiment thereof. However, other variations of the invention may occur to those skilled in the art from the description set forth above and in the appended claims.

I claim:

1. A non-invasive method for diagnosing the state or condition of a human or animal or other living organism, the living organism generating physiological modulating signals, the modulating signals having temporal-spatial organization characterized by dynamic patterns with fractal structure that varies in both frequency and amplitude, said method comprising:

simultaneously recording, as a sequence of temporal-spatial values, the variance of at least one physiological modulating signal over a period that is generally greater than two minutes and generally less than twenty-four hours;

plotting each sequence of temporal-spatial values so as to display amplitude as a function of time;

plotting each sequence of temporal-spatial values so as to display frequency as a function of time:

calculating first and second derivatives of the respective temporal-spatial value sequence plottings in order to determine velocity and acceleration, as a function of time, for each of the plottings of said at least one physiological modulating signal;

converting each data point in each of the temporal-spatial value sequence plottings into normalized units, using linear and nonlinear mathematical tools so that amplitude and frequency patterns of said at least one monitored physiological modulating signal can be directly compared with established sets of amplitude and frequency patterns reflective of particular psychiatric and/or physical disorders; and diagnosing a psychiatric and/or physical disorder by determining which of said established sets of patterns, with their transitional states, substantially correspond to those of the monitored physiological modulating signals.

2. The non-invasive method of claim 1 wherein:

said step of monitoring at least one physiological modulating signal includes monitoring the heartbeat of the living organism to obtain temporal-spatial values of the heart beat; and the step of processing the respective temporal-spatial values includes processing said respective temporal-spatial values of the heartbeat in order to obtain a variance of a set of inter-beat intervals and, thereby, establish heart rate variability.

3. The non-invasive method of claim 2 wherein said step of processing said the respective temporal-spatial values of the heartbeat comprises analyzing said heart rate variabilities as linear values in frequency regions selected from the group consisting of VHF, HF, LF, VLF and ULF regions.

4. A non-invasive method for diagnosing the state or condition of a human or animal or other living organism, the living organism generating physiological modulating signals, the modulating signals having temporal-spatial organization characterized by dynamic patterns with fractal structure that varies in both frequency and amplitude, said method comprising:

simultaneously recording, as a sequence of temporal-spatial values, the variances of at least two physiological modulating signals;

plotting each sequence of temporal-spatial values so as to display amplitude as a function of time;

plotting each sequence of temporal-spatial values so as to display frequency as a function of time;

calculating first and second derivatives of the respective temporal-spatial value sequence plottings in order to determine velocity and acceleration, as a function of time, for each of said at least two physiological modulating signals;

converting each data point in each of the temporal-spatial value sequence plottings into synchronized normalized units, using linear and nonlinear mathematical tools so that a set of amplitude and frequency patterns corresponding to said at least two monitored physiological modulating signals can be directly compared with each other and with established sets of amplitude and frequency patterns reflective of particular psychiatric and/or physical disorders; and diagnosing a psychiatric and/or physical disorder by determining which of said sets of patterns substantially correspond to the set of patterns corresponding to said at least two monitored physiological modulating signals.

5. A method of diagnosing a person according to claim 4 wherein said second physiological-modulating parameter is orthogonal to said first physiological modulating parameter.

6. A method of diagnosing a person according to claim 4 wherein: said step of monitoring a second physiological-modulating parameter of comprises monitoring the heartbeat of the person to obtain temporal-spatial values of the heartbeat; said step of monitoring a second physiological-modulating signal of the person simultaneously with the monitoring of the first physiological-modulating signal comprises monitoring the movement of the person to obtain timed values of the movement simultaneously with the monitoring of the heartbeat of the person; said step of processing said first set of temporal-spatial values to obtain a first-measured set of variances comprises processing said temporal-spatial values of the heartbeat to obtain a variance of a set of interbeat intervals and establish heart rate variability; and said step of processing said second set of temporal-spatial values to obtain a second set of variances comprises processing said temporal-spatial measurements of movement (acceleration) to obtain a movement variance and establish a movement variability.

7. A method of diagnosing a person according to claim 6 wherein said step of processing said first set of temporal-spatial values of the heartbeat comprises analyzing said heart rate variances as linear values in frequency regions of VHF, HF, LF, VLF and ULF regions, and wherein said step of processing said second set of temporal-spatial measurements of movement variances in VHF, HF, LF, and VLF and ULF regions.

8. A method of diagnosing according to claim 7 wherein the step of analyzing said movement variances in the VHF, HF, LF, VLF and ULF regions comprises calculating the variance in the longitudinal and transverse acceleration, and for certain cases calculated variances are processed and converted into normalized units.

* * * * *